(12) United States Patent
Tsai et al.

(10) Patent No.: US 10,435,685 B2
(45) Date of Patent: Oct. 8, 2019

(54) COMPOSITIONS AND METHODS FOR ENRICHMENT OF NUCLEIC ACIDS

(71) Applicant: Pacific Biosciences of California, Inc., Menlo Park, CA (US)

(72) Inventors: Yu-Chih Tsai, Fremont, CA (US); Igor Drasko Vilfan, East Palo Alto, CA (US); Khai Luong, San Francisco, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 631 days.

(21) Appl. No.: 14/995,646

(22) Filed: Jan. 14, 2016

(65) Prior Publication Data

US 2016/0208241 A1    Jul. 21, 2016

Related U.S. Application Data

(63) Continuation-in-part of application No. 14/830,293, filed on Aug. 19, 2015, now abandoned.

(60) Provisional application No. 62/039,319, filed on Aug. 19, 2014.

(51) Int. Cl.
*C12N 15/10* (2006.01)
*C12Q 1/6806* (2018.01)
*C40B 50/06* (2006.01)
*C12Q 1/6869* (2018.01)

(52) U.S. Cl.
CPC ....... *C12N 15/1093* (2013.01); *C12Q 1/6806* (2013.01); *C12Q 1/6869* (2013.01); *C40B 50/06* (2013.01)

(58) Field of Classification Search
None
See application file for complete search history.

(56) References Cited

U.S. PATENT DOCUMENTS

| 5,710,000 A | 1/1998 | Sapolsky et al. |
|---|---|---|
| 6,361,947 B1 | 3/2002 | Dong et al. |
| 6,917,726 B2 | 7/2005 | Levene et al. |
| 7,013,054 B2 | 3/2006 | Levene et al. |
| 7,033,764 B2 | 4/2006 | Korlach et al. |

(Continued)

FOREIGN PATENT DOCUMENTS

| WO | 2007/075873 A2 | 7/2007 |
|---|---|---|
| WO | 2007/075987 A2 | 7/2007 |

(Continued)

OTHER PUBLICATIONS

Akhmedov, et al. "Human 100-kDa Homologous DNA-Pairing Protein is the Splicing Factor PSF and Promotes DNA Strand Invasion," Nucleic Acids Res. (2000) 28(16):3022-30.

(Continued)

*Primary Examiner* — Kaijiang Zhang
(74) *Attorney, Agent, or Firm* — David C. Scherer

(57) ABSTRACT

Methods are provided for reducing the complexity of a population of nucleic acids prior to performing an analysis of the nucleic acids, e.g., sequence analysis. The methods result in a subset of the initial population enriched for a target region, which is typically located within one or more target fragments. The methods are particularly useful for analyzing populations having a high degree of complexity, e.g., chromosomal-derived DNA, whole genomic DNA, or mRNA populations.

27 Claims, 11 Drawing Sheets

Specification includes a Sequence Listing.

(56) References Cited

U.S. PATENT DOCUMENTS

| | | | |
|---|---|---|---|
| 7,052,847 | B2 | 5/2006 | Korlach et al. |
| 7,056,661 | B2 | 6/2006 | Korlach et al. |
| 7,056,676 | B2 | 6/2006 | Korlach et al. |
| 7,170,050 | B2 | 1/2007 | Turner et al. |
| 7,181,122 | B1 | 2/2007 | Levene et al. |
| 7,292,742 | B2 | 11/2007 | Levene et al. |
| 7,302,146 | B2 | 11/2007 | Turner et al. |
| 7,384,737 | B2 | 6/2008 | Barnes |
| 7,745,116 | B2 | 6/2010 | Williams |
| 7,901,889 | B2 | 3/2011 | Christians et al. |
| 7,910,302 | B2 | 3/2011 | Drmanac et al. |
| 7,910,354 | B2 | 3/2011 | Drmanac et al. |
| 8,003,330 | B2 | 8/2011 | Heiner et al. |
| 8,143,030 | B2 | 3/2012 | Maxham et al. |
| 8,153,375 | B2 | 4/2012 | Travers et al. |
| 8,236,499 | B2 | 8/2012 | Patel et al. |
| 8,546,553 | B2 | 10/2013 | Terns et al. |
| 8,697,359 | B1 | 4/2014 | Zhang |
| 2003/0059955 | A1 | 3/2003 | Barndad |
| 2005/0019776 | A1 | 1/2005 | Callow et al. |
| 2005/0100911 | A1 | 5/2005 | Patil et al. |
| 2005/0130173 | A1* | 6/2005 | Leamon ............ B01L 3/502707 506/2 |
| 2006/0040300 | A1 | 2/2006 | Dapprich et al. |
| 2007/0003938 | A1 | 1/2007 | Fu et al. |
| 2007/0161017 | A1 | 7/2007 | Eid et al. |
| 2008/0090733 | A1 | 4/2008 | Dapprich et al. |
| 2009/0047674 | A1 | 2/2009 | Dapprich et al. |
| 2009/0162845 | A1 | 6/2009 | Rabbani et al. |
| 2009/0233291 | A1 | 9/2009 | Chen et al. |
| 2009/0263798 | A1 | 10/2009 | Dapprich et al. |
| 2009/0264299 | A1 | 10/2009 | Drmanac et al. |
| 2009/0305419 | A1 | 12/2009 | Miller |
| 2010/0286070 | A1 | 11/2010 | Verheyden et al. |
| 2011/0033854 | A1 | 2/2011 | Drmanac et al. |
| 2011/0183320 | A1 | 7/2011 | Flusberg et al. |
| 2011/0189776 | A1 | 8/2011 | Terns et al. |
| 2011/0287512 | A1 | 11/2011 | Paschon et al. |
| 2012/0071359 | A1 | 3/2012 | Sun et al. |
| 2012/0196279 | A1 | 8/2012 | Underwood et al. |
| 2012/0258868 | A1 | 10/2012 | Sapolsky et al. |
| 2012/0322666 | A1 | 12/2012 | Pham et al. |
| 2012/0322692 | A1 | 12/2012 | Pham et al. |
| 2013/0130248 | A1 | 5/2013 | Haurwitz et al. |
| 2013/0323725 | A1 | 12/2013 | Peter et al. |
| 2014/0038241 | A1 | 2/2014 | Zhou et al. |
| 2014/0068797 | A1 | 3/2014 | Doudna et al. |
| 2014/0127752 | A1* | 5/2014 | Zhou et al. .... C12Y 301/21001 435/91.53 |
| 2014/0134610 | A1 | 5/2014 | Pham et al. |
| 2014/0272959 | A1 | 9/2014 | Wu et al. |
| 2014/0302563 | A1 | 10/2014 | Doudna et al. |
| 2014/0315985 | A1 | 10/2014 | May et al. |
| 2014/0356867 | A1 | 12/2014 | Peter et al. |
| 2014/0357523 | A1 | 12/2014 | Zeiner et al. |
| 2015/0225773 | A1 | 8/2015 | Farmer et al. |
| 2016/0017396 | A1 | 1/2016 | Cann et al. |
| 2017/0073747 | A1* | 3/2017 | Joung ................ C12N 15/1093 |

FOREIGN PATENT DOCUMENTS

| | | | |
|---|---|---|---|
| WO | 2007/076057 A2 | 7/2007 | |
| WO | 2012/065043 A2 | 5/2012 | |
| WO | 2013/176772 A1 | 11/2013 | |
| WO | 2013/188638 A2 | 12/2013 | |
| WO | 2014/022702 A2 | 2/2014 | |
| WO | 2014/150624 A1 | 9/2014 | |
| WO | WO-2015089351 A1 * | 6/2015 | ............... C12N 9/22 |
| WO | 2016014409 A1 | 1/2016 | |

OTHER PUBLICATIONS

Barany, F. "The Ligase Chain Reaction in a PCR World," Genome Res. (1991) 1: 5-16.

Bi, et al. "Human and Yeast Rad52 Proteins Promote DNA Strand Exchange," Proc. Natl. Acad. Sci. U.S.A. (2004) 101(26):9568-72.

Callow, et al. "Selective DNA Amplification from Complex Genomes Using Universal Souble-Sided Adapters," Nucleic Acids Res. (2004) 32(2):e21.

Chen, et al., "Cut Site Selection by the Two Nuclease Domains of the Cas9 RNA-Guided Endonuclease," J Biol Chem (2014) 289(19):13284-94.

Demidov, et al. "Duplex DNA Capture," Curr. Issues Mol. Biol. (2000) 2(1):31-35.

Dhopeshwarkar, et al. "Electrokinetic Concentration Enrichment within a Microfluidic Device Using a Hydrogel Microplug," Lab Chip (2005) 5:1148-1154.

Ferrin, et al. "Sequence-Specific Ligation of DNA Using RecA Protein," Proc. Natl. Acad. Sci. U.S.A. (1998) 95:2152-2157.

Gibson, et al. "Chemical Synthesis of the Mouse Mitochondrial Genome," Nature Methods (2010) 7:901-903.

Gibson, et al. "Enzymatic Assembly of DNA Molecules up to Several Hundred Kilobases," Nature Methods (2009) 6:343-345.

Honigberg, et al. "Ability of RecA Protein to Promote a Search fo Rare Sequences in Duplex DNA," Proc. Natl. Acad. Sci. U.S.A. (1986) 83:9586-9590.

Hsu, et al., "DNA targeting specificity of RNA-guided Cas9 nucleases," Nature Biotechnology (2013) 31(9):827-832.

Huang, et al. "Solid-Phase Purification of Gene Synthesis Products Using Magnetic Beads," Proc. of SPIE (2008) 7269:A1-11.

Jiang, et al., "Demonstration of CRISPR/Cas9/sgRNA-mediated Targeted Gene Modification in *Arabidopsis*, Tobacco, Sorghum and Rice," Nucleic Acids Research (2013) 41(20): e188.

Jinek, et al., "A Programmable Dual-RNA-Guided DNA Endonuclease in Adaptive Bacterial Immunity," Science (2012) 337:816-821.

Jordan, et al. "Genome Complexity Reduction for SNP Genotyping Analysis," Proc. Natl. Acad. Sci. U.S.A. (2002) 99(5):2942-7.

Kim, et al., "Precision genome engineering with programmable DNA-nicking enzymes," Genome Research (2012) 22:1327-1333.

Mali, et al., "Cas9 as a versatile tool for engineering biology," Nature Methods (2013) 10(10):957-963.

Mali, et al., "CAS9 transcriptional activators for target specificity screening and paired nickases for cooperative genome engineering," Nature Biotechnology (2013) 31:833-838.

Mertes, et al. "Targeted Enrichment of Genomic DNA Regions for Next-Generation Sequencing," Briefings in Functional Genomics (2011) 10(6):374-386.

Naumann, et al. "A Distinct DNA-Methylation Boundary in the 5'-Upstream Sequence of the FMR1 Promoter Binds Nuclear Proteins and is Lost in Fragile X Syndrome," Am. J. Hum. Genet. (2009) 85(5):606-616.

Noirot, et al. "DNA Strand Invasion Promoted by *Escherichia coli* ReeT Protein," J. Biol. Chem. (1998) 273(20):12274-80.

Ran, et al., "Genome Engineering Using the CRISPR-Cas9 System," Nature Protocols (2013) 8(11):2281-2308.

Rigas, et al. "Rapid Plasmid Library Screening Using RecA-Coated Biotinylated Probes," Proc. Natl. Acad. Sci. U.S.A. (1986) 83:9591-9595.

Rybalchenko, et al. "Strand Invasion Promoted by Recombination Protein β of Coliphage λ," Proc. Natl. Acad. Sci. U.S.A. (2004) 101(49):17056-60.

Taidi-Laskowski, et al. "Use of RecA Protein to Enrich for Homologous Genes in a Genomic Library," Nucleic Acids Res. (1988) 16(16):8157-8169.

Vieregg, et al. "Selective Nucleic Acid Capture with Shielded Covalent Probes," J. Am. Chem. Soc. (2013) 135(26):9691-9699.

Weisner, et al. "Purification of Mitochondriral DNA from Total Cellular DNA of Small Tissue Samples," Gene (1991) 98:277-281.

Wilkinson, et al. "Selective 2'-Hydroxyl Acylation Analyzed by Primer Extension (SHAPE): Quantitative RNA Structure Analysis at Single Nucleotide Resolution," Nature Protocols (2006) 1(3):1610-1616.

Xu, et al. "A Dynamic RecA Filament Permits DNA Polymerase-Catalyzed Extension of the Invading strand in Recombination Intermediates," J. Biol. Chem (2002) 277(16):14321-14328.

(56) References Cited

OTHER PUBLICATIONS

Zaghloul, et al. "Optimizing Anti-Gene Oligonucleotide 'Zorro-LNA' for Improved Strand Invasion into Duplex DNA," Nucleic Acids Res (2011) 39(3):1142-1154.
Zhou, et al. "Method to Purify Mitochondrial DNA Directly from Yeast Total DNA," Plasmid (2010) 64:196-199.
Wu, et al. "Target Specificity of the CRISPR-Cas9 System," Quantitative Biology (2014) 2(2):59-70.
International Search Report and Written Opinion dated Nov. 5, 2015 for related PCT/US2015/045885.
Fonfara, et al. "Phylogeny of Cas9 Determines Functional Exchangeability of Dual-RNA and Cas9 Among Orthologous Type II CRISPR-Cas Systems," Nucleic Acids Research 42(4):2577-2590.
Golic "RNA-Guided Nucleases: A New Era for Engineering the Genomes of Model and Nonmodel Organisms," Genetics (2013) 195:303-308.
Zetsche, et al. "Cpf1 is a Single RNA-Guided Endonuclease of a Class 2 CRISPR-Cas System," Cell (2015) 163:759-771.
Extended Search Report dated Mar. 13, 2018 for related EP 15834113.1.
International Preliminary Report on Patentability dated Mar. 2, 2017 for related PCT/US2015/045885.

\* cited by examiner

Target region:

N N N N N N N N N Y Y Y Y Y Y R R Y Y Y Y Y R R Y N N N N N N N N
N N N N N N N N N N Y Y Y Y Y R R R R Y Y Y Y R R R N N N N N N N bis-PNA Clamp 1 Binding Site
bis-PNA Clamp 2 Binding Site bis-PNA Clamp 1: C-terminus-Lys$_2$-Y Y Y Y Y Y-(egl)$_3$-Y Y Y Y Y Y-Lys$_2$-N terminus bis-PNA Clamp 2: C-terminus-Lys$_2$-Y Y Y Y Y Y Y-(egl)$_3$-Y Y Y Y Y Y Y-Lys$_2$-N terminus

Figure 5

SEQUENCE LISTING

<160> NUMBER OF SEQ ID NOS: 10

<210> SEQ ID NO 1
<211> LENGTH: 42
<212> TYPE: RNA
<213> ORGANISM: Artificial Sequence
<220> FEATURE:
<223> OTHER INFORMATION: crRNA #724

<400> SEQUENCE: 1
gucaaucaug cuggccggcg guuuuagagc uaugcuguuu ug         42

<210> SEQ ID NO 2
<211> LENGTH: 42
<212> TYPE: RNA
<213> ORGANISM: Artificial Sequence
<220> FEATURE:
<223> OTHER INFORMATION: crRNA #722

<400> SEQUENCE: 2
uccaagaugg acggccgcuc guuuuagagc uaugcuguuu ug         42

<210> SEQ ID NO 3
<211> LENGTH: 42
<212> TYPE: RNA
<213> ORGANISM: Artificial Sequence
<220> FEATURE:
<223> OTHER INFORMATION: crRNA #723

<400> SEQUENCE: 3
agcgggccca aacucacggu guuuuagagc uaugcuguuu ug         42

<210> SEQ ID NO 4
<211> LENGTH: 42
<212> TYPE: RNA
<213> ORGANISM: Artificial Sequence
<220> FEATURE:
<223> OTHER INFORMATION: crRNA for FMR1

<400> SEQUENCE: 4
agaggccgaa cugggauaac guuuuagagc uaugcuguuu ug         42

<210> SEQ ID NO 5
<211> LENGTH: 42
<212> TYPE: RNA
<213> ORGANISM: Artificial Sequence
<220> FEATURE:
<223> OTHER INFORMATION: crRNA for ALS

<400> SEQUENCE: 5
gcaauuccac cagucgcuag guuuuagagc uaugcuguuu ug         42

<210> SEQ ID NO 6
<211> LENGTH: 42
<212> TYPE: RNA
<213> ORGANISM: Artificial Sequence
<220> FEATURE:
<223> OTHER INFORMATION: crRNA for E. coli dnaE gene

<400> SEQUENCE: 6
aucuucggug cucauguccc guuuuagagc uaugcuguuu ug         42

<210> SEQ ID NO 7
<211> LENGTH: 18
<212> TYPE: DNA
<213> ORGANISM: Artificial Sequence

```
<220> FEATURE:
<223> OTHER INFORMATION: Synthetic construct

<400> SEQUENCE: 7
yyyyyyyyyr ryyyyyyy                                                  18

<210> SEQ ID NO 8
<211> LENGTH: 18
<212> TYPE: DNA
<213> ORGANISM: Artificial Sequence
<220> FEATURE:
<223> OTHER INFORMATION: Synthetic construct

<400> SEQUENCE: 8
rrrrrrryyr rrrrrrrr                                                  18

<210> SEQ ID NO 9
<211> LENGTH: 19
<212> TYPE: DNA
<213> ORGANISM: Artificial Sequence
<220> FEATURE:
<223> OTHER INFORMATION: Synthetic construct

<400> SEQUENCE: 9
tttccttcca gccttcttt                                                 19

<210> SEQ ID NO 10
<211> LENGTH: 19
<212> TYPE: DNA
<213> ORGANISM: Artificial Sequence
<220> FEATURE:
<223> OTHER INFORMATION: Synthetic construct

<400> SEQUENCE: 10
aaagaaggct ggaaggaaa                                                 19
```

COMPOSITIONS AND METHODS FOR ENRICHMENT OF NUCLEIC ACIDS

CROSS-REFERENCE TO RELATED APPLICATIONS

This application is a continuation in part of U.S. patent application Ser. No. 14/830,293, filed Aug. 19, 2015, which claims the benefit of U.S. Provisional Application No. 62/039,319, filed Aug. 19, 2014, both of which are incorporated herein by reference in their entireties for all purposes.

INCORPORATION-BY-REFERENCE OF MATERIAL SUBMITTED BY U.S.P.T.O. eFS-WEB

The instant application contains a Sequence Listing which is being submitted in computer readable form via the United States Patent and Trademark Office eFS-WEB system, and is hereby incorporated by reference in its entirety for all purposes. The txt file submitted herewith contains only 3 KB file (01017802_2018-05-07_SequenceListingUpdated.txt).

BACKGROUND OF THE INVENTION

It is often desirable to selectively isolate molecules present in a low concentration in a sample, e.g., to facilitate analysis of such molecules without the interference of other more prevalent components of the sample. For example, in the analysis of nucleic acid sequences, actively selecting a portion of the sample nucleic acid that comprises a region of interest can allow a researcher to focus their analytical efforts only on those portions of the nucleic acid sample. As such, the resulting "enriched" nucleic acid sample has a much higher proportion of nucleic acids having the region to be analyzed. Further, in some cases the concentration of a particular molecule in a sample is simply too low, rendering analysis impossible without some sort of concentration of the molecule.

Selectively enriching a sample for a molecule of interest can be performed in various ways known to those of skill in the art. For example, affinity tags have been used for purification of specific molecules of interest from a biological sample using an affinity technique. These tags are covalently or non-covalently linked to the molecules of interest. For example, an affinity tag can be incorporated into a protein of interest to form a fusion protein. The affinity tag further binds to an immobile phase, e.g., a substrate or matrix (e.g., within a column). Once bound, the substrate or matrix is washed to remove all unbound components of the sample leaving only those bound via the affinity tag. Often these tags are removable by chemical agents or by enzymatic means, such as proteolysis, which allows for removal of the selected molecules from the substrate or matrix while leaving the affinity tag behind. Once removed, the selected molecules can be further analyzed or otherwise manipulated.

With regards to isolation of specific nucleic acid sequence ("target nucleic acid") in a complex sample (e.g., a genomic DNA sample), various methods are known in the art. Notably, "hybrid capture" methods use a nucleic acid complementary to the sequence or sequences of interest to specifically hybridize to one or more target nucleic acids. However, where a region of interest represents a very small portion of the total sample, hybridization strategies can be difficult and require massive amplification of the original sample to provide enough of the region of interest to be efficiently selected. In some cases, identification of rare mutations within the region of interest is an object of a study, and since amplification strategies are known to introduce a small number of mutations into the resulting amplicons, these amplification-introduced mutations can complicate the identification of the true rare mutations present in the original sample, especially where single-molecule sequencing strategies are utilized. Further, PCR amplification of certain types of sequences, such as highly repetitive regions, is known to produce amplicons having changes in the length of the repeat region as compared to the original nucleic acid, e.g., due to insertion and deletion mutations introduced during the amplification process. Accordingly, is desirable to provide reaction components that provide a way to select one or more regions of interest from a complex sample and isolate them from other molecules in the sample to facilitate their analysis, preferably without requiring amplification. The present invention provides these and other solutions.

BRIEF SUMMARY OF THE INVENTION

Methods are provided for reducing the complexity of a population of nucleic acids prior to performing an analysis of the nucleic acids, e.g., sequence analysis, cloning, amplification, etc. In preferred embodiments, the methods result in a subset of the initial population enriched for a desired region of interest. The methods are particularly useful for analyzing populations having a high degree of complexity, e.g., chromosomal-derived DNA, whole genomic DNA, or mRNA populations. In addition, such methods allow for analysis of pooled samples.

In preferred aspects, methods are provided for enrichment of a target region in a nucleic acid sample that comprise: a) providing a nucleic acid sample comprising a plurality of double-stranded nucleic acid molecules, wherein at least one nucleic acid molecule in the plurality comprises a target region having a first strand comprising a polypurine site and a second strand complementary to the first strand; b) linking at least one stem-loop adapter to at least one end of each of the plurality of double-stranded nucleic acid molecules, wherein the stem-loop adapter is ligated to both strands; c) providing at least one bis-PNA clamp that specifically binds to the polypurine site in the first strand; d) binding the bis-PNA clamp to the polypurine site, thereby displacing a portion of the second strand; e) annealing an oligonucleotide probe to the portion of the second strand displaced by the binding of the bis-PNA clamp to provide a clamp-target-probe complex; f) capturing the clamp-target-probe complex; and g) isolating the clamp-target-probe complex, thereby enriching the target region. In certain embodiments, two stem-loop adapters are linked to each of the plurality of double-stranded nucleic acid molecules such that at each end of each molecule a stem-loop adapter is covalently linked to both strands, and when the strands are denatured the nucleic acid can form a single-stranded circle. When only a single stem-loop adapter is linked to one end, denaturation of the molecule results in a single-stranded linear molecule. In certain preferred embodiments, the binding of at least one, and more typically two, bis-PNA clamp(s) is performed after separating the complementary strands of the double-stranded nucleic acid molecule, preferably by heat denaturation, e.g., at a temperature of about 80° C., typically for about two minutes. Following denaturation, the mixture is quickly cooled to a temperature of about 37° C., or lower, e.g., at a temperature of about 30° C., 25° C., 20° C., 15° C., 10° C., 7° C., or 4° C. The binding is preferably performed at a pH of at least 6.0, and more preferably at a pH above neutral pH, e.g., a pH of about 8.0. In certain preferred embodiments, the oligonucleotide probe comprises a moiety, for example, a detectable label and/or an affinity tag, e.g., a biotin moiety. In specific embodiments, the clamp-target-probe complex is isolated by binding a moiety on the oligonucleotide probe to a solid or semi-solid surface, e.g., a bead, array, column, etc. An exemplary preferred surface is a magnetic bead comprising a moiety that binds the moiety on the oligonucleotide probe. Where the sequence of the target region is to be determined, the target region is removed from the clamp-target-probe complex following isolation to provide a target template to be analyzed in a sequencing reaction, preferably in a single-molecule strategy. For example, a target template can be subjected to nanopore sequencing or a sequencing-by-synthesis methodology, such as SMRT® Sequencing (Pacific Biosciences, Menlo Park, Calif.). In some embodiments, e.g., where the target template comprises the target region flanked by two stem-loop adapters, the sequencing strategy provides redundant sequence information, e.g., at least one read from each strand, and optionally multiple reads from one or both strands. In preferred implementations, at least 1000- to 5000-fold enrichment is achieved by the methods herein.

In certain aspects, a method for enrichment of a target region in a nucleic acid sample is provided that comprises a) providing the nucleic acid sample comprising the target region; b) providing two guide RNAs, wherein a first guide RNA comprises a sequence complementary to a first location within the nucleic acid sample that is 3'-adjacent to the target region and a second guide RNA comprises a sequence complementary to a second location within the nucleic acid sample that is 5'-adjacent to the target region; c) exposing the guide RNAs to Cas9 endonucleases such that each of the guide RNAs is bound to one of the Cas9 endonucleases to form a sgRNA-Cas9 complex; d) combining the sgRNA-Cas9 complex with the nucleic acid sample under conditions that promote binding of the sgRNA-Cas9 complex to the nucleic acid sample at the first location and the second location; e) subjecting the nucleic acid sample to Cas9 cleavage, wherein the Cas9 endonucleases cleave the nucleic acid sample at the first location and the second location; f) linking stem-loop adapters to all double-stranded ends in the nucleic acid sample after the Cas9 cleavage to form adapter-ligated fragments; and g) selecting the adapter-ligated fragments (i) having an adapter at both termini and (ii) having a size consistent with the known size of the target region, thereby enriching the nucleic acid sample for the target region. In certain embodiments, at least one of the stem-loop adapters linked to the target region comprises a primer binding site complementary to a nucleic acid primer. The nucleic acid primer may be complementary to a binding site entirely within the stem-loop adapter, or may be partially complementary to a portion of the target region immediately adjacent to the primer binding site in the stem-loop adapter. The adapter-linked fragments selected in g) are optionally subjected to a single-molecule sequencing reaction, e.g., a sequencing-by-synthesis reaction, which, in preferred embodiments, can generate redundant sequence information from single molecules of the adapter-ligated fragments selected in g).

In various embodiments described herein, enriched nucleic acids are subjected to one or more further analyses, e.g., sequencing reactions, a haplotype analysis, diagnostic tests, screening tests, prognostic tests, barcoding, or multiplexed analyses. The target region(s) can comprise any region(s) of interest to the practitioner of the instant invention, e.g., a full-length repeat region from a genomic sample, a promoter region controlling expression of a gene of interest (which may or may not comprising a full-length repeat region), target regions from multiple chromosomes, target regions from homologous chromosomes, imprinted genes, splice isoforms, heterochromatic regions, euchromatic regions, genic regions, non-genic regions, regulatory regions, cloned nucleic acids, native nucleic acids, amplified nucleic acids, full haplotypes for a gene of interest, full alleles for a repeat expansion region, or nucleic acids from multiple sources, e.g., different genes, tissues, individual (e.g., cases and controls), barcoded nucleic acids, full-length genes and the corresponding mRNA or cDNA sequences, and the like.

In certain aspects, methods for enrichment of a target region in a DNA library are provided. In some embodiments, such methods comprise providing a DNA library of double-stranded fragments with hairpin adapters on both ends, wherein one or more of the double-stranded fragments are target fragments that comprise the target region; providing an RNA-endonuclease complex, wherein at least one targeting RNA in the RNA-endonuclease complex comprises a sequence complementary to a first location, which is present only once within at least one of the target fragments, wherein the first location is not within the target region; combining the RNA-endonuclease complex with the DNA library in a reaction mixture under conditions that promote binding of the RNA-endonuclease complex to the first location in the target fragments; subjecting the DNA library to Cas9 cleavage, wherein a Cas9 endonuclease in the RNA-endonuclease complex cleaves the target fragments at the first location; linking stem-loop adapters to all double-stranded ends in the nucleic acid sample after the Cas9 cleavage to form asymmetric-adapter-ligated fragments, wherein the stem-loop adapters have a different sequence than the hairpin adapters; and isolating the asymmetric-adapter-ligated fragments from other fragments in the reaction mixture that are not linked to the stem-loop adapters. One or both of the hairpin adapters and/or stem-loop adapters can comprise various elements, such as a primer binding site complementary to a sequencing primer, an oligonucleotide binding site complementary to an oligonucleotide linked to a solid surface (e.g., a bead, array, column, etc.), a restriction site, an affinity tag, a barcode, or one or more modifications, e.g., methylated bases, PNA (peptide nucleic acid) nucleotides, LNA (locked nucleic acid) nucleotides, 2'-O-methyl-modified nucleotides, and the like. In certain embodiments, the method further comprises subjecting the asymmetric-adapter-ligated fragments isolated in g) to a single-molecule sequencing reaction, e.g., a sequencing-by-synthesis reaction or a nanopore sequencing reaction. In certain preferred embodiments, the single-molecule sequencing reaction generates redundant sequence information from single molecules of the selected adapter-ligated fragments. In some embodiments, the method further comprises amplifying the isolated asymmetric-adapter-ligated fragments. Optionally, the DNA library can be a whole-genome DNA library, a library comprising only a portion of a genome, or a cDNA library, and optionally the nucleic acids in the DNA library are not amplified prior to the enrichment. The target region can be a repeat region, e.g., comprising at least 10, 20, 30, 40, 50, 75, 100, or more repeats. The target region can comprise a prognostic or diagnostic marker, an imprinted gene, a full-length gene, and/or a pseudogene. In some cases, the target region comprises epigenetic modifications, e.g., methylated or hydroxymethylated bases. In certain embodiments, the target region is a repeat region comprising sequence interruptions, and the isolated asymmetric-adapter-ligated fragments are sequenced using a technology that can both determine how many repeats are in the repeat region and can identify each of the sequence interruptions in the repeat region. In other embodiments, the target region is a repeat region comprising epigenetic modifications, and the isolated asymmetric-adapter-ligated fragments are sequenced using a single-molecule sequencing technology that can detect both a nucleotide sequence and the epigenetic modifications during a single sequencing reaction. Often, the binding site (first location) is located away from the target region, e.g., at least 100, 150, 200, 250, 300 or more base pairs away from the target region. Preferably, the RNA-endonuclease complex associates with the target fragments such that the 3' end of the targeting RNA is nearer to the target region than the 5' end. Optionally, no end repair is performed following the Cas9 cleavage and prior to the linking said stem-loop adapters. In some embodiments, the RNA-endonuclease complex comprises a single targeting RNA, while in other embodiments the RNA-endonuclease complex comprises two targeting RNAs. In certain preferred embodiments, the RNA-endonuclease complex comprises a site-specific endonuclease, e.g., Cas9 endonuclease or Cpf1 endonuclease.

BRIEF SUMMARY OF THE DRAWINGS

FIG. 5 provides a graphical illustration of the generic structure of a target region and two bis-PNA clamps (SEQ ID NO: 7 in the top strand and complementary SEQ ID NO: 8 in the bottom strand).

DETAILED DESCRIPTION

I. General

Figure 1:
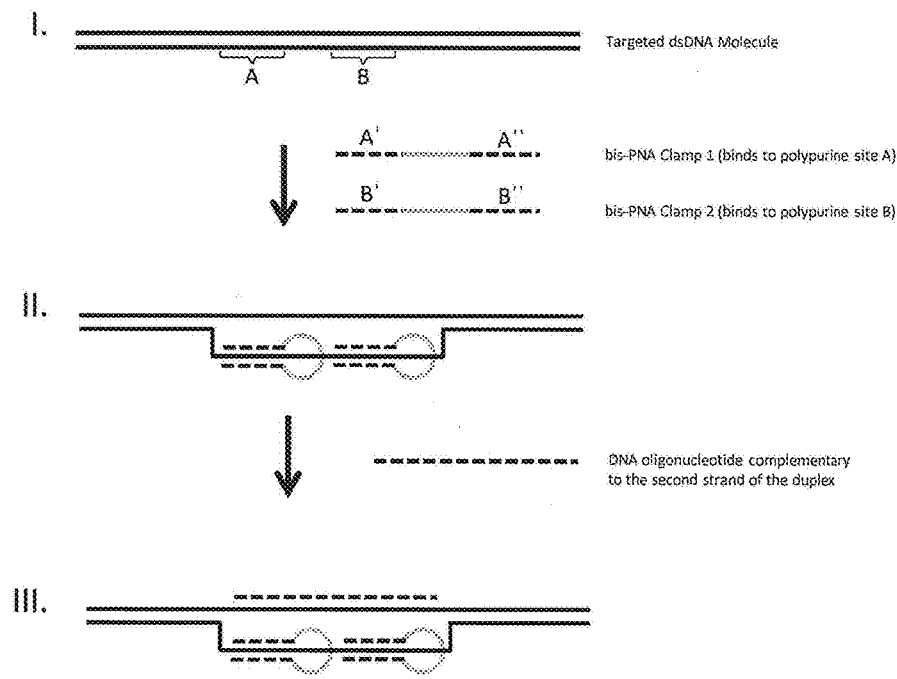
FIG. 1 provides an illustrative embodiment of bis-PNA oligonucleotides bound to a duplex region and subsequent binding of an oligonucleotide probe.

Unless defined otherwise, all technical and scientific terms used herein have the same meaning as commonly understood by one of ordinary skill in the art to which this invention belongs. Note that as used herein and in the appended claims, the singular forms "a," "an," and "the" include plural referents unless the context clearly dictates otherwise. Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention. Although certain preferred embodiments are described in detail herein, one of ordinary skill in the art will readily recognize the applicability of the invention in other related embodiments, e.g., enrichment of target molecules other than nucleic acid molecules. Further, the enrichment methods herein can be used in combination with each other, or in combination with methods known to the ordinary practitioner, including but not limited to those described in: Huang, et al. (2008) SPIE 7269: A1-11; Mertes, et al. (2011) Briefings in Functional Genomics 10(6):374-386; Jordon, et al. (2002) Proc. Natl. Acad. Sci. USA 99(5):2942-7; Callow, et al. (2004) Nucl. Ac. Res. 32(2):e21; U.S. Patent Publication Nos. 20030059955, 20050100911, 20070003938, 20090162845, 20100286070, 20130303385, 20140179564, and 20140134610, U.S. Pat. No. 6,361,947; U.S. patent application Ser. Nos. 14/069,067 and 14/068,293, both filed Oct. 31, 2013; and U.S. Provisional Patent Application Nos. 61/799,237 (filed Mar. 15, 2013) and 61/952,022 (filed Mar. 12, 2014), all of which are incorporated herein by reference in their entireties for all purposes.

Enriched compositions of the invention find particular utility in nucleic acid sequencing applications, especially where a region of interest is a minority species within a complex sample (e.g., genome). In such cases, the majority of sequencing data generated by sequencing the entire complex sample is not relevant to determining the sequence of the region of interest. As such, the value of the sequencing data generated is substantially increased where a majority of the complex sample is removed prior to sequencing, but where the region of interest is selectively retained. Sequencing after such an enrichment results in a higher proportion of the resulting sequence data being relevant to determining the sequence of the region of interest, since a higher percentage of the sequence reads are generated from the region of interest, e.g., by single-molecule sequencing. Many other applications will benefit from the enrichment strategies provided herein, e.g., cloning, amplification, diagnostics, prognostics, theranostics, genetic screening, and the like. In preferred embodiments, the enriched nucleic acids produced by the methods herein are used in single-molecule, real-time sequencing reaction, e.g., SMRT® Sequencing from Pacific Biosciences, Menlo Park, Calif. The use of other sequencing technologies is also contemplated, e.g., nanopore sequencing (e.g., from Oxford Nanopore or Genia), Solexa® sequencing (Illumina), tSMS™ sequencing (Helicos), Ion Torrent® sequencing (Life Technologies), pyrosequencing (e.g., from Roche/454), SOLiD® sequencing (Life Technologies), microarray sequencing (e.g., from Affymetrix), Sanger sequencing, etc. Preferably, the sequencing method is capable of sequencing long template molecules, e.g., >1000-10,000 bases or more. Preferably, the sequencing method is capable of generating long sequence reads from a single template molecule, e.g., >1000-10,000 bases or more, e.g., without having to assemble shorter reads to construct "stitched-together" long reads. Preferably, long reads generated by the sequencing method are contiguous reads having base calls over the full length of the reads and lacking polynucleotide gaps (e.g., of five or more consecutive nucleotides) where bases could not be called. Preferably the sequencing method is capable of detecting base modifications during a sequencing reaction, e.g., by monitoring the kinetics of the sequencing reaction. More information on detection of modifications during sequencing reactions is provided in detail, e.g., in International Application Publication No. WO 2012/065043 A2 and U.S. Provisional Application Nos. 61/721,206, filed Nov. 1, 2012, both of which are incorporated herein by reference in their entireties for all purposes. Preferably the sequencing method can analyze the sequence of a single template molecule, e.g., in real time during an ongoing sequencing reaction. Preferably the sequencing method is a processive method that does not require buffer exchanges or washing between subsequent base detections, e.g., SMRT® Sequencing or nanopore sequencing. As used herein, analyzing a single template molecule is different from analyzing a patch or feature having multiple identical template sequences that are sequenced as an ensemble, since such an ensemble method generates a single sequence read that corresponds to the set of identical template sequences rather than a single sequence read that corresponds to a single template molecule. Systems that analyze patches or features of identical nucleic acids in this way are not able to generate a single read from a single molecule.

The present invention is directed to methods for analyzing nucleic acid samples and preferred compositions and methods for performing such analysis. These methods find particular utility when analyzing a small select portion ("target" or "target region") of a complex sample, e.g., a single genomic region or locus, e.g., repeat region, from a sample comprising the entire genome of an organism. The target region may be any region of interest within a sample nucleic acid, e.g., a gene, gene complex, pseudogene, regulatory region, highly repetitive region, polymorphic region, transposon, or portions thereof. In some cases, a repeat region has at least 5, 10, 20, 30, 40, 50, 75, 100 or more repeats, e.g., dinucleotide or trinucleotide repeats. In some aspects, a set of loci are selected to be enriched, e.g., where the set of loci are structurally or functionally related. Such target nucleic acid molecules can comprise both natural and non-natural, artificial, or non-canonical nucleotides including, but not limited to, DNA, RNA, BNA (bridged nucleic acid), LNA (locked nucleic acid), PNA (peptide nucleic acid), morpholino nucleic acid, glycol nucleic acid, threose nucleic acid, and mimetics and combinations thereof.

The starting population of nucleic acids can be from any source, e.g., a whole genome, a collection of chromosomes, a single chromosome, or one or more regions from one or more chromosomes, and may be purified directly from the biological source or from a laboratory source, e.g., a nucleic acid library. The nucleic acids can be obtained from the same individual, which can be a human or other species (e.g., plant, bacteria, fungi, algae, archaea, etc.), or from different individuals of the same species, or different individuals of different species. For example, the nucleic acids may be from a metagenomic sample, e.g. an environmental or intestinal sample. The starting population of nucleic acids can be derived from cloned DNA (e.g., BACs, YACs, PACs, etc.), RNA (e.g., mRNA, tRNA, rRNA, ribozymes, etc.), cDNA, or a combination thereof. In specific examples, the nucleic acids are from a whole genome DNA library, a partial genome DNA library, or a cDNA library.

In certain preferred embodiments, the starting population of nucleic acids is either native nucleic acids, e.g., genomic DNA, or amplified nucleic acids, such as those generated by PCR, isothermal amplification, or whole-genome amplification (WGA), for example, a rolling-circle method, e.g., using a Phi29 polymerase. Genomic nucleic acids can be collected from various sources including, but not limited to, cell lines/cultures, whole blood, semen, saliva, tears, urine, fecal material, sweat, buccal cells, skin, hair, biopsies, environmental sources. A genomic DNA sample is preferably isolated from RNA (by RNaseA+T1-treatment) and ssDNA. Methods for generating a nucleic acid sample, e.g., from one of the sources listed above, are known and routine to those of ordinary skill in the art. Typically, they involve cell lysis, stabilization and protection of the nucleic acids (e.g., from nuclease digestion), isolation of the nucleic acids from other components (e.g., proteins, carbohydrates, lipids, etc.) of the original sample, and optional fragmentation, e.g., by chemical, enzymatic (e.g., with one or more restriction enzymes), or mechanical means (e.g., sonication or shearing). The fragmentation can involve multiple strategies (e.g., staged or simultaneous fragmentation using multiple different strategies, enzymes, etc.) serves to reduce the size of the nucleic acids, which can facilitate subsequent analyses, e.g., by providing the nucleic acids with or modifiable to have termini appropriate for subsequent steps in the analysis, e.g., cloning, ligation of adapters, circularization, and the like. For example, the fragmentation can comprise a restriction enzyme digestion using one or more restriction enzymes, e.g., type II or type IIs. The digestions can optionally be followed by a treatment to provide ends of a specific conformation, e.g., blunt, 3'-overhangs, or 5'-overhangs. In certain embodiments, the restriction digestion does not cleave within the target region, thereby excising a fragment comprising the entire target region (one target fragment). In other embodiments, the restriction digestion cleaves within the target region so that multiple fragments each comprise a portion of the target region (multiple target fragments). The restriction digest may provide the same or different termini at the ends of a target fragment comprising the target region. For example, both ends may comprise blunt ends, 3' overhangs, or 5' overhangs. In some embodiments, the restriction digestion provides target fragments having different termini at each end, e.g., different overhang sequences or one blunt end and one overhang. This facilitates differential treatment of the two ends, e.g., attachment of different adapter sequences at each end.

In certain aspects, a sample comprising a mixture of both target and non-target nucleic acids is subjected to additional treatment prior to enriching for the target nucleic acids. In certain embodiments, the treatment serves to facilitate the subsequent enrichment. For example, sample nucleic acids can be further fragmented, amplified, or adapters can be added to some or all nucleic acids in the sample prior to enriching for the target nucleic acids. In some embodiments, the ends of fragments are subjected to repair, such as removal of overhang sequences, prior to further manipulations, e.g., adapter ligation, amplification, cloning, etc. In certain preferred embodiments, fragments of a sample nucleic acid are ligated to stem-loop adapters (also sometimes referred to as hairpin adapters). These adapters may be ligated to all fragments, or only some fragments, e.g., those having at least a portion of the target region.

In certain preferred embodiments, a sample set of nucleic acids is not amplified or cloned prior to enrichment and/or further analysis, e.g., sequence analysis. For certain applications, e.g., where epigenetic modifications are being analyzed (e.g., 5-mC, 6-mA, etc.), amplification generates amplicons that lack the modification that was present in the original sample set, e.g., where a modified base has the same binding specificity to a complementary nucleotide as does an unmodified base. For example, C, 5-MeC, and 5-hmC are all complementary to G. As such, amplification of a template nucleic acid having one of these modifications using unmodified nucleoside polyphosphates will generate amplicons lacking the modification found in the original template. Further, as noted above, amplification can introduce variations in the amplicons (e.g., via errors during PCR) such that their nucleotide sequence is not reflective of the original sample. As such, in certain embodiments, nucleic acids to be enriched and/or otherwise analyzed are not amplified in the methods herein. Similarly, cloning of a target region into another organism often does not maintain modifications present in the original sample nucleic acid, so in preferred embodiments nucleic acids to be enriched and/or otherwise analyzed are typically not cloned in the methods herein. Rather, they are enriched directly from the original nucleic acid sample.

However, the enrichment of "native" nucleic acid targets, for sequence determination and base modification detection using single-molecule sequencing techniques (e.g., SMRT Sequencing, nanopore sequencing, etc.), sometimes requires ≥10 micrograms of human gDNA, which only has about 2-6 picograms of the targeted DNA fragment. For those samples when only a limited quantity of gDNA (sub-microgram) are available and base modification detection is not needed, a few nanograms of gDNA can be amplified, e.g. using PCR or whole-genome linear amplification. For example, a commercial kit (e.g., from Qiagen) can generate 20-50 µg of amplified nucleic acids, which can then be used in the targeted enrichment methods provided herein. However, since any base modifications are not typically preserved in the amplified nucleic acid, the enriched templates derived from amplified DNA cannot be used for kinetic-based base-modification detection by SMRT Sequencing, although other known methods for detection methylated bases can be used with such amplification, e.g., bisulfite sequencing, TAB-seq, and oxBS-Seq methods.

In certain aspects, the methods enrich complex nucleic acid samples for target nucleic acid molecules of interest. In certain embodiments, the methods herein use bis-PNA oligonucleotides to open the duplex within or adjacent to a target region for which enrichment is desired. At least one and preferably two or more bis-PNA oligonucleotides or "clamps" open the duplex in at least a portion of the target region by binding to one strand of the duplex, thereby displacing the opposite strand. The displaced strand is then free to bind to an oligonucleotide probe linked to a moiety, e.g., an affinity tag that can be used to isolate the target region from the complex nucleic acid sample. FIG. 1 provides an illustrative embodiment of how bis-PNA oligonucleotide clamps can open a duplex region to allow binding of oligonucleotide probes. Briefly, a double-stranded DNA molecule having a target region is illustrated (I), where the target region comprises two specific sequences, A and B. Two bis-PNA clamps are added, with clamp 1 having specificity for sequence A and clamp 2 having specificity for sequence B. Each clamp comprises two terminal portions that align together and form a stable triple helix with the specific sequence in the duplex DNA molecule, as shown in II. The formation of the triple helix displaces the opposite strand of the duplex, which can then be annealed to a DNA oligonucleotide complementary thereto. The presence of multiple bis-PNA clamps in relatively short proximity on the duplex molecule is preferred because this orientation allows a longer portion of the opposite strand to be displaced, and a longer oligonucleotide can be annealed. Part III illustrates a duplex bound by two bis-PNA clamps and a complementary DNA oligonucleotide.

In certain embodiments, the complementary oligonucleotide that is annealed to the strand displaced by the bis-PNA clamps is linked to a moiety that can be used to capture the duplex and, optionally, isolate it from other nucleic acids that do not comprise the target region. For example, an affinity tag can be linked to the oligonucleotide and subsequently used to capture the nucleic acids in a mixture that comprise the target region. In certain preferred embodiments, a biotin molecule is linked to the oligonucleotide, e.g., at the 3'- or 5'-terminal region and after annealing the nucleic acid mixture is exposed to streptavidin, which is linked to a solid or semisolid surface, such as a magnetic bead, chromatography column, gel matrix, or planar array. It will be clear to the ordinary artisan that many other capture moieties that are well known and routinely used in the art can be used in the place of the biotin and streptavidin. In other embodiments, the complementary oligonucleotide comprises a non-complementary terminal portion that can hybridize to an oligonucleotide linked to a solid surface, such as the surface of a bead or microarray. In yet further embodiments, the complementary oligonucleotide can also be linked to a detectable label, e.g., to provide an optical method for determining a quantity of target region isolated. Optionally, the complementary oligonucleotide can be used as a primer in a subsequent amplification, pre-extension, or sequencing reaction, as detailed elsewhere herein.

This strategy, described in detail below, can be used to capture a single target region, or can be multiplexed to capture multiple, different target regions. In preferred embodiments, at least a 10-fold, 25-fold, 100-fold, 200-fold, 300-fold, 500-fold, 700-fold, 1000-fold, 10,000-fold, or greater molar enrichment of the target region of interest is achieved relative to the concentration of the target region in the original sample. In some embodiments, only fewer than 500, 400, 300, 200, 100, 50, or 20 loci are present or represented in a final, enriched mixture where the original, non-enriched mixture comprised greater than 1000, 10,000, 100,000, or 1,000,000 fragments of a complex nucleic acid sample, which potentially comprises thousands, millions, or more different loci.

In other aspects of the invention, certain methods herein use at least one "single guide RNA" (sgRNA) and Cas9 endonuclease to capture a target region (or multiple target regions) within double-stranded sample DNA, e.g., as described in Jinek, et al. (Science 337:816-821 (2012); incorporated herein by reference in its entirety). Each sgRNA is typically designed to have a 10-20 by "guide region" that is complementary to a "complementary region" within the double-stranded DNA, and a "scaffold region," which is required for binding of the Cas9 enzyme, as further described below. In some embodiments, the methods use at least one combination of two RNA molecules (rather than an sgRNA) to target the Cas9 endonuclease to a specific position in or near a target region. For example, the complex of the two RNA molecules directs the Cas9 endonuclease to the location in the nucleic acid that will be cut, e.g., the crRNA:tracrRNA complex described below. For ease of discussion, an RNA molecule that forms a complex with a Cas9 endonuclease to facilitate targeted cleavage of a nucleic acid can be referred to as a "targeting RNA," and such targeting RNAs include sgRNAs, crRNAs, and tracrRNAs. Similarly, a complex of Cas9 with a one or more targeting RNAs will generally be referred to as an RNA-Cas9 complex. The number of targeting RNAs is dependent upon how many unique sites to which the Cas9 endonuclease must be targeted and whether a single- or double-targeting RNA strategy will be used. In certain embodiments, the enrichment of a target region requires only a single Cas9 cleavage, e.g., where only one cleavage is necessary for the enrichment strategy. In other embodiments, the enrichment requires two Cas9 cleavages, e.g., where the target region is to be excised from the sample nucleic acid in its entirety. In further embodiments, the enrichment may require more than two Cas9 cleavages, e.g., where the target region is extremely large and must be enriched in pieces rather than as one fragment. Optionally, the Cas9 cleavage(s) can be combined with other fragmentations, e.g., where a fragment to be enriched is cleaved on one side by Cas9 and on the other side by another endonuclease, e.g., a type II or type IIs restriction endonuclease, or other site-specific cleavage agent.

In preferred embodiments, at least a 10-fold, 25-fold, 100-fold, 200-fold, 300-fold, 500-fold, 700-fold, 1000-fold, 10,000-fold, or greater molar enrichment of the target region of interest is achieved relative to the concentration of the target region in the original sample. In some embodiments, only fewer than 1000, 500, 400, 300, 200, 100, 50, or 20 loci are present or represented in a final, enriched mixture where the original, non-enriched mixture comprised greater than 1000, 10,000, 100,000, or 1,000,000 fragments of a complex nucleic acid sample, which potentially comprises thousands, millions, or more different loci.

In bacteria, the RNA-guided CRISPR-Cas9 system functions as a heritable defense mechanism to recognize and destroy foreign DNA. ssRNA complementary to the foreign DNA (pre-crRNA) and transactivating crRNA (tracrRNA) are transcribed from the CRISPR locus. The tracrRNA hybridizes to the repeat regions of the pre-crRNA and mediates the processing of pre-crRNA into mature crRNA to form the mature crRNA:tracrRNA complex, which directs Cas9 to the target DNA via Wastson-Crick base-pairing between the spacer on the crRNA and the protospacer on the target DNA next to the protospacer adjacent motif (PAM), described further infra. The crRNA hybridizes to the "complementary strand" of the foreign DNA, thereby bringing the Cas9 endonuclease to the foreign DNA. The Cas9 endonuclease has two separate nuclease domains: the HNH nuclease domain cleaves the strand complementary to the crRNA, and the RuvC-like nuclease cleaves the opposite strand of the foreign DNA. In doing so, a double-strand break is introduced into the foreign DNA, inactivating it and protecting the bacterium. Another requirement for cleavage is that the crRNA must bind to the foreign DNA adjacent to a PAM (protospacer adjacent motif), such that the PAM is located within the foreign DNA next to the 5'-end of the complementary region of the foreign DNA. The PAM comprises 2-5 base pairs of conserved sequence, depending on the type of CRISPR-Cas system and the organism, and a variable sequence of up to four base pairs that separates the conserved sequence of the PAM from the portion of the complementary strand hybridized to the crRNA. The double-strand break introduced by the nuclease activities of Cas9 is predominantly a blunt cut, but the position of the cut on the noncomplementary strand can be altered by changing the length of a linker (nonconserved sequence) between the PAM and the region of the foreign DNA complementary to the crRNA. Additional details and discussion of CRISPR-Cas9 systems in various bacteria and for genome editing are known in the field, e.g., see Fu, et al. (2014) Nature Biotechnology, "Improving CRISPR-Cas nuclease specificity using truncated guide RNAs," doi:10.1038/nbt.2808; Mali, et al. (2013) Science 339(6121): 823-6; Mali, et al. (2013) Nature Methods 10(10):957-963; Mali, et al. (2013) Nature Biotechnology 31:833-838; Hsu, et al. (2013) Nature Biotechnology 31(9):827-832; Jinek, et al. (2012) Science 337(6096): 816-21; Jinek, et al. (2013) eLife 2: e00471; Hwang, et al. (2013) Nat. Biotechnology 31(3): 227-9; Jiang, et al. (2013) Nat. Biotechnology 31(3): 233-9; Cong, et al. (2013) Science 339(6121): 819-23; Jiang, et al. (2013) Nucleic Acids Research 41(20): e188; Golic, K. (2013) Genetics 195: 303-308; Ran, et al. (2013) Nature Protocols 8(11): 2281-2308; Chen, et al. (2014) J. Biol. Chem., "Cut Site Selection by the Two Nuclease Domains of the Cas9 RNA-guided Endonuclease," doi:10.1074/jbc.M113.539726; U.S. Patent Publication Nos. 20140127752, 20140356867, 20140357523, 20140315985, 20140302563, 20140272959, 20140068797, 20140038241, 20140242664, 20140127752, and 20140038241; and U.S. Pat. No. 8,906,616, all of which are incorporated herein by reference in their entireties for all purposes.

Figure 2:
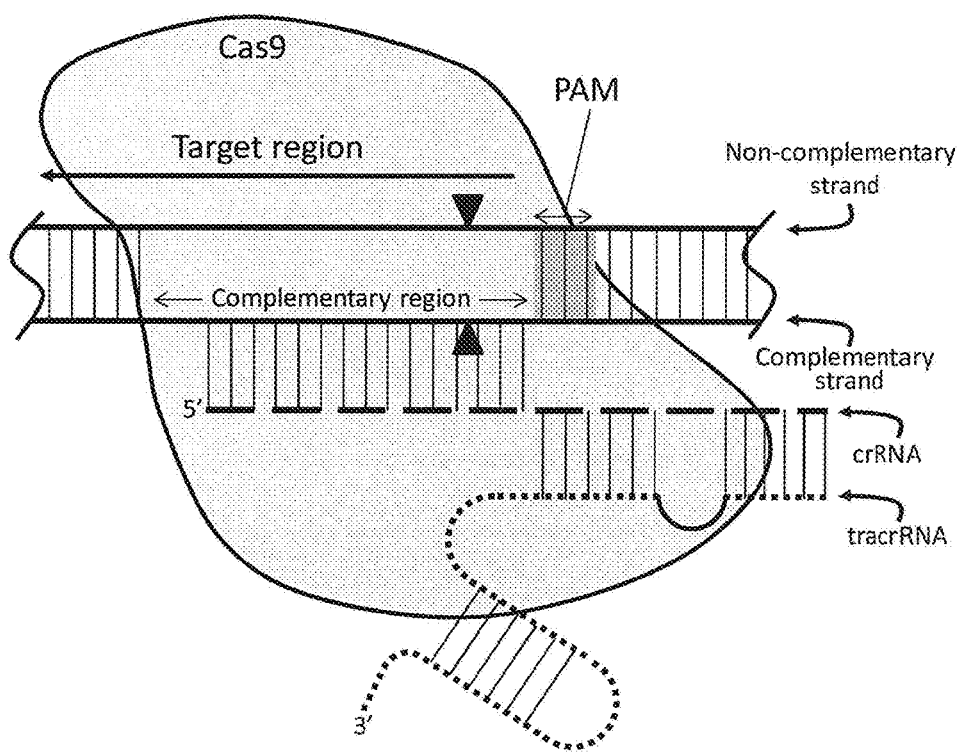
FIG. 2 schematically illustrates the general structure of a crRNA:tracrRNA-Cas9 endonuclease complex bound to a sample dsDNA molecule.

In certain preferred embodiments, a crRNA:tracrRNA complex is used to recruit Cas9 endonuclease to a cleavage site in or near a target region in a sample nucleic acid. FIG. 2 provides a schematic of a crRNA:tracrRNA-Cas9 endonuclease complex bound to a complementary region in a dsDNA. The target region within the dsDNA extends leftward, as indicated by the arrow, and the wavy lines at the ends of the dsDNA are intended to mean that the dsDNA is longer than the portion shown here, extending in both directions. The complementary strand of the dsDNA is the strand comprising the complementary region that hybridizes to the crRNA (shown as a dashed line). The non-complementary strand of the dsDNA is also indicated, as is the tracrRNA (shown as a dotted line). The vertical lines represent base pairing between two strands, whether they are DNA, RNA, or a DNA/RNA hybrid where the guide region is bound to the complementary region. The number of vertical lines is not intended to show any specific number of base pairs, but rather to generally indicate a region of base pairing. In this illustrative embodiment, the PAM is three nucleotides in length, and the cleavage (A) of the dsDNA by Cas9 occurs within the complementary region between the third and fourth nucleotide outside of the PAM.

Figure 3:
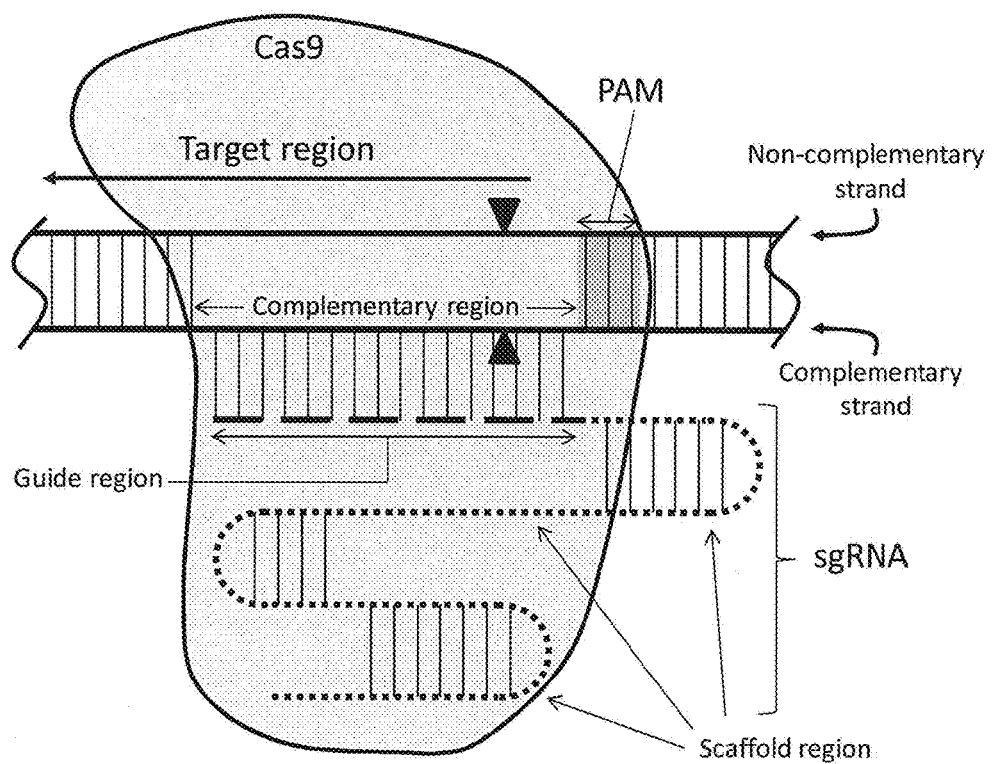
FIG. 3 schematically illustrates the general structure of a sgRNA-Cas9 endonuclease complex bound to a sample dsDNA molecule.

In other preferred embodiments, rather than using separate crRNA and tracrRNA molecules in a crRNA:tracrRNA complex, the methods use a single RNA molecule that comprises both a crRNA and tracrRNA region, termed an sgRNA. FIG. 3 provides a schematic of a sgRNA-Cas9 endonuclease complex bound to a complementary region in a dsDNA. The target region within the dsDNA extends leftward, as indicated by the arrow, and the wavy lines at the ends of the dsDNA are intended to mean that the dsDNA is longer than the portion shown here, extending in both directions. The complementary strand of the dsDNA is the strand comprising the complementary region that hybridizes to the guide region (shown as a dashed line) of the sgRNA. The non-complementary strand of the dsDNA is also indicated, as is the scaffold region of the sgRNA (shown as a dotted line). The vertical lines represent base pairing between two strands, whether they are DNA, RNA, or a DNA/RNA hybrid where the guide region is bound to the complementary region. The number of vertical lines is not intended to show any specific number of base pairs, but rather to generally indicate a region of base pairing. In this illustrative embodiment, the PAM is three nucleotides in length, and the cleavage (A) of the dsDNA by Cas9 occurs within the complementary region between the third and fourth nucleotide outside of the PAM.

In certain embodiments, the Cas9 endonuclease cleaves the double-stranded sample DNA to excise the target region. Preferably, two cleavages are made, one on each end of the target region. For example, two sgRNA-Cas9 complexes, each having a guide region complementary to a different end of the target region, can be used to cleave the target region at each end, thereby excising the target region from the sample DNA. Alternatively, one cleavage can be performed by Cas9 while the second is made by an endonuclease other than Cas9, either before, during, or after the Cas9 cleavage reaction. For example, if the sample nucleic acid is subjected to a restriction digest that cleaves proximal to one end of the target region, then subsequent digestion with Cas9 can cleave proximal to the other end of the target region, thereby providing a target fragment having a Cas9 cleavage site at only one end. Optionally, the fragments generated by the initial restriction digest can be further modified prior to the Cas9 cleavage, e.g., subjected to end repair, ligated to adapters, subjected to purification methods and/or size selection, barcoded, and the like. The resulting excised target region will have a Cas9 cleavage site at one end and the other end will have the modifications introduced prior to Cas9 cleavage, e.g., adapter or barcode. Subsequently, the end produced by Cas9 cleavage can also be modified by addition of adapters and/or barcodes, and the target fragments can optionally be subjected to purification and/or size selection prior to cloning, amplification, sequencing, or other analysis.

Isolation of an excised target region from the rest of the sample DNA can be accomplished using methods known in the art. For example, a size-selection can be performed to separate nucleic acids having a size consistent with the expected size of the excised target region from the rest of the sample DNA, e.g., by gel purification, density gradient separation, spin-column purification, chromatography, the BluePippin™ system, and the like. Optionally or additionally, an RNA-Cas9 complex can comprise a tag or other moiety for retaining the target-probe complex after hybridization, in the presence or absence of Cas9 cleavage. For example, the scaffold region of an sgRNA or a tracrRNA may comprise a biotin moiety, a homopolymer region, or other affinity tag that can be captured prior to RNA-Cas9 dissociation, e.g., by a binding partner linked to a solid or semi-solid surface, such as a bead, array, column, and the like. In other embodiments, the excised target fragment comprises an affinity tag, e.g., in an linked adapter.

As noted above, the ends of the target regions that are enriched by the methods herein are ligated to one or more adapter sequences, e.g., barcode, stem-loop and/or hairpin adapters. For example, where two Cas9 cleavage events are used to excise a target region, ligation after Cas9 digestion can link adapter sequences to one or both Cas9 cleavage sites, and such ligation preferably selectively links the adapter sequences to the Cas9 cleavage sites and not to other nucleic acids ends in the sample. Alternatively, sample nucleic acids can be ligated to adapter sequences prior to Cas9 digestion such that following Cas9 digestion the fragments having a Cas9 cleavage site at one end also have a defined adapter sequence at the opposite end. This provides an asymmetry that can be useful in many applications, as further discussed below. In some embodiments, a target fragment having a Cas9 cleavage site on only one end is ligated to an adapter sequence specific for the Cas9 cleavage site to generate a target fragment having a first adapter sequence at the Cas9 cleavage site and, optionally, a second adapter sequence at the opposite end. These adapter sequences, whether symmetric or asymmetric, can be useful in subsequent steps or further analysis. For example, where the adapter sequences comprise a primer binding site, the adapter-flanked target regions can be subjected to a sequencing-by-synthesis reaction to determine the nucleotide sequence of the target region. Barcoded adapter sequences can provide information about the sample from which the fragment was enriched, which can allow multiplexing of enriched fragments during subsequent analysis. Adapter sequences can also comprise various elements, such as a primer binding sites complementary to a sequencing primer, oligonucleotide binding sites complementary to an oligonucleotide linked to a solid surface (e.g., a bead, array, column, etc.), restriction sites, an affinity tags, or one or more modifications, e.g., methylated bases, PNA (peptide nucleic acid) nucleotides, LNA (locked nucleic acid) nucleotides, 2'-O-methyl-modified nucleotides, and the like.

Further, the ligation of hairpin adapters onto both ends of the target region can provide a sequencing template that comprises both the complementary and non-complementary strands of the target region in a single-stranded circular construct that can be repeatedly sequenced to provide redundant sequencing information from both strands. For single-molecule sequencing reactions, e.g., SMRT® Sequencing from Pacific Biosciences, where sequence data is generated from a single template molecule, statistical analysis of the redundant information is used to generate a consensus sequence for the target region from the single sequencing template. Further details about redundant sequencing and circular sequencing templates are provided, e.g., in U.S. Pat. Nos. 7,476,503 and 8,153,375, both of which are incorporated herein by reference in their entireties for all purposes. Further, the ligation of hairpin adapters onto only one end of the target region provides a sequencing template that comprises both the complementary and non-complementary strands of the target region in a single-stranded linear construct that can be sequenced to provide a sequence read from each strand. Such a template is particularly beneficial in sequencing technologies in which a single-stranded linear template is preferred, e.g., in sequencing technologies that use a nanopore-based sensor, which have been described at length in the art and are currently being developed by several companies, including Oxford Nanopore and Genia. However, the use of template having stem-loop adapters at both ends are also contemplated for sequencing in a nanopore-based method, e.g., where the single-stranded circle produced by separating the complementary strands is used as a template for rolling-circle replication, e.g., where the nascent strand or the released phosphate groups are directed to or through the nanopore.

II. Methods Utilizing Bis-PNA Clamps to Enrich/Isolate Target Regions

As described briefly above, in certain preferred embodiments of the methods a mixed population of nucleic acids is enriched for a region of interest or "target region" using bis-PNA clamps and a tagged oligonucleotide that is complementary to at least a portion of the target region. In certain aspects, the methods herein provide improvements to methods disclosed previously, e.g., in U.S. Pat. No. 6,596, 486 and Demidov, et al. (2000) Curr. Issues Mol. Biol. 2(1):31-35, both of which are incorporated herein by reference in their entireties for all purposes. The methods described herein achieve more specific bis-PNA clamp binding, and enhance the stability of the tagged oligonucleotide annealed to the target region as compared to the previous methods. Further, the enrichment factor is substantially improved, and the yield of recovery of the target region is significantly better than that previously reported. The methods herein do not require that the target region be amplified prior to or subsequent to the enrichment procedures.

Researchers who wish to study particular sequences, e.g., those related to disease susceptibility, agricultural improvements, infectivity of pathogens, etc., can do so more efficiently with a reliable method of isolating the particular sequences, e.g., from a more complex sample. For example, where a gene is known to be predictive of susceptibility to a disease, it is far more efficient and cost-effective to sequence the gene isolated from the rest of the genome than to sequence the entire genome and then try to identify and study the few sequences corresponding to the gene. As such, an objective of the methods herein is to provide a method for isolating a nucleic acid of interest, or target region, from a complex mixture of nucleic acid sequences. The complex mixture may be any mixture in which the target region is mixed with non-target regions, especially where the target region is a minority species. For example, a complex mixture comprising a target region can be a genome of an individual, a transcriptome of an individual, a microbiome of an individual, or an environmental sample comprising multiple genomes. Further, although in the interest of clarity, many embodiments herein are described with reference to a single target region, it will be clear that these methods are extendable to enrichment of more than one target region in a complex mixture. For example, the methods can be used to enrich for two or more target regions. In certain embodiments, the methods are used to enrich for multiple target regions that correspond to a single metabolic pathway or disease process in an organism, or to fragments of a single organism's genome in a metagenomic sample.

In preferred embodiments, a complex mixture comprising a target region is exposed to bis-PNA oligonucleotides specific for at least a portion of the target region or a region adjacent thereto that comprises at least one homopurine site. Binding of the bis-PNA oligonucleotides (also termed "bis-PNA clamps") to the homopurine site opens the duplex within or adjacent to a target region for which enrichment is desired by binding to one strand of the duplex, thereby displacing the opposite strand to provide an extended open region within the duplex. The complex comprising the duplex target and bis-PNA clamp(s) is sometimes referred to as a "P-loop," e.g., as described in International Application Publication Nos. WO92/20702, WO92/20703, and WO96/02558, all of which are incorporated herein by reference in their entireties for all purposes. The opposite strand is then free to bind to at least one oligonucleotide probe that comprises a complementary sequence.

The complementary oligonucleotide probe(s) that anneal to the displaced strand typically comprise a moiety to facilitate selection and/or retention of the bis-PNA/target/probe complexes such that they can be isolated from non-target nucleic acids in the sample. For example, the moiety can be an affinity tag that binds to a moiety on a solid or semi-solid surface (e.g., a column, array, or bead). In certain preferred embodiments, the affinity tag comprises at least one biotin moiety and the surface is linked to binding partners for biotin, e.g., avidin or streptavidin. The affinity tag can comprise multiple biotin moieties, e.g., single biotin moieties linked to multiple nucleotides and/or multiple biotin moieties linked to one or more single nucleotides. One preferred example of a multiple biotin moiety is a bis-biotin moiety comprising two biotins that both bind a single streptavidin (or other multivalent biotin-binding agent; bis-biotin tags are described in detail in U.S. patent application Ser. No. 14/303,296, filed Jun. 12, 2014, which is incorporated herein by reference in its entirety for all purposes. Alternatively or additionally, preferred surfaces include magnetic beads, which allow capture of bis-PNA/target/probe complexes using a magnet or magnetic device. The bound bis-PNA/target/probe complexes are separated from the unbound nucleic acids, e.g., by washing, and can be eluted from the surface for further processing or analysis.

Complementary oligonucleotide probes can be complementary to the sample nucleic acid along their full lengths, or can have non-complementary "tails" at one or both ends. Such tails can serve at a binding site for an affinity tag, such as the biotin moieties described above, or can be complementary to an oligonucleotide on a surface such that binding to the surface-bound oligo immobilizes the PNA/target/probe complex on the surface. In certain embodiments, the oligonucleotide probe is complementary to the sample nucleic acid over a region that is longer than the displaced portion of the duplex and serves to open the duplex further at one or both ends of the opened region. Such embodiments are benefitted by including nucleotides within the probe that have tighter binding to the sample nucleic acid than native nucleotides, and examples of such nucleotides include PNA (peptide nucleic acid) nucleotides, LNA (locked nucleic acid) nucleotides, 2'-O-methyl-modified nucleotides, as further described below.

Figure 4:
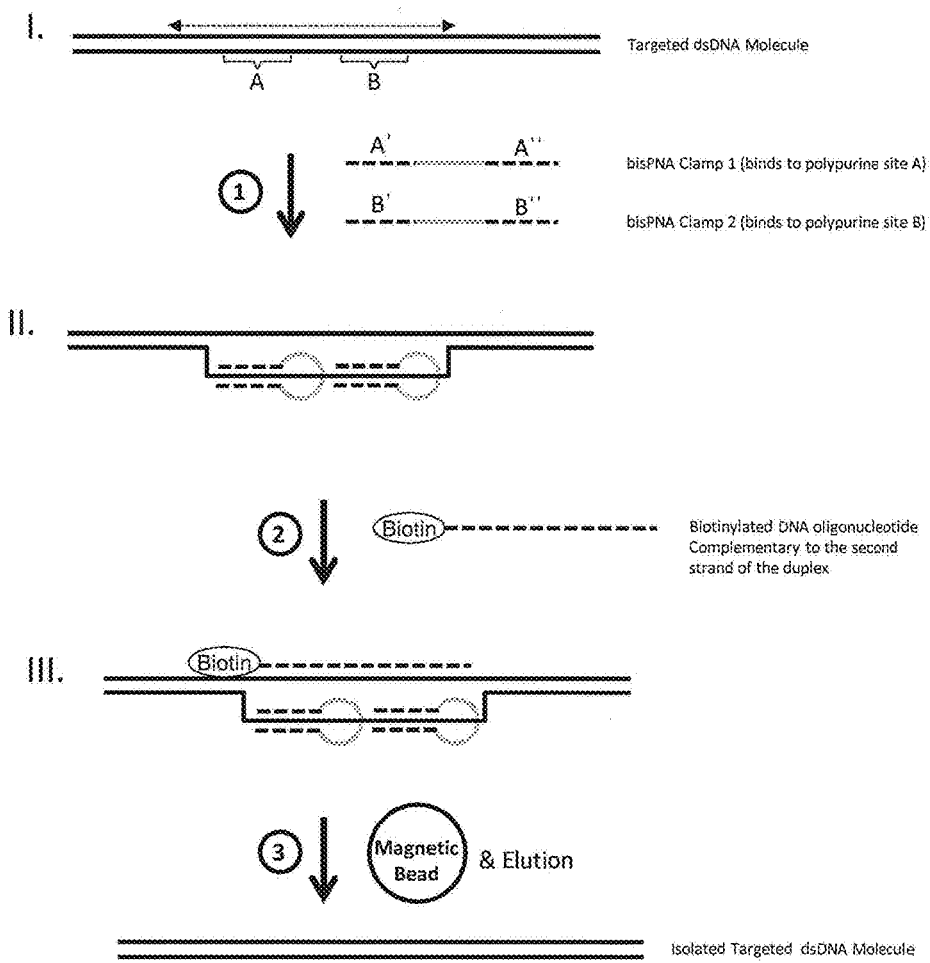
FIG. 4 provides an illustrative embodiment of how bis-PNA oligonucleotides can open a duplex region to allow binding of an oligonucleotide probe.

FIG. 4 provides an illustrative embodiment of how bis-PNA oligonucleotides can open a duplex region to allow binding of an oligonucleotide probe comprising a biotin moiety. Briefly, a double-stranded DNA molecule having a target region (dotted line with double arrowheads) is illustrated (I), where the target region comprises two specific polypurine sites, A and B. Two bis-PNA clamps are added at step 1, with clamp 1 having specificity for site A and clamp 2 having specificity for site B. Each clamp comprises two segments that align together and form a stable triple helix with the specific site in the duplex DNA molecule, as shown in II. The formation of the triple helix displaces the opposite strand of the duplex, forming an extended open region, and the displaced strand can be annealed to the biotinylated DNA oligonucleotide that is complementary to the displaced strand in step 2. The presence of multiple bis-PNA clamps in relatively short proximity on the duplex molecule is preferred because this orientation allows a longer portion of the opposite strand to be displaced, and a longer oligonucleotide can be annealed. Part III illustrates a duplex bound by two bis-PNA clamps and a biotinylated DNA oligonucleotide. Once this complex is assembled, the mixture is exposed to an agent that binds to the biotin, but not to nucleic acids lacking the biotin tag. Step 3 comprises addition of magnetic beads coated with a biotin-binding agent, e.g., avidin, streptavidin, a biotin-specific antibody, etc., followed by subsequent elution of the targeted molecules from the beads once the non-target nucleic acids are no longer present. More specifically, reaction conditions suitable for binding between the biotin and the agent are provided, and the nucleic acids in the mixture that are not captured are removed, e.g., by buffer exchange, thereby enriching for the captured nucleic acids. The enriched target region-containing nucleic acids are subsequently subjected to further analysis, e.g., cloning, sequencing, amplification, etc., preferably after elution from the beads. While preferred embodiments described herein comprise an oligonucleotide linked to a capture moiety, capture moieties can additionally or alternatively be linked to one or more bis-PNA clamps to further facilitate capture of the target fragments. PNAs can be conjugated with various moieties at the 5' or 3' end using known biochemical reactions. For example, at the 3' end a lysine is and conjugation uses the $NH_2$ group of the lysine. Optinally, one or more O-linkers can also be added as a spacer between the PNA and the moiety. As such, where capture moieties on oligonucleotide probes are discussed, it will be understood that such moieties can also be linked to a bis-PNA clamp for subsequent pull-down.

It will be clear to the ordinary artisan that many other capture moieties that are well known and routinely used in the art can be used in the place of the biotin, and that the magnetic bead can be replaced by another surface that can be populated with an agent that binds the capture moiety. For example, capture moiety can be a non-complementary terminal portion or "tail" of the oligonucleotide that doesn't bind to the displaced strand and is therefore available to hybridize to an oligonucleotide linked to a solid surface, such as the surface of a bead or microarray. Alternatively, the capture moiety can be an antigen that is specific for an antibody on a solid or semi-solid surface, or an antibody specific for an antigen on such surface. Many other examples of such affinity binding pairs are known in the art and contemplated for use with the methods herein, and both noncovalent and covalent binding partners are contemplated. Further, such capture moieties can be bound to one or both ends of the probe, or can be linked to one or more non-terminal nucleotides. One benefit of covalent binding partners is that the complementary oligonucleotides are more likely to remain bound to the surface when the target nucleic acids are removed, e.g., by denaturation. Reactive groups that form covalent bonds are well known in the art, and specific examples are provided in U.S. Patent Publication No. 2014/0134610, which is incorporated herein by reference in its entirety for all purposes. Further, other types of tags that facilitate capture can be linked to the oligonucleotide, e.g., mass tags, magnetic tags, or charged tags. Specific examples of reactive moieties for associating a moiety to an oligonucleotide probe or surface are well known and routinely used in the art. Certain examples of such moieties are provided in U.S. Patent Publication No. 2014/0134610, which is incorporated herein by reference in its entirety for all purposes.

Yet further, other moieties can be linked to the complementary oligonucleotide to provide additional functionality. For example, a detectable moiety can be linked, and non-limiting examples of detectable moieties include haptens, enzymes, fluorophores, chromophores, chemiluminescent compounds, quantum dots, and radioisotopes. Detectable moieties can be used in vitro, in vivo, or in situ to allow one to detect, identify, and/or quantitate the presence of the double-stranded target nucleic acid in a sample of interest. Alternatively or additionally, the oligonucleotide probe can be a primer comprising a 3'-hydroxyl group that serves as a polymerase binding site in a primer extension reaction, e.g., for enhanced stabilization of the bis-PNA/target/probe complex by pre-extension, or for subsequent amplification and/ or sequencing-by-synthesis. In certain embodiments, the oligonucleotide probe does not comprise a moiety that facilitates capture of a target nucleic acid, but instead serves as a primer in a polymerase-mediated primer-extension reaction in the presence of at least one type of nucleotide comprising the moiety, e.g., a biotinylated nucleotide. As such, the captured nucleic acids will be those that not only bound the oligonucleotide, but in which a tagged nucleotide was incorporated during primer extension. The nascent strand so generated can be removed from the target nucleic acid prior to further analysis (e.g., by heat or chemical denaturation), or may be used in such further analysis, e.g., as an initiation point for a sequencing by synthesis reaction. In such "pre-extension" embodiments, it is beneficial for the target nucleic acid to be linked at one or both ends by a stem-loop adapter to keep the two target strands together for subsequent steps.

Although the figures illustrate embodiments in which two bis-PNA clamps open a duplex to allow binding of one complementary oligonucleotide, this ratio is not required for performing the methods of the invention. Typically, at least two bis-PNA clamps are bound in close proximity to allow a large enough extended region for hybridization to a complementary oligo, but this is primarily because the length of most polypurine sites is too short to bind a bis-PNA clamp large enough to open an extended region sufficient for specific binding of the complementary oligonucleotide. However, in certain embodiments in which a sample nucleic acid comprises a polypurine site that is sufficiently long, a single long bis-PNA clamp is used to provide the extended open region for oligonucleotide hybridization. Similarly, where a longer open region is desired and more than two polypurine sites are present in close proximity, more than two bis-PNA clamps are used to open the duplex. Alternatively or in addition, more than one oligonucleotide can be annealed to a single-stranded region provided by bis-PNA clamp binding. Multiple oligonucleotide binding provides an opportunity to link multiple moieties to the complex, e.g., where each oligonucleotide comprises a different moiety. For example, a first oligonucleotide can comprise a capture moiety and a second oligonucleotide can comprise a detectable label, or both can comprise the same capture moiety to enhance binding and capture of the target molecules. Alternatively, or in addition, one oligonucleotide may serve as a polymerase binding site in a primer extension reaction, e.g., for enhanced stabilization of the bis-PNA/target/probe complex by pre-extension, or for subsequent amplification and/or sequencing-by-synthesis. In certain embodiments, two oligonucleotide probes that bind proximally could comprise labeling moieties that undergo FRET so that the resulting signal is indicative that both probes are bound, or the two oligonucleotides could hybridize immediately adjacent to one another such that they can be ligated together, further increasing the stability of the complex during subsequent steps, e.g., capture. As noted elsewhere herein, the probes can be linked to moieties at either or both ends, but where the probe is to be used for initiating polymerase-mediated synthesis the 3' end must be suitable for polymerase binding and extension.

In yet further embodiments, the oligonucleotide probe(s) can be pre-immobilized, e.g., on a solid surface, prior to being annealed to the displaced single-stranded region of a bis-PNA/target region complex. In contrast to an embodiment in which the complementary probe comprises a tail that hybridizes to an immobilized oligonucleotide, an embodiment comprising a complementary probe that is pre-immobilized may require only one single-stranded oligonucleotide that comprises a first portion complementary to a region of the sample nucleic acid, and a second portion that is linked directly to a surface, e.g., on a bead, microarray, column, etc. The nucleic acids in the mixture that do not bind to the bis-PNA clamps will not bind to the pre-immobilized probes, nor will nucleic acids that are bound one or more bis-PNA clamps but do not comprise a sequence complementary to the probe. In such embodiments, a covalent or non-covalent bond may link a moiety on the probe to the surface, or the probe may be directly linked, e.g., synthesized thereon in an oligonucleotide microarray format.

In certain embodiments, additional agents can be added to the mixture to enhance binding of the oligonucleotide probe to the single-stranded region. For example, proteins that enhance hybridization between complementary sequences can be added, such as RecA, RecT, Rad51/Rad52, human splicing factor PSF, protein beta of coliphage lambda, or a combination thereof. More information on these strand-exchange proteins is replete in the literature, e.g., in Noirot, et al. (1998) J. Biol. Chem. 273(20):12274-80); Bi, et al. (2004) Proc. Natl. Acad. Sci. USA 101(26):9568-72; Akhmedov, et al. (2000) Nuc. Ac. Res. 28(16):3022-30; Xu, et al. (2002) J. Biol. Chem. 277(16):14321-14328; and Rybalchenko, et al. (2004) Proc. Natl. Acad. Sci. USA 101(49):17056-60, all of which are incorporated herein by reference in their entireties for all purposes. Other types of proteins that can be used to promote binding of complementary oligonucleotides to the displaced strand include helicases and single-stranded DNA binding proteins (SSBs). Helicases are a class of enzymes that unwind double-stranded DNA and, as such, can be used to further open the duplex to allow more efficient binding of the complementary oligonucleotide. For example, where the single-stranded region displaced by the bis-PNA clamps is shorter than the complementary oligonucleotide, the use of a helicase can unwind the duplex further, thereby increasing the accessibility of a target region. Single-stranded DNA binding proteins can help to keep a duplex region unwound, further increasing accessibility of the target region.

Alternatively or additionally, the oligonucleotide probes can comprise modified nucleotides that exhibit tighter binding to their complementary base than do native bases, e.g., increasing the melting temperature of the target/probe interaction. This can increase the stability of the complex and facilitate capture of the target nucleic acid. Some examples are PNA (peptide nucleic acid) nucleotides, LNA (locked nucleic acid) nucleotides, 2'-O-methyl-modified nucleotides, and other modified nucleotides known in the art to have a greater affinity to a complementary base than does a canonical nucleotide. Further, although the complementary oligonucleotide probe is between five and twenty nucleotides in length, and more preferably between seven to sixteen nucleotides in length, the length and base composition of the complementary oligonucleotide can also be varied, depending on the type of sequence to be captured. For example, capture of a highly repetitive sequence may require a longer complementary oligonucleotide that includes both a non-repetitive flanking sequence and a portion of the repeat region, or may be long enough to select a particular haplotype that spans two or more variable base positions. In certain embodiments, complementary oligonucleotides are used within larger constructs, such as within capture-hook oligonucleotides, which are described in U.S. Pat. No. 8,658,364, incorporated herein by reference in its entirety.

In certain embodiments, the nucleic acid sample is subjected to fragmentation prior to enrichment, depending on the size of the nucleic acids in the mixture and the desired size for enrichment. For example, whole genomic DNA can be fragmented to produce genome fragments having the desired size. Although such fragmentation may be random, e.g., by shearing, in preferred embodiments the fragments are created using a strategy that minimally fragments the target region. For example, where the target region is smaller than the desired fragment size, the strategy would fragment outside of the target region so that fragments are produced that encompass the entire target region. Where the target region is larger than the desired fragment size, a preferred strategy would divide the target region only as much as necessary to produce the size fragments desired. Specific fragmentation strategies are often performed with restriction endonucleases, especially where the sequence around a target region is known, e.g., in a reference sequence. Where the sizes of the nucleic acids in the original sample are in a desired range, e.g., certain bacterial genomes, cDNA libraries, etc., no fragmentation may be necessary. In certain preferred embodiments, a restriction enzymes (e.g., type II or type IIs) are chosen to provide target fragments having different ends, e.g., different overhang sequences, or one blunt ended and one having an overhang. This allows for different treatment of the two ends, e.g., ligation of different adapters in some embodiments.

In certain embodiments, subsequent to any fragmentation and prior to introduction of bis-PNA clamps, the nucleic acids in the mixture are linked to stem-loop (a.k.a., "hairpin") adapters at one or both ends to lock the two strands together during the enrichment procedure. In certain preferred embodiments, the stem-loop adapters are added to both ends to produce nucleic acid molecules that are structurally linear, but topologically circular. Linking such adapters to both ends of the nucleic acids results in nucleic acid constructs having no free 5' or 3' ends and comprising a double-stranded nucleic acid fragment from the mixture. The double-stranded region within these constructs can be denatured or unwound to produce a single-stranded circular nucleic acid molecule. These molecules are beneficially used as nucleic acid sequencing templates for use of polymerase-mediated, sequencing-by-synthesis methods. One specific benefit is that they allow both strands to be sequenced, optionally repeatedly, as the polymerase translocates around the template, e.g., performing "rolling-circle" synthesis. The nascent strand so generated comprises complements to both strands of the original double-stranded fragment, and where the synthesis can be monitored in real-time, the sequence of the nucleotide incorporation events provides, by complementarity, the nucleotide sequence of both strands of the original nucleic acid fragment. Methods for creating and sequencing such nucleic acids are known in the art, e.g., in U.S. Pat. No. 8,153,375 and in Travers, et al. (2010) Nuc. Ac. Res. 38(15): e159, both of which are incorporated herein by reference in their entireties for all purposes. Further, linking the two strands together at one or both ends has the added benefit of locking the two strands together since even upon strand separation the strand remain linked. As such, the binding of the bis-PNA clamps and complementary oligo won't unlink the two strands, even under the stringent conditions described herein. Further, the presence of a single hairpin adapter may provide a benefit of facilitating the separation of the strands to allow binding of the bis-PNA clams and complementary oligo since a single-hairpin molecule closed at only one end is less thermally stable than a two-hairpin molecule closed at both ends. Where only a single hairpin adapter is used, the enriched fragments can be treated to add a second hairpin adapter prior to subsequent analysis, or can be analyzed as a single-hairpin molecule, which still provides some level of redundancy since the two strands are complementary to each other. For example, they can be sequenced and the sequences for both strands analyzed together to provide a consensus sequence for the original double-stranded target fragment. Preferably they are sequenced using a single-molecule sequencing method, e.g., SMRT® sequencing or nanopore sequencing, both of which are known in the art and described elsewhere herein.

In certain aspects, more specific bis-PNA clamp binding is provided by performing the binding reaction at an elevated temperature of about 37-65° C. The specific binding temperature is dependent upon a number of experimental factors including, but not limited to, the GC content of the region(s) to which the bis-PNA clamp(s) will bind, and the pH and salt concentration of the reaction mixture. As such, conventional strategies known to the ordinary artisan can be utilized to determine an optimal temperature for binding of the bis-PNA clamp(s) to the sample nucleic acids. Preferably, the nucleic acids are linked to stem-loop adapters at both ends prior to this incubation at elevated temperature since the adapters will covalently link the two strands, keeping their ends together even if the hybridization between the strands is disrupted during the incubation. The bis-PNA clamps hybridize well and stably bind to the nucleic acids at elevated temperature. The elevated temperature reduces the non-specific binding of the bis-PNA clamps to non-target regions. Optionally, in certain aspects, more specific bis-PNA clamp binding is provided by performing the binding reaction after denaturing the double-stranded portion of the sample nucleic acids at an elevated temperature of about 65° C.-100° C., and an elevated temperature of about 80° C. is preferred in some specific embodiments. The denaturing temperature chosen is dependent upon the GC content of the double-stranded region, with a higher GC content requiring a higher denaturing temperature. Calculations for the determination of an appropriate denaturation temperature based on GC content are well known in the art, e.g., such calculations are routinely used to determine denaturation temperatures during PCR amplification. This denaturation ensures that the strands are denatured to facilitate binding of the bis-PNA clamps, which are generally present in the mixture during the denaturation. Once again, preferably the nucleic acids in the sample are linked to the stem-loop adapters to keep the strands together during the denaturation step. In some embodiments, following the denaturation step, the mixture is cooled (preferably, quickly) to the elevated hybridization temperature for binding of the bis-PNA clamps, as discussed above. In other embodiments, the denaturation step is followed by a rapid cooling of the mixture to a temperature of about 37° C. or lower, e.g., at a temperature of about 30° C., 25° C., 20° C., 15° C., 10° C., 7° C., or 4° C. For example, the denatured sample can be removed from the heat source and placed directly in ice with no incubation at any intermediate temperature; effective binding of the bis-PNA clamps is achieved under these conditions, as well. Following bis-PNA clamp binding, the unbound clamps are removed, e.g., using a size-selection strategy. Preferred size selection is performed using spin columns, beads (e.g., AMPure® beads), electrophoresis, and other methods known in the art to remove small nucleic acids from larger nucleic acids. Typically, the temperature of the mixture is raised prior to addition of the complementary oligonucleotide probes, e.g., to at least 25° C., and more preferably to about 35° C. Additional details are provided below and in the Example herein.

In certain aspects, the assembly and stability of the bis-PNA/target/probe complex is improved by stepwise elevation of the ionic strength of the solution. Specifically, the assembly of the bis-PNA/target/probe complex (step 1) is sensitive to the ionic strength with the initial binding of bisPNAs enhanced by low ionic strength, e.g., less than about 25 mM. In a second step, dissociation of the non-specifically bound bisPNA probes is best between 150 and 250 mM ionic strength, preferably at about 200 mM ionic strength. Both the hybridization of the complementary oligonucleotide probe (step 3) and the dissociation of the non-specifically bound probes (step 4) are performed at between 450 and 550 mM ionic strength, preferably at about 500 mM ionic strength. These ionic strengths appear to be independent of the target sequence. However, a purification step optionally performed between steps 3 and 4 is ionic-strength dependent.

The solution containing the assembled bis-PNA/target/probe complex is preferably purified of excess oligonucleotide probe to minimize non-specific targeting. This is optionally performed by AMPure® bead purification (from Beckman Coulter, Inc.), which requires elution into low ionic-strength buffer. Typically, elution from AMPure beads is performed in elution buffer (10 mM Tris pH 8.0), but this buffer does not provide a high enough ionic strength to stabilize the complementary oligonucleotide bound to the displaced strand in the assembly. The ionic strength of the elution buffer used for purification of the bis-PNA/target/probe complex is thus elevated to the value that yields melting temperatures (Tm's) above 40° C. for the oligonucleotide in question, e.g., based on its GC content. Of course, other known methods can be used to separate the unbound oligonucleotides from the bis-PNA/target/probe complex, e.g., via column or electrophoretic mobility separation techniques.

In certain aspects, the enrichment factor achieved is increased by elevating the pH of the solution during binding of the bis-PNA clamps. In preferred embodiments, the pH of the binding reaction is about pH 8.0. This was a surprising finding since initial descriptions of the bis-PNA clamps preferred the binding reactions be performed at a pH lower than 7, with the optimum being around 6.0. This was due to the instability of Hoogsteen's base pairing between G and C in the triplex at pH's above 7. One can perform bisPNA hybridization at pH's above 7, provided that C's are replaced with J's in the C-terminal stretch of the probe. This change in the base composition of the probe eliminates the pH sensitivity of the resulting Hoogsteen's base pairs. As such, in preferred embodiments, bisPNA hybridization is carried out at pH 8.0 and subsequent steps are performed at pH 6.1, excluding the magnetic bead immobilization where such a capture strategy is implemented.

There are multiple buffer-exchange steps in the protocol. The first occurs following binding of the bis-PNA clamps, and is used to dissociate the non-specifically bound bis-PNA clamps. The second occurs following hybridization of the complementary oligonucleotide probe, and is used to dissociate the non-specifically bound probes. The third occurs following the capture of the target region(s), and results in the elution of the nucleic acids comprising the target region(s) into a high-ionic strength buffer, and the last transfers the eluted nucleic acids into a buffer appropriate for a subsequent procedure, e.g., amplification, cloning, sequencing, etc. Applicants have found that replacing the size-exclusion column purification steps originally described in the art with a purification protocol that instead utilizes magnetic beads (e.g., AMPure® beads from Beckman Coulter, Inc.) provides a significant improvement in the yield of DNA recovery for the buffer exchange steps during the enrichment. As such, in preferred embodiments, size-exclusion columns are not used in the methods provided herein, and a magnetic bead purification strategy, such as the AMPure bead method, is used for purification. One important aspect of these purification steps is the correct volume fraction of the magnetic bead addition. Using a 0.6 volume is preferred since that amount does not precipitate short oligonucleotides or bisPNAs. An exception to this general practice is that during the last AMPure® step after the elution of the target sequence off the magnetic beads, a volume of 1.8× is preferred because that volume yields the highest recovery of the target region from what is a very dilute solution of DNA at this step.

These improvements are not mutually exclusive and are preferably used in combination, e.g., at least two or three, or more preferably, all four are used in one enrichment procedure. For example, preferably, the bis-PNA binding reaction is subjected to a denaturation temperature of 65-80° C. in a pH 8.0 reaction mixture, and subsequently quickly cooled to a temperature from about 37° C. to 4° C. This strategy has the added benefit of not requiring a specific binding temperature that is dependent upon the sequence (e.g., GC content) of the target region. As such, multiple target regions having differing GC contents could be enriched in a single reaction mixture. In addition, the ionic strength of solution is kept high to stabilize the complex during the subsequent steps, and the buffer exchanges are performed using magnetic-bead-based size-selection strategies.

In certain aspects, the invention provides strategies for the design of the bis-PNA clamps. FIG. 5 provides a graphical illustration of the generic structure of a target region (a) and bis-PNA clamps (b). The portions of the nucleic acid that are bound by the bis-PNA clamps (e.g., A and B in FIGS. 1 and 3) are labeled "bis-PNA Clamp 1 Binding Site" and "bis-PNA Clamp 1 Binding Site" and each of these sites comprises a polypurine site ("R" boxes). The sites are both on the same strand and are separated by a short polypyrimidine segment ("Y" boxes). Preferably, the separation or "spacer" between the polypurine sites is 1-5 nucleotides, or more preferably 2 or 3 nucleotides in length, and can comprise pyrimidines, purines, or a combination thereof. Without being bound by theory, the spacer is likely needed for steric reasons, e.g., to accommodate the bis-PNA linker (the loop) in the bis-PNA clamp. The two polypurine segments are typically at least seven nucleotides long, but do not have to be of equal length. The "N" boxes represent nucleotides having any base, e.g., preferably the canonical A, G, C, or T bases, methylated bases, or other naturally occurring bases. The segments of the bis-PNA clamps that bind to the polypurine sites typically comprise at least five PNA subunits, and are preferably longer, e.g., six to eight PNA subunits. However, they can be even longer when the target nucleic acid comprises a polypurine stretch that is longer, and in especially preferred embodiments, the segments of the bis-PNA clamps that bind to the polypurine sites are the length of a typical PCR primer, e.g., about 20 subunits in length. A longer bis-PNA segment enhances the selectivity and stability of the bis-PNA/target/probe complex. Preferred nucleobases in the bis-PNA clamps are thymine, cytosine, pseudoisocytosine, and base J. The bis-PNA clamps are typically designed to be positively charged, and the example in (b) accomplishes this by having two lysine residues at the C-terminus, and two lysine residues at the N-terminus.

Optionally, there can be one lysine residue at the C-terminus and two lysine residues at the N-terminus, or there can be two lysine residues at the C-terminus and one lysine residue at the N-terminus. The positive charge can optionally be provided by incorporating other positively charged PNA solubility enhancers during the chemical synthesis of the bis-PNA clamp, e.g., as described in Gildea, et al. (1998) Tett. Lett. 39: 7255-7258, which is incorporated herein by reference in its entirety for all purposes. Each clamp has two polypyrimidine triplet-forming segments, one adjacent to the N-terminal lysines, and the other adjacent to the C-terminal lysines. The triplet-forming segments depicted in FIG. 5 are separated by several 0-linkers to form the bis-PNA linker. Each O-linker has the general structure:

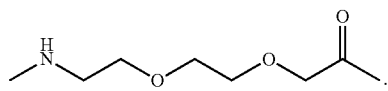

Other linkers can also be used in the bis-PNA clamp, and such linkers are typically a hydrocarbon-based chain that has been modified to increase its polarity for enhanced solubility, e.g., C6A linkers, C11SH linkers, C6SH linkers, and the like, but 0-linkers are preferred. All of these linkers are commercially available, e.g., from PNA Bio in Thousand Oaks, Calif. Optionally, any C bases in the triplet-forming section nearest the C terminus can be replaced with J bases; this substitution decreases the pH dependency of probe binding. Preferably, all C bases between the C-terminus and the linker are replaced by J bases, and this reduces any pH dependency of the binding of the bis-PNA clamp. (For more information on J bases, see Borst, et al. (2008) Annu. Rev. Microbiol. 62:235-51, incorporated by reference herein in its entirety for all purposes.) Yet further, although specific embodiments described herein focus on bis-PNA molecules for opening a duplex region, other types of molecules that are sequence-specific and able to open a duplex are also contemplated for use in the methods of the invention, e.g., bis-BNAs, bis-LNAs, and the like.

Figure 6:
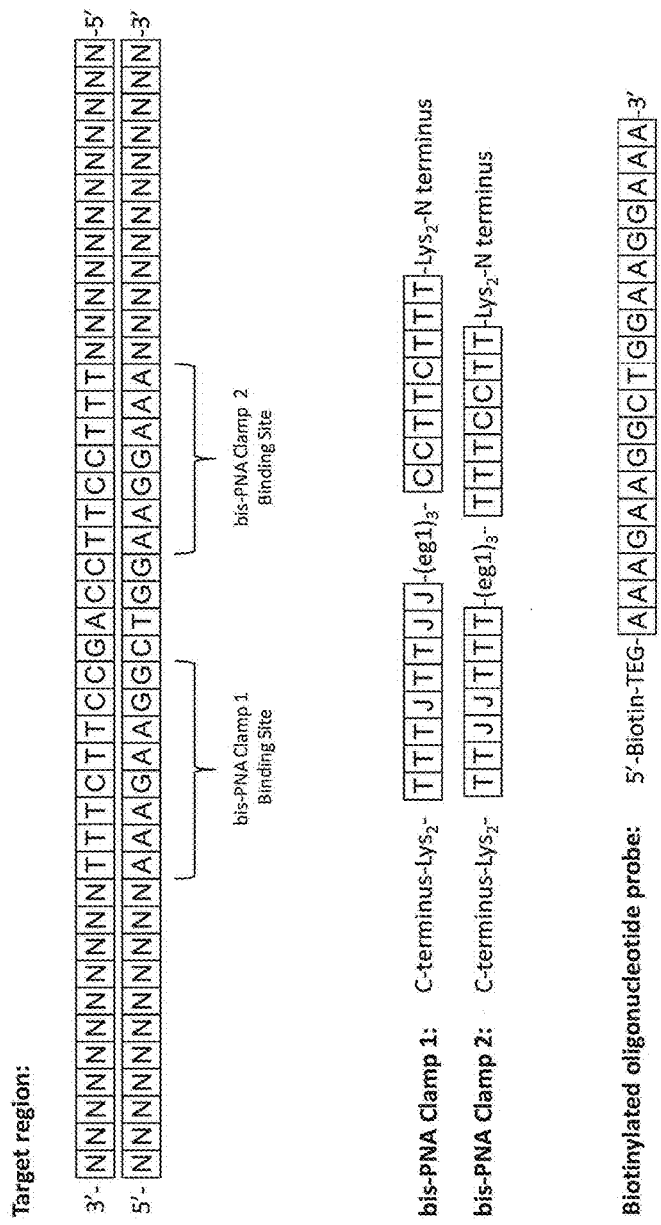
FIG. 6 provides a specific example of a target region having two clamp binding sites (SEQ ID NO: 9 in the top strand and complementary SEQ ID NO: 10 in the bottom strand), and the structures of the corresponding bis-PNA clamps and a biotinylated oligonucleotide probe that can bind to the displaced strand (containing SEQ ID NO: 10).

FIG. 6 provides a specific example of a target region having two clamp binding sites (a), the structures of the corresponding bis-PNA clamps (b), and a biotinylated oligonucleotide probe that can bind to the displaced strand (c). In this example, the bis-PNA Clamp 1 Binding Site is complementary to the triplet-forming sections of bis-PNA Clamp 1; and the bis-PNA Clamp 2 Binding Site is complementary to the triplet-forming sections of bis-PNA Clamp 2. The C bases in the triplet-forming section nearest the C terminus are replaced with J bases in both clamps to decrease the pH dependency of probe binding. The complementary oligonucleotide has a biotin tag linked to the 5' terminus through a triethylene glycol (TEG) spacer. In certain embodiments, the bis-PNA clamps are bound to the target region, and the biotinylated oligonucleotide is subsequently bound to the displaced strand. In preferred embodiments, the resulting complex is isolated by adding streptavidin-coated magnetic beads to which the complex binds. The nucleic acids that do not comprise the target region remain in the solution. The target region is eluted off of the magnetic beads by incubation at elevated temperatures and ionic strengths.

III. Methods Using Gene-Editing Systems to Enrich for Target Regions

As described briefly above, certain preferred embodiments of the methods provided herein enrich target nucleic acids, at least in part, by implementing the excision of target regions from sample nucleic acids via cleavage using the RNA-directed Cas9 endonuclease, which is conventionally used in gene-editing systems. Such cleavage is typically followed by an isolation step to select the excised target region and removal of the non-target nucleic acids. The final pool need not be entirely free of non-target nucleic acids, but will be significantly enriched for the target nucleic acids. Although the CRISPR-Cas system will be discussed at length herein, other gene-editing technologies that introduce cuts at specific locations in a nucleic acid sample can also be used in an analogous manner to enrich for a target region, e.g., using other RNA-directed endonucleases or other systems for site-specific cleavage. For example, TAL Effector Nucleases (TALENs) can be engineered to create double-strand breaks at specific locations, e.g., flanking a target region (e.g., see Christian, et al. (2010) Genetics 186: 757-761; Li, et al. (2011) Nucleic Acids Research 39: 359-372; and Miller, et al. (2011) Nat. Biotechnology 29: 143-148, all incorporated by reference herein). Likewise, zinc-finger nucleases (ZFNs) are artificial restriction enzymes created by fusing a DNA-cleavage domain to a zinc finger DNA-binding domain, and can be engineered to target desired DNA sequences (e.g., see Kim, et al. (1996) Proc. Natl. Acad. Sci. 93:1156-1160, incorporated by reference herein). Yet further, the bacteriophage P1 recombination enhancement function (Ref) protein is a RecA-dependent endonuclease that creates double-stranded breaks in duplex DNA at the site of RecA-mediated insertion of an oligonucleotide into a complementary region of a duplex nucleic acid. These cut sites can be targeted through the selection of the oligonucleotides inserted by the RecA protein, e.g., they can be chosen to be near or within a target region. In further embodiments, a site-specific nicking enzyme, e.g., BspD9I, a mutant Ref protein, or a mutant Cas9 nuclease (e.g., having one inactivated nuclease domain (HNH or RuvC nuclease) such as H840A and N863A Cas9 mutants), can be used to nick a double-stranded fragment at or near a target region and subsequent treatment with T7 endonuclease I, or a derivative thereof, will result in a double-strand break having an overhang sequence that can be used for specific ligation of an adapter having a complementary overhang. The activity of other Cas9 mutants may vary depending on the reaction conditions; for example, N854A, has been observed to nick in some instances (U.S. Pat. No. 8,697,359), and to have double-strand cleavage activity in others (Fonfara, et al. (2014) Nucleic Acids Research 42(4): 2577-2590). In certain embodiments, Cas9 endonuclease can be engineered to have enhanced characteristics, e.g., higher specificity than the wild-type enzyme. Certain high-specificity Cas9 enzymes are described in Kleinstiver, et al. (2016) Nature, DOI:10.1038/nature16526; and Slaymaker, et al. (2016) Science 351(6268): 84-88, both of which are incorporated herein by reference in their entireties for all purposes. It will be understood that reference to Cas9 herein includes not only the extensively studied Cas9 from S. pyogenes, but also Cas9 orthologs from other bacterial strains, including but not limited to S. thermophilus (e.g., CRISPR3 and CRISPR1 enzymes), S. mutans, C. jejuni, N. meningitidis, P. multocida, and F. novicida. (See, e.g., Fonfara, et al. (2014) Nucleic Acids Research 42(4): 2577-2590, incorporated herein by reference in its entirety for all purposes.) As noted elsewhere herein, the sequence of the PAM will vary depending on the particular CRISPR-Cas system, e.g., which Cas9 ortholog is being used.

Alternatively, a Cpf1 DNA endonuclease (e.g., from *F. novicida*) can be used in place of the Cas9 endonuclease. The Cpf1 endonuclease belongs to the class 2 CRISPR-Cas system that utilizes a single RNA fragment as the guide RNA. For example, Cpf1 endonuclease can utilize a 43-nucleotide crRNA and specifically cut the DNA target having a 24-base sequence complementary to the 3' end of the crRNA. Digestion by Cpf1 endonuclease leaves a 5-nucleotide 5' overhang instead of the blunt ends typically produced by Cas9 digestion. The overhang can allow for specific ligation to an adapter having a complementary overhang, e.g., a stem-loop or hairpin adapter used to create SMRTbell™ templates or to link two strands together, e.g., using a hairpin adapter, prior to passage through a nanopore. The Cpf1 endonuclease is further described in Zetsche, et al. (2015) Cell 163:1-13, which is incorporated herein by reference in its entirety for all purposes. As such, although specific embodiments herein are focused on the use of the CRISPR-Cas system for excising target regions, it will be understood that other gene-editing systems can also be used in the methods and compositions provided herein, so reference to RNA-Cas9 complexes is one exemplary species in a more general class of RNA-endonuclease complexes, e.g., where the endonuclease is directed to a cleavage site by the RNA component of the complex.

The use of the CRISPR-Cas mechanism for excision of a target region requires one or more RNAs, e.g., sgRNAs and/or crRNAs, complementary to locations where the sample nucleic acid is to be cleaved by the Cas9 endonuclease. When using a crRNA:tracrRNA to direct Cas9 cleavage, the tracrRNA need not be specifically designed since it does not hybridize to the sample nucleic acids. As such, tracrRNAs can be synthesized based on previously published sequences (e.g., Jinek, et al. (2012) Science 337:816-821, incorporated herein by reference in its entirety) or purchased from various manufacturers, e.g., Dharmacon, Inc. The design of sgRNAs and crRNAs requires some knowledge of the sequence near the cleavage site, typically near one or both ends of the target region, and may be outside of the target region, or within the target region, depending on the orientation of the Cas9 complex bound to the sample nucleic acid, since this orientation determines where the cleavage will occur relative to the binding site on the sample nucleic acid. Typically, the complementary region is 12-20 nucleotides in length, as long as the specificity of binding is sufficient to ensure that the desired sequence is cleaved, preferably without cleavage of many non-desired regions. Further, although in the interest of clarity, many embodiments herein are described with reference to a single target region, it will be clear that these methods are extendable to enrichment of more than one target region in a complex mixture. For example, the methods can be used to enrich for two or more target regions as long as sgRNAs or crRNA:tracrRNA complexes can be designed to target such regions. In certain embodiments, the methods are used to enrich for multiple target regions that correspond to a single metabolic pathway or disease process in an organism, to fragments of a single organism's genome in a metagenomic sample, to specific viral subpopulations in a mixed viral sample, or to diagnostic markers, e.g., for disease susceptibility or drug response. In addition, although specific embodiments herein describe the use of an sgRNA molecule for targeting a region of interest for cleavage by Cas9, it is also contemplated that two separate RNA molecules in a crRNA:tracrRNA complex like that found in bacterial systems could be used instead of a single sgRNA molecule. These two methodologies are described in greater detail below.

Figure 7:
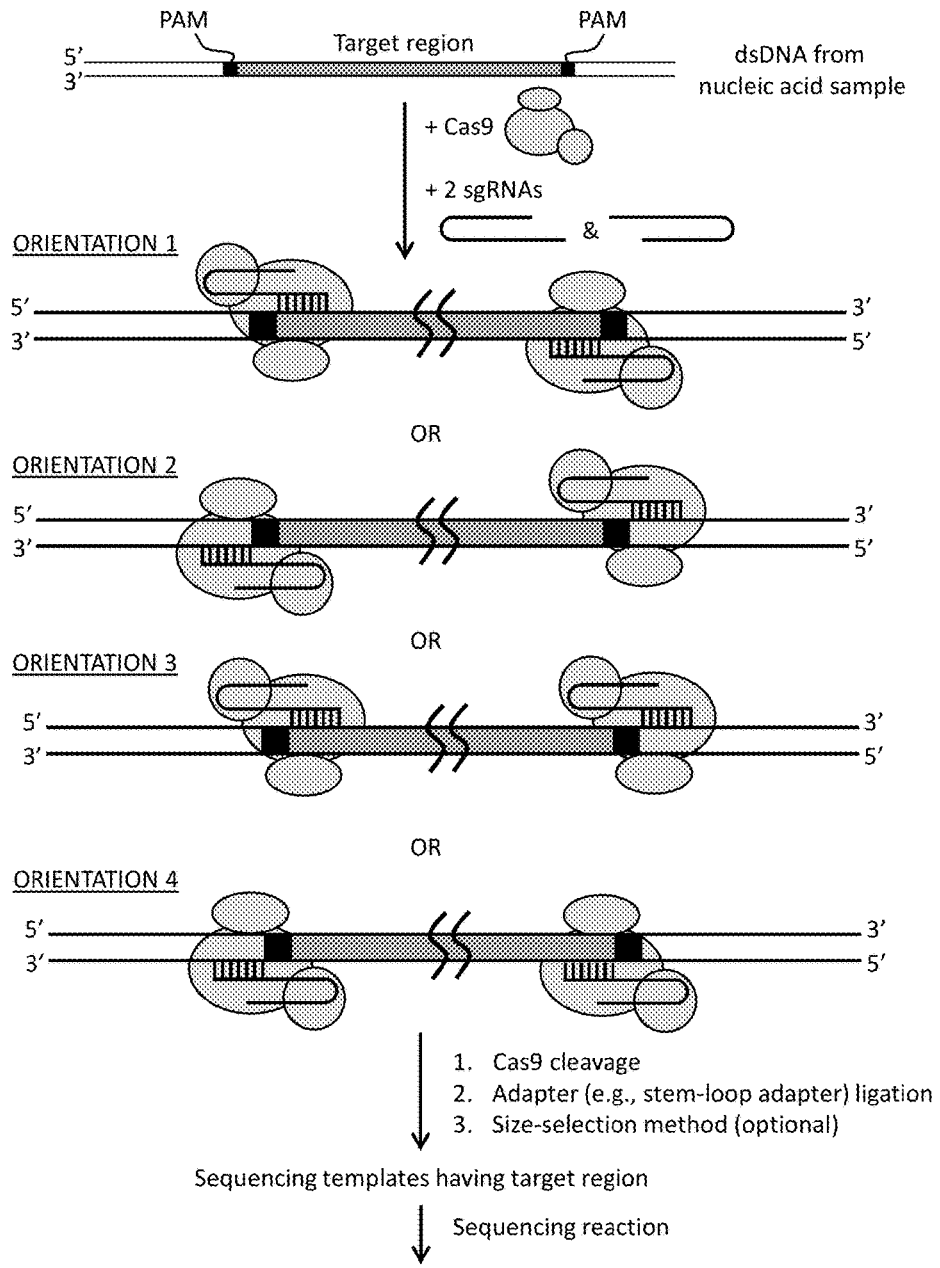
FIG. 7 provides an illustrative embodiment of methods for enriching for a target region of interest that comprises cleavage by two Cas9 endonucleases. Four different orientations of the two RNA-Cas9 complexes flanking the target region are shown.

FIG. 7 illustrates how different orientations of a double Cas9 cleavage require complementarity either within or outside of a target region that extends to the PAM sites, given the site of cleavage with respect to the complementary sequence and the PAM site. For the purpose of explaining the illustrated strategies, the target region in FIG. 7 extends across the full region between the two PAM sites, although in practice a target region that is desired to be analyzed, e.g., because of a biological significance of that region, may not extend all the way to the PAM site, or may extend into the PAM site, or may extend past the PAM site (e.g., where the region(s) that extends beyond PAM is not of interest in subsequent steps or analysis). All of these orientations require the presence of two Cas9 enzymes and two sgRNAs (assuming that the complementary regions will be different at the ends, as will most commonly be the case). In orientation A, the complementary regions are within the target region at both ends, and in orientation B, the complementary regions are both outside of the target region. Orientations C and D illustrate cases in which the complementary region is within the target region at one end, and outside of the target region at the opposite end. Where the complementary region is on the outside, a few nucleotides will be lost from the ends of the target region due to the space between the PAM site and the cleavage site. In contrast, where the complementary region is within the target region, the cleavage will occur outside of the target region. Although the various orientations shown in FIG. 7 require two Cas9 cleavage events to excise the target region, alternative embodiments in which the target region is proximal to an end of a nucleic acid fragment, e.g., introduced by prior restriction digest, shearing, etc., only one Cas9 cleavage may be necessary, as discussed further below.

A target region can be enriched in a single target fragment, or portions of the target region can be enriched in multiple target fragments, e.g., where a target region is too large to fit within a single target fragment or where the Cas9 endonuclease or other fragmentation cuts at a locus within the target region. As such, a "target fragment" is a nucleic acid comprising at least a portion of a target region, and in some embodiments, the entirety of a target region. A "target region" is a region within a nucleic acid sample for which enrichment is sought. In some embodiments, a large target fragment (e.g., 5, 10, 15, 20, 50 100 kb or more in length) is subjected to further cleavage to produce one or more smaller target fragments having at least a portion of the target region and non-target fragments that do not include any of the target region. Since the enrichment strategy described herein is designed to cut at specific or known locations within or near a target region, the size of the target fragment generated is often known to the practitioner. As such, a size-selection procedure can optionally be performed following the cleavage, which will remove most if not all of the fragments generated at loci other than the intended target-associated loci since the non-target fragments are unlikely to have the same size as the target fragment. Size-selection methods are well known to those knowledgeable in the art, and include gel-based methods, microfluidic methods, chromatography, density fractionation, bead-based methods, etc.

In certain embodiments, there is an additional moiety on one or both of the RNA molecules used to guide Cas9 to the target region. For example, one end of an sgRNA molecule can be linked to a means for capturing the excised fragment, e.g., an affinity tag. In specific embodiments, this moiety comprises a biotin or an oligonucleotide that is complementary to a nucleic acid probe on a solid surface. For example, the moiety can be a homopolymeric sequence, such as polyA, where a complementary polymeric sequence, such as polyT, is linked to a solid surface; or, alternatively, the moiety can comprise one or more biotins, where a plurality of streptavidin molecules are linked to a solid surface. Other types of affinity tags are contemplated, such as those known in the art and described elsewhere herein. The target fragments can be recovered by eluting them from the surface after washing away the non-target molecules. A sgRNA-linked affinity tag can be used in combination with a size-selection, e.g., to ensure that the captured target fragments are full length and comprise the entire target region sought to be analyzed, and such a size selection can be performed either before or after the capture procedure. Following recovery of fragments, whether via size-selection, capture, or a combination thereof, such fragments are subjected to further analysis, cloning, template preparation, amplification, sequencing, and the like.

In certain embodiments, the sample nucleic acids are fragmented prior to or following Cas9 cleavage, preferably using a method that does not cut within the target region. Such cleavage may result in a nucleic acid fragment having the target region near enough to an end so only one Cas9 cleavage would be necessary to excise a fragment comprising the target region, the "target fragment." Alternatively, it may be necessary to perform Cas9 cleavage at both ends of the target region to generate a target fragment appropriate for further analysis, e.g., sequencing, amplification, etc. Preferably, the type of termini produced by the non-Cas9 fragmentation are different from that produced by the Cas9 cleavage. For example, since Cas9 cleavage typically generates a blunt end, a digestion reaction that generates 3' or 5' overhangs at each end of the resulting fragments can be chosen. As such, following Cas9 cleavage, the only termini not having the overhangs are those that are the Cas9 cleavage sites, i.e., at one or both ends of the target fragments.

Where both ends of the target fragments comprise Cas9 cleavage sites, the resulting mixture can be treated with a ligase in the presence of an excess of blunt-ended adapters that are resistant to exonuclease digestion (e.g., hairpin/ stem-loop adapters), which can only ligate to the blunt-ended target fragments. The mixture can optionally be treated prior to the ligation reaction, e.g., to ensure that the blunt ends are truly blunt and have the requisite 5'-phosphate and 3'-OH groups needed for adapter ligation. For example, the fragments can be treated with T4 polymerase and T4 kinase prior to ligation. This is sometimes referred to as an "end-repair" step and is an optional step following any cleavage event described herein; however, in certain preferred embodiments no end-repair step is performed following Cas9 cleavage. The ligation reaction will link an adapter to both ends of the target fragments. Although it is possible that some of the non-target fragment will also anneal to each other during the ligation reaction, the overhangs will largely prevent ligation to a blunt-ended adapter. Following the ligation reaction, the mixture is optionally treated with exonucleases that degrade all the fragments that are not adapter linked, which effectively removes all fragments except those that are adapter linked. For example, the mixture can be treated with ExoIII and ExoVII to remove the non-target fragments. The treatment results in a mixture that is enriched for the target sequences. Further information on methods for degrading non-target sequences is provided in U.S. Patent Publication No. 2014/0134610, which is incorporated herein by reference in its entirety for all purposes.

As noted above, if a sample nucleic acid is subjected to a restriction digestion or other fragmentation procedure prior to or following Cas9 cleavage, the target region may be located near a double-stranded break that can serve as the first end of the target fragment to be enriched. Preferably the fragmentation procedure cuts near enough to the target region, but not within the target region, such that a single Cas9 cleavage in the nucleic acid fragment proximal to the end of the target region farthest from the double-strand break will result in a target fragment having a first end at the double-stranded break and a second end at the Cas9 cleavage. The fragments can optionally be subjected to an end-repair step following cleavage, but in certain preferred embodiments no end-repair step is performed. Adapters can be added to one or both ends of the target fragment. In certain preferred embodiments, an adapter is added to the double-strand break prior to or after Cas9 cleavage so that the resulting target fragment has an adapter sequence at a first end and the Cas9 cleavage at a second end. The adapter added to the first end may be specific for the target fragment or may be added to all double-strand breaks in the sample that are compatible with the adapter and ligation reaction. Optionally, a second adapter can be added to the Cas9 cleavage site. In some preferred embodiments, end repair is performed only at one end of the target fragment, i.e., after a first cleavage and prior to a second. For example, end repair can be performed after a restriction digest to create blunt ends that can ligate to a first adapter to be linked to all double-stranded ends. Subsequently, a Cas9 cleavage reaction is performed and the cleavage products are not subjected to end repair prior to addition of a second adapter. Since Cas9 cleavage typically produces blunt ends, end repair may simply not be needed for ligation of blunt-ended adapters.

Adapters at opposite ends of a target fragment may be the same at both ends, but are preferably different to allow for different functionalities at the ends, e.g., primer binding sites (e.g., for amplification and/or sequencing), barcodes, cleavage sites (e.g., for cloning or addition of further adapter sequences), modified nucleotides, complementarity to oligonucleotides for affinity purification, etc. Other functionalities that can be incorporated into adapter sequences are described in U.S. Pat. No. 7,901,889 and U.S. Patent Publication No. 2015/0118685, both of which are incorporated herein in their entireties. For example, in some asymmetric templates, one adapter has a primer binding site and the other adapter has a sequence complementary to an oligonucleotide linked to a bead or other surface for subsequent capture of the target fragment. The complementary sequence in the adapter is designed to provide tight and specific binding to the surface/bead-linked oligonucleotide. Preferably the adapter does not bind to other nucleic acids in the sample, e.g., other fragments or adapters; nonspecific binding to the sample nucleic acids can be mitigated by performing the hybridization at a non-denaturing temperature so the double-stranded fragments do not denature and are therefore not available to hybridize to the adapters. In specific embodiments, a polyA sequence is present in an adapter linked to a target fragment and a polyT oligonucleotide is linked to a bead, e.g., a magnetic bead. To ensure the adapters are different at both ends of the target region, they can be ligated at different times, e.g., one before Cas9 digestion and the second following Cas9 digestion. Alternatively, the ends produced by the fragmentation can be different than those produced by Cas9 cleavage, and each adapter can be designed to be specific for only one type of end, e.g., blunt end, 3' overhang, or 5' overhang. Further, one or both adapters added to the target fragment can be stem-loop/hairpin adapters. Adding adapters that are not susceptible to exonuclease digestion to both ends, whether they are the same or different adapters, provides an added benefit where subsequent enrichment steps use exonuclease digestion since only fragments capped by undigestible adapters will survive the treatment. For example, hairpin adapters have no free nucleic acid termini so cannot be degraded by exonucleases. Modified nucleotides at the ends of linear adapters can also be resistant to exonuclease digestion. Such methods for exonuclease-based removal of non-target fragments are further discussed below.

In some embodiments, a large target fragment is cleaved by Cas9 to produce a smaller target fragment and a non-target fragment. When the cleavage is followed by adapter ligation to the Cas9 cleavage products, it is possible that both the target and non-target fragments will be linked to the adapter since both comprise Cas9 cleavage sites at one end. In practice, however, the fragment comprising the sequence complementary to the sgRNA or crRNA tends to be enriched at a lower level than the fragment on the other side of the cleavage location. As such, the targeting RNAs are designed to ensure that the binding of the sgRNA or crRNA occurs with the 3' end of the RNA nearest the target region, which places the region that hybridized with the targeting RNA on the non-target fragment produced by the cleavage. Results from enrichment experiments show that enrichment of the non-target fragment is lower than the target fragment when the targeting RNA is oriented in this manner. Although not wishing to be bound by theory, there are several reasons for the uneven enrichment of the fragments flanking the Cas9 cut site. First, the ligation of the adapter to the Cas9 cleavage product may be less efficient on the side of the cleavage that is bound to the RNA-Cas9 complex. Second, where the non-target fragment is small, subsequent loading onto a sequencing instrument may be less efficient. This has been observed for PacBio® sequencing instruments when loaded using magnetic beads. In some embodiments, non-target fragments that do receive the adapter specific for the Cas9 cut site could be subjected to further cleavage to ensure their size is small enough to limit loading and, therefore, subsequent sequencing. Additionally, they could be cut and subjected to exonuclease degradation to remove them from the mixture. Further, it was surprisingly found that addition of heparin to the Cas9 cleavage reaction enhanced the bias toward enrichment of the target fragment over the non-target fragment. As such, in certain preferred embodiments, heparin in included in the Cas9 cleavage reaction, e.g., at a concentration ranging between 1-15 µg/µl, and more preferably between 1-10 µg/µl.

Although the double-strand break introduced by the nuclease activities of Cas9 is predominantly a blunt cut, but the position of the cut on the noncomplementary strand can be altered by changing the length of a linker (variable sequence) between the PAM and the region of the foreign DNA complementary to the crRNA. This variable region is often included in the definition of the PAM sequence, but it is not a conserved sequence and is also sometimes referred to as a "linker" between the conserved PAM sequence and the complementary region. As noted above, the Cas9 endonuclease has two separate nuclease domains: the HNH nuclease domain cleaves the strand complementary to the crRNA, and the RuvC-like nuclease cleaves the opposite strand of the foreign DNA, and the two domains select their cleavage sites in different ways (Chen, et al. (2014) J. Biol. Chem., "Cut Site Selection by the Two Nuclease Domains of the Cas9 RNA-guided Endonuclease," doi:10.1074/jbc.M113.539726, which is incorporated herein by reference in its entirety for all purposes. Specifically, the HNH domain catalyzes cleavage of the complementary strand at a fixed position, i.e., always three nucleotides from the 5'-end of the complementary region, independent of linker length. In contrast, the RuvC-like domain catalyzes cleavage of the non-complementary strand a certain distance from the PAM site, with cleavage occurring four to five nucleotides from the PAM site with a one-nucleotide linker, and five nucleotides from the PAM site with a linker of two or more nucleotides. As such, a 3' overhang is produced by Cas9 cleavage where a longer linker is present between the PAM site and the complementary region. Optionally, the fragments generated can be subjected to a size selection procedure to further enrich for the desired target sequence. Further, where it is desired to have blunt-ended fragments, the overhangs can be removed by addition of a single-strand-specific exonuclease.

In certain preferred embodiments, an increased stability of the sgRNA, tracrRNA, and crRNA molecules is achieved by addition of RNase inhibitors, which prevent degradation of the RNAs by enzymes that specifically degrade RNA, i.e., RNases. Such inhibitors are known to the ordinary artisan and routinely used in the art. Addition of RNase inhibitors is especially beneficial in embodiments in which a moiety on an RNA molecule is used to isolate the RNA-Cas9-target region complex. For example, the moiety can be an sgRNA-linked affinity tag, as described elsewhere herein. The presence of one or more RNase inhibitors serves to increase the stability of the complex comprising the RNA and target nucleic acid during the capture of the complex, thereby increasing the yield of the enrichment. Yet further, targeting RNAs can comprise modified bases that enhance their stability, and potentially enhance the amount of Cas9 cleavage at the desired location. This can be accomplished where a targeting RNA has modifications at one or both ends that protect the molecule from degradation. Chemical modifications that can be used include, but are not limited to 2'-O-methyl modifications, 2'-O-methyl-3'-phosphorothioate modifications, and 2'-O-methyl-3'-thioPACE (phosphonoacetate) modifications, as long as the presence of the modification does not interfere with association of the targeting RNA with Cas9 endonuclease or sequence-specific binding to the sample nucleic acid. These can be used at one or both ends of a targeting RNA, and the same or different modifications can be present at each end. These and other modifications are further described in the art, e.g., in Hendel, et al. (2015) Nature Biotechnology, doi:10.1038/nbt.3290.

As noted above, the fragments produced by cleavage of sample nucleic acids, e.g., by Cas9-cleavage and/or restriction digestion, can be further processed to add adapters for different purposes, e.g., sequencing, cloning, amplification, barcoding, etc. Briefly, these adapters can be the same on both sides, as is typically the case when the Cas9 cleavage produces blunt ends at both sides of a target fragment. Alternatively, where the ends of the target fragment are different, e.g., where Cas9-cleavage produces one or two overhangs or where the fragment is cut by Cas9 on one end and a different endonuclease at the other end, different adapters can be designed for each end. These adapters can comprise different functionalities for use in subsequent steps, e.g., restriction sites, primer binding sites, affinity tags, and the like. Such adapters can be single-stranded or double-stranded, or may comprise both single- and double-stranded portions, e.g., in a hairpin/stem-loop conformation. Methods for linking single-stranded or double-stranded oligonucleotides to the ends of nucleic acid fragments are well known to those of skill in the art, and include ligation and PCR-based methods. Such methods and exemplary stem-loop adapters are further described in U.S. Pat. No. 8,153,375, which is incorporated herein by reference in its entirety.

In certain embodiments, as noted above, excised target regions are protected from nuclease digestion by ligating adapters to the ends of nucleic acid fragments comprising the target regions. These adapters can have modified termini that are not susceptible to nuclease digestion, or can be structured so that the resulting molecule is not a substrate for nuclease digestion. In certain preferred embodiments, stem-loop (a.k.a. "hairpin") adapters are used. These adapters are single-stranded, but their termini are complementary such that the adapter folds back on itself to generate a double-stranded portion and a single-stranded loop. Where stem-loop adapters are linked/ligated to both ends (e.g., following optional end repair in which any gaps have been filled), subsequent treatment with exonuclease enzymes will degrade non-target fragments that do not comprise the adapters, thereby further enriching the mixture for the target fragments. This exonuclease treatment can be performed instead of or in addition to a size-selection process to further enrich for the target region. The length of the original double-stranded nucleic acid to which the adapters are added can vary, but is preferably at least 200, 500, 1000, 3000, 5000, 7000, 10,000, 15,000, or 20,000 base pairs in length. The length depends primarily on the intended use, and in some embodiments is based upon the average read length in a sequencing technique to be used. In certain embodiments, such as for redundant sequencing applications, the length of the insert is less than the average read length to allow repeated sequencing of the molecule, e.g., in a "rolling-circle" manner, by a single polymerase enzyme. Methods for redundant sequencing of nucleic acid templates are further described in detail in U.S. Pat. Nos. 8,153,375, 7,901,889, and 7,476,503, all of which are incorporated herein by reference in their entireties.

Alternatively or in addition, such adapters can comprise affinity tags that can be used to capture the target fragments. Affinity tags are covalently or non-covalently linked to the molecules of interest and used to purify such molecules from a sample using an affinity technique. For example, an affinity tag can be incorporated into adapter that is linked to the end of a target fragment. The affinity tag further binds to an immobile phase, e.g., a substrate or matrix (e.g., within a column). Once bound, the substrate or matrix is washed to remove all unbound components of the sample leaving only those bound via the affinity tag, thereby enriching the target molecules and removing non-target molecules. Affinity tags are known and frequently used in the art, and specific examples are further described elsewhere herein.

In certain embodiments, the adapters can have primer sequences pre-hybridized to them prior to ligation, e.g., where the fragments are to be subjected to a primer extension reaction (e.g., PCR, sequence-by-synthesis reaction, etc.). However, such primers must be configured to survive any treatments performed on the nucleic acid sample prior to the primer extension reaction. For example, where a nuclease treatment will be performed the primer must be resistant to degradation, but still able to be extended, e.g., in a polymerization reaction. In alternative preferred embodiments, primer is not present on the adapter during the ligation reaction, but is added later, e.g., prior to the primer extension reaction. Methods for producing such double-stem-loop nucleic acid molecules are provided, e.g., in U.S. Pat. No. 8,153,375, which is incorporated herein by reference in its entirety for all purposes. For ease of discussion, most embodiments herein refer to stem-loop adapters to protect the ends of a target fragment, but it will be understood that stem-loop adapters are but one example of adapters that can be used in the methods herein.

One or both adapters can have primer binding sites, and during a subsequent primer-extension reaction primers on one or both adapters may be extended. In preferred embodiments only one primer is extended even in cases where two are present. The primers may hybridize to the "loop" portion of a stem-loop adapter, to a site within the target region, or may overlap the junction between an adapter and the target region, hybridizing to at least a portion of both. In some embodiments, after stem-loop ligation and, preferably, after any nuclease degradation of non-target strands, the remaining fragments having stem-loop adapters at both ends are treated to denature the double-stranded target fragment. This treatment results in a single-stranded circle comprising both strands of the double-stranded fragment separated by the adapter sequences: . . . adapter 1—target strand 1—adapter 2—target strand 2 . . . , where each target strand is flanked by the two adapter sequences in a circular configuration. Denaturation of the target region renders the 5' end that is complementary to the primer available for primer binding. Since the primer will serve as an initiation point for extension if the 3' end is annealed to the target fragment, this provides a further selection for the target fragment. That is, even if some of the non-target fragments are ligated to adapters at both ends, it is extremely unlikely that they will also have a 5' end that is identical to that of the target fragment. As such, they will not support extension of the primer, even though the primer may anneal at its 5' end to the adapter sequence. As a result, where the sequencing of these fragments requires primer-extension, no sequence data will be generated from the non-target fragments.

Yet further, primers can comprise modified bases that enhance hybridization to the adapters and/or target fragments. For example, such modified bases can facilitate primer binding to a double-stranded sequence even without prior denaturation, e.g., by strand invasion. This can be accomplished where a primer binds more strongly than the complementary strand of the target fragment, for example, where it comprises modified nucleotides such as PNA (peptide nucleic acid) nucleotides, LNA (locked nucleic acid) nucleotides, O-methyl-modified nucleotides, and other modified nucleotides known in the art that have a greater affinity to a complementary base than does a canonical nucleotide. In further embodiments, known recombination enzymes can also be present to facilitate strand invasion, e.g., E. coli RecA and RecT proteins, yeast Rad 51 and Rad52 proteins, human splicing factor PSF, protein β from phage lambda, and other enzymes including helicases and single-stranded DNA binding proteins. Strand invasion can be further facilitated by addition of other protein factors, e.g., single-strand binding proteins such as E. coli SSB protein. Primers that are to be annealed prior to a nuclease degradation step are preferably resistant to the digestion, e.g. due to having a blocking group on any susceptible termini, or by using nucleases that do not cleave at a double-stranded/single-stranded junction. Where one or more endonucleases are used for the digestion, the annealing of the primer preferably does not create a recognition site for the endonuclease(s). Further, such primers can comprise affinity tags to allow capture of the target fragments, e.g., on a solid surface, as described elsewhere herein. In some embodiments, primers are heated prior to hybridization to a primer binding site, which can ensure that any secondary structure is removed, increasing the availability of the full length of the primer to bind to the primer binding site.

IV. Additional Methods for Capture of Target Nucleic Acids

Although the methods herein do not require amplification of the target nucleic acid, the sample nucleic acids can be amplified prior to the enrichment. Where stem-loop adapters are to be added to the nucleic acids prior to enrichment, the amplification can be carried out either before or after addition of the adapters. If performed prior to addition of the adapters, any standard amplification method will work, e.g., any of a number of different types of PCR known in the art. Where the amplification is to be performed after addition of the adapters, a single-stranded circular molecule formed by adding hairpin adapters to both ends of a double-stranded linear nucleic acid can be subjected to rolling circle amplification to generate a strand comprising multiple complementary copies of the single-stranded circle. This process increases the amount of target nucleic acid available for further analysis, which can be especially important where the amount of the original sample nucleic acid is extremely limiting. The rolling-circle mode of amplification is preferable to conventional PCR, the latter of which can introduce and perpetuate changes in the population of amplicons generated that cannot be distinguished from true variants in the original template strands. In contrast, rolling-circle replication creates multiple complementary copies of the original template, and while it is possible that changes can occur during synthesis, these changes are not perpetuated since the newly synthesized strand is not used as a template strand. As such, any random changes introduced will not be replicated in additional molecules, and true variants will be readily distinguishable. A preferred polymerase for rolling-circle amplification is Phi29 (129) DNA polymerase, which has an extremely long read length. Such amplification can be performed using the whole genomic sample, e.g., after addition of the stem-loop adapters but prior to any enrichment, or used at a later stage in the enrichment process, and is applicable to extremely small amounts of sample nucleic acids, e.g., 1-10 ng quantities. Further information on rolling-circle amplification of double-stranded nucleic acids having terminal stem-loop adapters is provided in U.S. patent application Ser. No. 14/208,451, filed Mar. 13, 2014, and incorporated herein by reference in its entirety for all purposes.

In certain preferred embodiments, additional enrichment for a target region initially isolated by other methods described herein, e.g., using bis-PNA clamps or Cas9 cleavage, can be achieved through the methods described in U.S. Pat. No. 8,658,364, which is incorporated herein by reference in its entirety for all purposes. Certain methods and compositions described therein are directed to isolating nucleic acids or polymerase-nucleic acid complexes, and utilizing the ability of a polymerase having strand displacement activity to open up a double-stranded region (e.g., the "stem" of a stem-loop structure and/or a double-stranded target region) to expose a sequence within the double-stranded region, i.e., to render it single-stranded. This single-stranded sequence is targeted and captured using a "capture-hook" oligonucleotide that is complementary to the sequence. Once a polymerase begins to unwind the double-stranded portion by synthesizing a nascent strand using a first strand of the duplex, the sequence on the second strand of the duplex is rendered single-stranded, and this is the strand that is complementary to the capture-hook oligonucleotide; since it is now single-stranded, it is available for hybridization to the capture-hook molecule. This method provides a further enrichment where the capture-hook oligonucleotide is complementary to a sequence specific to the target fragment, since other non-target molecules that survived the nuclease digestion are unlikely to also comprise the target-specific sequence and so will not anneal to the capture-hook oligonucleotide. To expose enough of the target fragment to ensure adequate specificity, the polymerase may open the double-stranded region of the target fragment at least 10, 20, 30, 40, or even 50 bases, and the capture-hook oligonucleotide can be complementary to all or only a portion of the opened target region. In alternative embodiments, such as where the practitioner wishes to capture all the fragments having stem-loop adapters, the capture-hook oligonucleotide can anneal to a portion of a stem-loop adapter and not to any part of the target region. As such, all nucleic acids having the stem-loop adapter could bind to the capture-hook oligonucleotides, regardless of whether or not the nucleic acid comprised the target region, and be isolated from nucleic acids that do not bind to the capture-hook oligonucleotides. This strategy is preferred where the previous steps (e.g., Cas9 cleavage, bis-PNA binding, size-selection, exonuclease degradation of non-target, etc.) are sufficient to provide the level of enrichment required for subsequent steps, e.g., amplification, cloning, sequencing, etc.

The capture-hook molecule is typically able to be linked to a solid surface (e.g., a bead or column) to allow the target fragment to be immobilized. In certain preferred embodiments, the capture-hook oligonucleotide comprises a region complementary to an oligonucleotide bound to a bead or other surface. For example, the capture-hook oligonucleotide can comprise a polyA region that can bind to a polyT region of a magnetic-bead-bound oligonucleotide. Typically, the sequence for the surface-bound oligonucleotide is chosen to be a sequence that is not complementary to the target fragments. Only those polymerase-nucleic acid complexes hybridized to a "capture-hook" oligonucleotide are captured on the magnetic beads/other surface, and the non-target fragments can then be removed by standard methods, e.g. washing. The target fragments are subsequently removed from the capture-hook oligos and subjected to further analysis, e.g., sequence analysis.

In certain embodiments, target regions flanked by stem-loop adapters are bound to primers complementary to the target region and/or adapters, and pre-extension of the primers prior to capture of the target fragments serves to further stabilize the complex and increase the yield of captured target fragments. To facilitate primer annealing within the target region, the adapter-flanked molecule is optionally subjected to a treatment that separates the complementary strands of the double-stranded insert to allow binding of one or more oligonucleotide primers that are complementary to one or more target regions of interest in the original sample nucleic acids. Following the specific annealing of the primers to the target regions and/or adapters, primer extension is carried out in the presence of biotinylated (or otherwise affinity tagged) nucleotide analogs such that the nascent strand generated comprises biotin tags (or other affinity tags) that can be used in a subsequent affinity purification step. For example, only the constructs that have a tagged extension product will be immobilized, e.g., on a bead, surface, column, etc., that is coated with a binding partner for the tag. For example, to immobilize a biotin-tagged product, a bead coated with avidin or streptavidin can be used. Nucleic acids that are not immobilized or "captured" are removed by conventional methods, e.g., washing/buffer exchange, spin column, chromatography, etc. Once isolated, the biotin-tagged extension product can be removed, e.g., by denaturation. Where a oligonucleotide primer is specific for a target region, either through hybridization to the target region or to an adapter selectively linked to the target region (e.g., an adapter specifically linked only to Cas9 cleavage sites or a target-specific overhang sequence), the resulting isolated nucleic acid pool is enriched for the target. This enriched pool is subsequently subjected to further analysis, e.g., sequencing, preferably with no amplification and/or removal of the adapter sequences. Optionally, addition of the sequencing primer can occur coincident with addition of a polymerase enzyme, resulting in a template/primer/polymerase enzyme complex that is appropriate for a sequencing-by-synthesis reaction.

Although certain methods provided herein describe linking of stem-loop adapters to both ends of a double-stranded sample nucleic acids, in some embodiments only one end is linked, which will also preserve the connection between both strands of the original nucleic acids. In fact, neither end needs to be linked to a stem-loop adapter if this connection is not needed or desired. In some embodiments, the connection can be maintained by adding barcode adapters to one or both ends. The sequence of the barcode detected during subsequent sequencing reactions can be used to link the data from the two strands during data analysis in embodiments in which both strands are targeted by the oligonucleotide probes and sequenced separately. In yet further embodiments, only a single strand is isolated and sequenced, and the sequence of the other strand is determined based on the complementarity between the two strands. In some embodiments, e.g., where modifications need not be preserved for further analysis, the enriched nucleic acids can be subjected to amplification to increase the total amount of nucleic acid in any subsequent procedures. For example, primer-binding sites in adapter regions can be used to PCR amplify the portion of the nucleic acid construct that they flank.

As noted above, more than one probe (e.g., bis-PNA clamp, sgRNA, or crRNA:tracrRNA) can be used to select desired regions of a nucleic acid sample. In some embodiments, one probe anneals to a first strand of a region of interest and a second probe anneals to the complementary strand. Alternatively or in addition, probes can target different regions within a single contiguous nucleic acid sequence, e.g., along a single gene, chromosome, regulatory region, repeat region, and the like. Yet further, probes can target multiple different regions that share a characteristic of interest, e.g., involvement in a biologic pathway (e.g., metabolism, transcriptional regulation, carcinogenesis, endocrine response, etc.) under investigation. Primers can also target specific alleles of interest, e.g., by being complementary to one or more SNP positions known to be within the particular allele of a gene. These primer targeting methods can be used in combination, as well. Further, the methods herein may be usefully combined with those of U.S. Patent Publication Nos. 20060040300, 20080090733, and 20090263798, the disclosures of which are incorporated herein by reference in their entireties for all purposes.

Many types of affinity tags can be used in the tagged adapters of the invention. Preferred affinity tags that covalently associate with their binding partner include those known to those of ordinary skill in the art. While covalent interactions are preferred, highly stable non-covalent interactions are also contemplated for use with the methods herein, including but not limited to, biotin (which binds to avidin, traptavidin, and streptavidin), and others. Stable, non-covalently associating binding pairs can include, but are not limited to, antibodies that stably bind their antigens and protein receptors that stably bind their binding partners. For example, in certain embodiments, a protein that specifically binds to a sequence of an adapter serves as a "tag" and an antibody for that protein is immobilized on a bead or other solid surface. Binding of the antibody to the protein immobilizes the adapter and any fragment ligated thereto. Proteins that bind to specific sequences in nucleic acids include, e.g., transcription factors, repressors, methyltransferases, etc. Yet further, affinity tags also include hybridization-based tags, such as oligonucleotides complementary to immobilized or immobilizable nucleic acids. Various types of affinity tags are also discussed in greater detail in U.S. Pat. No. 7,745,116, U.S. Provisional Application No. 61/721,206, filed Nov. 1, 2012, U.S. patent application Ser. No. 14/068,293, filed on Oct. 31, 2013; U.S. patent application Ser. No. 13/427,725, filed on Mar. 22, 2012; all of which are incorporated herein by reference in their entireties for all purposes.

Depending upon the concentration of the nucleic acid sample to be subjected to the enrichment procedures described herein, it may be beneficial to add non-target "carrier" nucleic acids to enhance the nuclease and/or ligase reaction, especially where the enrichment procedures are inefficient when the total amount of nucleic acids in the mixture is too low. By addition of non-target nucleic acids, the concentration of the nucleic acid sample is raised to increase the efficiency of one or more steps of the method. Ironically, addition of carrier effectively "un-enriches" the sample for the target region prior to the enriching procedure, however, can result in production of a more enriched sample by the end of the procedure. In preferred embodiments, the carrier is designed to be present during the steps that require higher nucleic acid concentrations, but not to interfere with subsequent analysis of the target nucleic acids, e.g., by sequencing, amplification, etc. For example, the carrier can be a circular nucleic acid to which adapters cannot be ligated or much smaller than the target region so that it is lost during size selection. It may also lack certain sequences that are required for subsequent steps, e.g., primer-binding sites needed for sequencing; as such, it may be present in the subsequent steps, but would not interfere with analysis of the target region. In certain embodiments, the carrier preferably lacks recognition sites for endonucleases used to generate the cuts flanking the target region or for attachment of adapters needed in subsequent steps, and/or comprises recognition sites for endonucleases used to degrade non-target nucleic acids. In some embodiments, these additional non-target nucleic acids are linked to affinity tags to allow their efficient removal from the nucleic acid sample once there is no more need for a higher nucleic acid concentration. In some embodiments, the carrier nucleic acids lack an affinity tag that is linked to target fragments, so that they can be removed with other non-target nucleic acids during the enrichment procedure. Different types of carrier nucleic acids are known and used in the art, e.g., DNA from lambda phage, plasmid DNA, synthetic oligonucleotides, etc. In certain embodiments, a double-stranded circular carrier is used, e.g., plasmid DNA. Preferably, the double-stranded circular carrier is treated prior to use with one or more exonucleases to ensure there are no 3' or 5' ends that could interfere with the enrichment procedure, e.g., by linking to adapters intended for the nucleic acids being enriched. This also ensures that the carrier will not be degraded in any exonuclease treatments that may be included in the enrichment process. Preferably, the carrier does not comprise nucleic acid sequences that are selectable in (or would otherwise interfere with) the enrichment procedure, e.g., by being identical to target sequences, driver sequences, or oligos (e.g., comprising homopolymer regions) linked to substrates used to pull down the target fragments. The target fragments can be purified away from the remaining carrier molecules by virtue of an affinity tag or driver-hybridization procedure, or, optionally or in addition, by specific cleavage of the carrier once it is no longer needed, followed by exonuclease digestion.

Following the enrichment procedure, the pool of fragments enriched for the target region can be subjected to further manipulations, such as cloning, amplification (e.g., by PCR, isothermal amplification, rolling-circle amplification, etc.), removal of adapter sequences from one or both ends, addition of adapter sequences to one or both ends, sequencing (e.g., single-molecule sequencing, Illumina® sequencing, pyrosequencing, etc.), further purification and/or size selection (e.g., by gel, column, etc.), and other nucleic acid manipulations known to those of ordinary skill in the art.

Various methods can be used to determine the effectiveness of the enrichment procedure. For example, in certain preferred embodiments, relative fold-enrichment is calculated by the following steps. First, the ratios of [target fragments]/[non-target fragments] for the sample prior to enrichment is estimated. In some cases, the ratio for the original sample (i.e., pre-enrichment) is based on the theoretical digestion by the restriction endonuclease(s) used, assuming 100% digestion efficiency and that all four canonical bases are evenly distributed in the sample (e.g., 25% of each). Alternatively or additionally, where sequence data for the entire sample is available, the ratio of target:non-target fragments can be based on the number of sequencing reads mapped to the target region over the total number of sequencing reads for the sample. The ratio for the enriched sample is based on sequencing data generated using the enriched sample, and is preferably computed as the number of sequencing reads mapped to the target region divided by the total number of sequencing reads in all. In alternative embodiments, the number of sequencing reads mapped to the target region can be compared to those mapped to the non-target regions in the sample. The fold-enrichment is calculated by dividing the ratio for the enriched sample by the ratio for the non-enriched sample.

Determination of a specific yield of the fragments capped at both ends by an adapter in the enriched sample can comprise use of various commercially available nucleic acid quantitation systems, e.g., spectrophotometry or fluorimetry (e.g., using a Qubit® system). The measure of the amount of double-stranded nucleic acids in the enriched sample relative to the total amount of nucleic acids in the non-enriched sample is one measure of the yield of fragments provided by the enrichment method. However, this yield may include some quantity of non-target fragments that have also been ligated to two adapters, so will not necessarily reflect the amount of target fragments that are recovered.

V. Applications

Target sequences captured using the methods provided herein can be used directly in further analytical reactions, e.g., sequencing reactions, or can be subjected to further manipulations such as amplification, cloning, and the like. For example, where the fragments captured are single-stranded nucleic acids, a complementary strand can be generated, e.g., by random primed synthesis or using specific primers that bind to adapters at the ends of the fragments. Such adapters can be added before or after capture, but are preferably added prior to denaturation and sequence capture.

Capture of target nucleic acids facilitates targeted sequencing of specific regions of a genome, chromosome, metagenomic, or other nucleic acid sample. Further, since it is desirable to retain base modifications (e.g., methylation, adenylation, damaged bases, glucosylated bases, etc.) present in a sample nucleic acid molecule for further analysis (e.g., direct detection during a sequencing reaction), capture methods that do not rely on amplification of the sample nucleic acids are of particular interest. Where nucleic acids from different sources are to be pooled prior to further analysis, barcode adapters specific for each source are preferably linked to all nucleic acids from that particular source. This allows identification of the source of a particular sequence read from a subsequent pooled sequencing reaction by virtue of detecting the sequence of a barcode identifying the source. This multiplexing can combine various types of sources, e.g., different individuals in a population, different tissues in an individual, different portions of a genome, different viral subpopulations, and the like.

Many research and diagnostic assays require sequence information for a particular locus of interest or just a few loci in a large number of individual samples. Sequencing a full genome, especially a large genome like the human genome, for each of multiple samples (e.g., from patients, subjects from case-control studies, etc.) in order to sequence the locus of interest is not economically feasible. Therefore, an efficient and cost-effective targeting method for enrichment of the region of interest, e.g., a region useful for diagnostic applications, in a complex genome is desirable and is provided by the instant application. It is also particularly challenging to provide enriched targeted templates for sequencing that comprise native DNA for epigenetic study since many reported target enrichment methods require some DNA amplification or cloning before, during, or after the enrichment (hybrid capture, PCR amplification, molecular-inversion-probes selection, etc.). In some cases, the goal of a study is the identification of rare mutations or counting the number of repeats in a repeat region of interest, and since PCR amplification is known to introduce errors into the resulting amplicons and has difficulty producing amplicons from highly repetitive nucleic acids, it can complicate the identification of true sequences in the original sample.

Isolation of molecules containing a region of interest that exists in low concentrations in a highly complex sample is challenging, and often there is not enough enriched nucleic acid to perform the additional analyses, e.g., sequencing, without PCR amplification. The instant invention provides enrichment methods for one or more single genomic regions or loci of interest from a complex sample, e.g. a whole genome sample, without any amplification required. In preferred embodiments, the enriched templates are native DNA that can be used for mutation detection, allelic difference determination, and direct methylation analysis by SMRT® Sequencing, e.g., as further described in U.S. Patent Publication No. 2011/0183320, incorporated herein by reference in its entirety for all purposes.

The enriched compositions described herein are particularly useful in nucleic acid sequencing reactions, e.g., polymerase-mediated, template-dependent synthesis of nucleic acids, which can be observed using real-time techniques for a variety of desired goals, including in particular, determination of information about the template sequence. A number of methods have been proposed for determination of sequence information using incorporation of fluorescent or fluorogenic nucleotides into the synthesized strand by a DNA or other polymerase, and the compositions of the invention are applicable to these methods. While several of these methods employ iterative steps of nucleotide introduction, washing, optical interrogation, and label removal, preferred uses of these compositions utilize "real-time" determination of incorporation. Such methods are described in detail in, for example, U.S. Pat. Nos. 7,056,661, 7,052, 847, 7,033,764 and 7,056,676, the full disclosures of which are incorporated herein by reference in their entirety for all purposes.

Briefly, such methods observe an immobilized polymerase/template/primer complex as it incorporates labeled nucleotide analogs. Using optical techniques that illuminate small volumes around the complex with excitation radiation, e.g., TIRF methods, optical confinements like Zero Mode Waveguides (ZMWs) (See, U.S. Pat. Nos. 6,917,726, 7,013,054, 7,181,122, 7,292,742 and 7,170,050 and 7,302,146), and the like, one can identify incorporation events based upon the optical signature of their associated fluorophore, as compared to non-incorporated, randomly diffusing labeled nucleotide analogs. By providing each different type of nucleotide with a distinguishable fluorescent label, e.g., having a distinguishable emission spectrum, one can identify each base as it is incorporated, and consequently read out the sequence of the template as the nascent strand is created against it.

An alternative real-time sequencing method that can be used with the methods provided herein is nanopore-based sequencing, e.g., as described in U.S. Pat. Nos. 6,267,872 and 6,355,420; U.S. Patent Publication Nos. 2014/0061048 and 2007/0298511; International Patent Application Nos. WO2000028312(A1) and WO2001059453(A2); and Kasianowicz, et al. (1996) Proc. Natl. Acad. Sci. USA 93: 13770-13773, all of which are incorporated herein by reference in their entireties for all purposes.

In certain embodiments, the methods herein can be used to enrich target fragments comprising regions having diagnostic utility in patient management, e.g., for subsequent analysis that can determine an individual's risk of developing a genetic disease or disorder. For example, the methods herein are useful for enriching target nucleic acids having highly repetitive sequences. Some highly repetitive regions have been linked to repeat expansion disorders, such as Fragile X syndromes, Huntington disease, Amyotrophic lateral sclerosis (ALS), myotonic dystrophy type 1, Alzheimer's disease, and spinocerebellar ataxias, which are of great interest to researchers seeking to better diagnose an individual to determine their risk of developing such a disorder, and potentially informing on an appropriate treatment for the individual. In specific applications, sequencing of a target fragment provides clinically reportable end-points that can include one or more of the following metrics/characteristics: size of the repeat region, the number of repeats within the region, haplotype of the entire region for both the maternally and paternally derived chromosomes, more than two genotypes in a diploid individual resulting from mosaicism/somatic variability, epigenetic analysis to determine sites of base modifications, e.g., within the repeat region and/or the promoter region of a gene comprising the repeat region, and sequence interruptions (e.g., where a repeat within the repeat region has a single-base substitution). Sequence interruptions are particularly interesting where they impact diagnostic reporting and clinical outcomes. For example, in the FMR1 gene, which is associated with Fragile X syndrome, the expanded CGG repeat region is known to contain AGG triplets, which are useful in determining "anticipation" in the offspring of an individual, which is a measure of the statistical likelihood that an offspring of the individual will have an expanded repeat region of a size associated with the clinical disorder. Typically, the larger the number of repeats in a maternal or paternal gene, the more likely the offspring of the individual will have a full mutation, defined as having 200 or more repeats, and will exhibit characteristics of the disease, which can intellectual, behavioral, and developmental disabilities. However, the presence of interrupting AGG trinucleotides within the CGG repeat tract of the FMR1 gene have been found to "stabilize" the gene and decrease the likelihood that the repeat tract will be further expanded during meiosis, thereby lowering the risk that the offspring will have a full mutation. As such, knowing where and how many AGG trinucleotides are in an individual's FMR1 gene is helpful to determine their risk of having a child with Fragile X syndrome, and is therefore a useful diagnostic for genetic counseling prior to conception.

As noted above, some implementations of the methods herein isolate target regions having sites that may have epigenetic modifications. Following enrichment, sequencing of these target regions can determine the location and type of such modifications. In particularly preferred embodiments, SMRT® sequencing is used to sequence the target regions and identify the epigenetic modifications present therein, since the SMRT® sequencing methodology uses a kinetic detection method to detect many different types of epigenetic modifications during the standard sequencing reaction. Preferably, the sample nucleic acid is not amplified prior to the sequencing reaction, since amplification typically produces amplicons that lack the epigenetic modifications. Identification of epigenetic modifications within unamplified DNA (e.g., genomic DNA) can identify imprinting in an individual, where one allele is methylated and the other is not resulting in parent-of-origin-specific gene expression. The analysis and diagnosis of diseases and disorders due to imprinting and/or other parent-of-origin-dependent expression patterns is contemplated and has been linked to a multitude of phenotypes, e.g., Beckwith-Wiedemann syndrome, Alzheimer disease, mitochondrial disorders/syndromes, metabolic disorders, autism, bipolar disorder, diabetes, male sexual orientation, aging, obesity, and schizophrenia; as well as a number of cancers: bladder, breast, cervical, colorectal, esophageal, hepatocellular, lung, mesothelioma, ovarian, prostate, testicular, and leukemia, among others (Falls et al, Genomic Imprinting: Implications for human disease. Am J Pathol 154: 635-47, 1999; Jirtle, Genomic imprinting and cancer. Exp Cell Res 248: 18-24, 1999; Simmons, et al. (2008) Nature Education 1(1); Takasugi, et al. (2010) BMC Genomics 11:481; and Barres, et al. (2011) Am J Clin Nutr 93(4):8975-9005, the disclosures of which are incorporated herein by reference in their entireties for all purposes). Additional information on imprinting is provided in Sleutels, et al. (2002) Advances in Genetics 46, 11-163.

Epigenetic modifications in a regulatory region, e.g., a promoter region, can affect gene expression and/or subsequent post-transcriptional modification, e.g., splicing of the mRNA transcripts. Alternative splicing patterns can result in the production of aberrant polypeptide products, and can thereby be the disease mechanism in certain disorders, such as repeat expansion disorders. As such, it is of interest to be able to map the chromosomal locations of epigenetic modifications with their identification serving as a prognostic or diagnostic for certain disorders, e.g., to inform as to the susceptibility or resistance of an individual to such disorder, the expected severity of the disorder, the expected age-of-onset of the disorder, and/or preferred theranostic strategies that could prevent or lessen the severity of the disorder.

Identification of epigenetic modifications can also identify "boundary genotypes," expansions that are on the boundary of clinical genotype reporting. For example, an FMR1 gene having 195 copies is not considered a full mutation since it is less than 200 copies, but it is known that methylation-directed inactivation of the FMR1 gene is involved in causing the disease phenotype. As such, an FMR1 allele that has only 195 copies, but is also methylated, may be clinically relevant to report as a Fragile X positive allele, whereas an FMR1 allele that has 195 copies and is not methylated may be reported as a Fragile X negative allele. Yet further, methylation reporting may be an independent diagnostic end-point for repeat expansion alleles and upstream promoter regions, as well.

Pseudogenes are gene-like sequences in a genome that are not expressed, e.g., are not transcribed or their transcripts are not translated. They are characterized by their similarity to known genes, and are often labeled as "junk DNA." They also frequently display methylation patterns that differ from their active gene counterpart, as shown, e.g., in Cortese, et al. (Genomics 91(6):492-502 (2008)), incorporated herein by reference in its entirety for all purposes. As such, the generation of both modification data and polynucleotide sequence data in a single sequencing read provides a means to distinguish a pseudogene sequence from an active gene sequence even where the polynucleotide sequence data is similar. For example, in many cases pseudogenes are more heavily methylated than an active gene sequence, so two sequencing reads having the same polynucleotide sequence can be mapped to the pseudogene or active gene depending on the level of methylation present in the read.

In some embodiments, the methods herein are used to enrich target nucleic acids from complex samples, e.g., metagenomic samples. Metagenomic samples include, but are not limited to, environmental samples such as soil, water, and air; agricultural samples such as produce and meat; industrial samples such as generated waste; and biological samples such as forensic collections and bacterial mixtures. The methods are especially beneficial where the target nucleic acids are a minority species in a mixture of nucleic acids. For example, where it is desired to determine whether a sample comprises a particular minority species, the minority species can be specifically captured, isolated from the rest of the nucleic acids in the sample, and subsequently detected. Similarly, where the sample is blood collected from an infected human individual the enrichment can separate human nucleic acids from "non-human" nucleic acids that may be present, as long as a sgRNA, crRNA: tracrRNA, or bis-PNA clamp and complementary oligonucleotides can be designed for the non-human nucleic acids, depending on the enrichment method used. The isolated non-human nucleic acids can be subsequently analyzed to determine their source, e.g., which strain(s) of a pathogenic organism are present in the sample.

Enriched nucleic acid mixtures are useful for many applications apart from sequence analysis, as well as those that include, but go beyond, simple sequence analysis. Certain nonlimiting examples include cloning of a target region, amplification of a target region, separation of nucleic acids from different sources in a complex sample, and the like. Further, such enriched samples are desired for identifying genetic determinants of disease or other disorders, e.g., through prognostic or diagnostic applications. Such targeted biomedical applications are particularly useful for enriching for a gene or genes known to provide a biological basis for a genetic disorder, whether it is a susceptibility or a resistance phenotype, preferably without needing to clone the gene or genes. These gene or genes, once identified and their roles in the disorder understood, can also be used in theranostic applications, for example, in the development of small-molecule-based (e.g., drugs, pro-drugs, etc.) and nucleic-acid-based therapies (e.g., RNAi, antisense oligonucleotides, etc.). Other uses for the enriched nucleic acid mixtures provided by the instant invention will be recognized by those of ordinary skill in the art, as many of the applications are standard in the field of biomedical application, but up until now have suffered from the inability to enrich and analyze large and/or modified nucleic acid fragments, so much genetic information, such as haplotype alleles and base modification data, could not be studied. The methods herein provide new and useful methods for such large and/or modified nucleic acids, thereby generating new possibilities for targeted biomedical applications. Additional compositions, methods, and systems that can be used with those provided herein, or that will benefit from those provided herein, include those described in the following publications, all of which are incorporated herein by reference in their entireties for all purposes: U.S. Pat. Nos. 7,476,503, 7,476,504, 7,935,310, 7,995,202, 8,193,123, 7,715,001, 7,901,889, 7,906,284, 8,003,330, 8,236,499, 8,153,375, 8,247,216, 8,501,405, 8,658,364, and 8,715,930; and U.S. Patent Publication Nos. 2010/0221716, 2010/0323912, 2012/0071359, 2012/0115736, 2012/0196279, 2013/0303385, and 2013/0330722.

Yet further, the methods herein can be used for enriching a nucleic acid sample for multiple different regions, e.g., corresponding to multiple different genes within a metabolic or disease pathway of interest. As noted elsewhere herein, where sources are to be combined prior to analysis (e.g., "multiplexed"), barcodes can be added so the data from the subsequent analysis can be parsed and linked back to the original sources. In some such embodiments, target regions represent a set of genes involved in a biological pathway of interest, e.g., oncogenesis. Adapters specific for each target region comprise barcodes, and these barcodes can provide different types of source information. For example, they can identify the tissue type from which the nucleic acid was isolated or the individual from which the nucleic acid was obtained. In some embodiments, the individual is not identified, but the disease state of the individual is, which is useful for performing multiplexed case-control studies in which nucleic acids from cases and controls are pooled prior to analysis. Since the biological basis for many disorders involves many different genes, it is desirable to multiplex the analysis of a set of genes (a "gene panel") associated with a given disease or disorder. In these applications, each different gene can be provided a different barcode, and/or the barcodes can instead distinguish between tissue sources, patients, disease status, and the like. Yet further, both genomic DNA and mRNA can be isolated and subjected to analysis, where both the genomic sequence information as well as the full-length transcript and/or splice-isoform data generated can better inform the clinician about the disease state of the patient. In such applications a barcode is helpful to distinguish between genomic nucleic acids and transcript sequences, since they can be identical in sequence, at least in exonic regions.

Mosaicism in an individual can also be studied using the methods herein. Mosaicism, mentioned briefly above, is a condition in which two or more genetically distinct cell populations exist in an organism. It can be caused by unequal distribution of genetic material during mitosis such that the daughter cells produced are not identical. Those daughter cells replicate to create populations of cells that are genetically distinct from one another. This phenomenon is commonly observed in highly repetitive regions of a genome, since these regions are often not replicated correctly during cell division. As such, daughter cells can have more or fewer repeats than the parental cells, and they in turn can divide to produce cells that have further differences in copy number. Mosaicism can present in a tissue-specific way, such that a first tissue type in an organism can have a different number of repeats than a second tissue type in the same organism, e.g., where the first and second tissue types are from first and second progenitor cells that differed in the number of repeats each contained. Further, the type of tissue in which a deleterious repeat polymorphism (e.g., repeat expansion) occurs is key to whether the individual will present with a genetic disorder, and the specific type of disorder to which they are potentially susceptible. For example, a repeat expansion in brain tissues may cause a neurological disorder, while one in breast tissue causes breast cancer. The ability to target a repeat region from a particular tissue, enrich for that repeat region, and perform single-molecule sequencing on the region allows the researcher to determine the genotype for that tissue, and that information can be used in prognostic and diagnostic applications for a genetic disorder associated with the repeat region. Comparison of the repeat region from one tissue (e.g., skin) to the repeat region from another tissue (e.g., blood) can also be informative, providing data for which tissue types have expanded repeat regions, and how they can be differently expanded depending on the tissue in which they are being replicated. This is valuable information in the study of repeat-related disorders, and contributes to determination of a genetic cause of a disorder and development of genetic screening tests, and potentially provides insight into how such a disorder can be prevented and/or treated.

VI. Kits

The compositions of the invention are optionally provided in kit form, including various components of an overall analysis in combination with instructions for carrying out the desired analysis. In particular, such kits typically include the various reaction components and compositions of the invention described herein (e.g., bis-PNA clamps, complementary oligonucleotides, affinity tags (e.g., biotin), adapters (e.g., stem-loop adapters), ligases, primers/probes, restriction endonucleases, Cas9 protein, sgRNAs, crRNAs, tracrRNAs, capture tag for sgRNAs, magnetic beads, etc.) Optionally kits include components of sequencing reactions, e.g., at least one, but preferably multiple types of labeled nucleotide analogs, e.g., A, T, G and C analogs. Each of the different types of labeled nucleotide analogs in the kit will typically comprise a distinguishable labeling group, as set forth above. In addition to the analog compositions, the kits will optionally include one or more components of a polymerase complex, including, for example polymerase enzymes, such as any of a number of different types of strand displacing polymerase enzymes. Examples of such polymerases include, e.g., phi29-derived polymerases, and the polymerase enzymes described in, e.g., Published International Patent Application Nos. WO 2007/075987, WO 2007/075873 and WO 2007/076057, the full disclosures of which are incorporated herein by reference in their entirety for all purposes.

Additional reaction components are also optionally included in such kits, such as buffers, salts, universal priming sequences (primers) for initiation of synthesis, and the like. In addition, in particularly preferred aspects, the kits of the invention can further include a reaction substrate that includes reaction regions for carrying out and observing the synthesis reactions for identification of sequence information. Such substrates include, e.g., multi-well micro or nano plates, as well as arrayed substrates, e.g., planar transparent arrays that include discrete reaction regions defined by, e.g., structural, chemical or other means. For example, patterned arrays of complexes may be provided disposed upon planar transparent substrates for observation. Alternatively and preferably, the substrate component comprises an array or arrays of optically confined structures like zero-mode waveguides. Examples of arrays of zero-mode waveguides are described in, e.g., U.S. Pat. No. 7,170,050, the full disclosure of which is incorporated herein by reference in its entirety for all purposes.

EXAMPLES

1. Enrichment Using Bis-PNA Clamps

An embodiment of the methods described herein was performed as follows. Data generated is also provided below. The target region intended for enrichment was the human HTT region, and a 2 kb human genomic library was the starting sample nucleic acid. The HTT region represents 0.0001 w/w % of the entire human genome.

The following components for hybridization of bis-PNA clamps to a target sequence were mixed in 0.5 ml LoBind microcentrifuge tubes (Eppendorf): 10 µl of 12.5 mM Tris acetate pH 8.0, 8 µl of a solution containing 2.5 µM of a first bis-PNA clamp and 2.5 µM of a second bis-PNA clamp, 10 µg of sample nucleic acid in Qiagen EB; and ultrapure water to bring the volume to 100 µl. The sample nucleic acid was a library comprising double-stranded sample nucleic acid fragments that were capped at the ends with stem-loop adapters (also termed a SMRtTbell$^{SM}$ library).

The mixture was heated to 95° C. for 2 minutes to denature the double-stranded portions of the sample nucleic acid, and was subsequently fast cooled on ice. After incubation for one hour on ice, 60 µl of AMPure® magnetic beads (Agencourt) were added and the mixture was vortexed at 2050 rpm for ten minutes. The beads were pelleted on a magnet stand and washed according to the manufacturer's instructions. Following the wash, the sample nucleic acid was eluted off the beads into 40 µl of 25 mM MES, pH 6.1, 0.1 mM EDTA. Next, 10 µl of a solution of 1 M NaCl and 25 mM MES, pH 6.1, 0.1 mM EDTA, was added to the eluted nucleic acid and mixed well. The resulting solution was incubated at 37° C. for one hour to dissociate any non-specifically bound bis-PNA clamps.

After the incubation, the following mixture was added to the solution in order to bind biotinylated complementary oligonucleotide to the displaced strand: 1.8 µl ultrapure (Milli-Q®) water; 2.5 µl of 100 mM MES, pH 6.1; 4 µl of 5 M NaCl; 1.5 µl of 0.1 µM biotinylated complementary oligonucleotide; and 0.2 µl of 5 mM EDTA, pH 8.0. The resulting mixture was incubated at 37° C. for one hour. To remove the oligonucleotide that didn't bind to the displaced strand, 36 µl of AMPure® beads (Agencourt) were added and the mixture was vortexed at 2050 rpm for ten minutes. The beads were pelleted on a magnet stand and washed according to the manufacturer's instructions. Following the wash, the sample nucleic acid was eluted off the beads into 40 µl of a solution of 60 mM NaCl and 25 mM MES, pH 6.1. Next, 20 µl of a solution of 1.38 M NaCl; 25 mM MES, pH 6.1; and 0.1 mM EDTA was added to the eluted sample nucleic acid and mixed well. The resulting solution was incubated at 37° C. for one hour to dissociate any non-specifically bound complementary oligonucleotide prior to addition of washed, streptavidin-coated magnetic beads, the preparation of which is described infra.

Streptavidin-coated magnetic beads M280 (Invitrogen) were prepared as follows. First, the bead suspension was vortexed for 30 seconds, and 40 µl of the suspension was pipetted into a 1.5 ml LoBind microcentrifuge tube (Eppendorf). Next, 1 ml of B&W buffer (5 mM Tris, pH 7.5; 0.5 mM EDTA; and 1 M NaCl) was added and the mixture was thoroughly vortexed and placed on the magnet stand to pellet the beads for one minute. The supernatant was removed and the beads were resuspended in 1 ml of B&W buffer, after which the beads were pelleted on the magnet stand for one minute. This wash was repeated twice, after which the beads were resuspended in 1 ml of Buffer B (1×PBS, 1 mg/ml BSA, and 0.2 mg/ml yeast tRNAs). This resuspension was incubated on a rotor for constant mixing for 20 minutes at room temperature, then the beads were pelleted on the magnet stand for one minute before discarding the supernatant. Once again, the beads were resuspended in 1 ml of Buffer B and incubated on the rotor for constant mixing for 20 minutes at room temperature before pelleting on the magnet stand and discarding the supernatant. Finally, the beads were washed in 1 ml of Buffer III (50 mM Tris, pH 7.5; 10 mM EDTA; 15 mM sodium-azide; and 0.01 w/v % Triton X-100 with 75 mM NaCl) twice. After the second wash, the beads were resuspended in 40 µl Buffer IIIb (50 mM Tris, pH 7.5; 10 mM EDTA; 15 mM sodium-azide; and 0.01 w/v % Triton X-100).

Once the streptavidin-coated beads were washed, 40 µl of the washed beads was added to the eluted sample nucleic acids and the mixture was incubated at room temperature for two hours with constant rolling to keep the beads from settling. Following this incubation, the beads were pelleted on the magnet stand, the supernatant was discarded, and the beads were resuspended in 400 µl of Buffer III before re-pelleting on the magnet stand. The supernatant was discarded and the Buffer III wash was repeated once again. After discarding the supernatant of the second wash, the beads were resuspended in 150 µl of Buffer III, and the resulting suspension was transferred into 1.5 mL LoBind tubes (Eppendorf). Again, the beads were pelleted and the supernatant discarded. The beads were resuspended in 50 µl of Buffer D (1× TE and 1 M NaCl), and the tube placed on a shaker at 1400 rpm at 80° C. for 20 minutes. Afterward, the contents of the tubes were spun down and the beads were pelleted on the magnet stand. The supernatant was collected and the beads were discarded. The supernatant was mixed with 90 µl of AMPure beads (Agencourt) and vortexed at 2050 rpm for 10 minutes. The beads were pelleted and washed according to the manufacturer's recommendations. The DNA was eluted off the beads in 50 µl of Qiagen's EB (elution buffer). The DNA was now ready for quantification and sequencing.

Next, the eluted DNA was subjected to a primer annealing reaction containing 50 µl of DNA eluate in Qiagen's EB, 6 µl of 10× Primer Annealing Buffer (Pacific Biosciences), 0.9 µl of Pacific Biosciences' Sequencing Primer, and 3.1 µl ultrapure)(Milli-Q®) water. The primer was annealed according to Pacific Biosciences' recommendations. Afterwards, the excess sequencing primer was removed by the addition of 36 µl AMPure® beads (Agencourt) and vortexed at 2050 rpms for 10 minutes. The beads were pelleted and washed according to the manufacturer's recommendations. The DNA was eluted off the beads into 50 µl of a solution of 12.5 mM Tris acetate, pH 8.0 and 12.5 mM potassium acetate. After the elution, 10 µl of a solution of 12.5 mM Tris acetate, pH 8.0; 12.5 mM potassium acetate; 0.375 w/v % Tween 20; and 13.5 nM stem-loop adapters was added to the DNA eluate. 60 µl of the final solution was mixed with 10× PacBio® Binding Buffer, 10×DTT, and 10× dNTPs from Pacific Biosciences according to the manufacturer's recommendations with the final PacBio® P4 polymerase concentration of 0.3 nM. The mixture was incubated at 30° C. for 4 hours. The sample was immobilized on magnetic beads via the surface-linked $dT_{25}$ oligonucleotides (Pacific Biosciences) and sequenced on the PacBio® RS intrument. This protocol for primer annealing and polymerase binding to a template nucleic acid was found to increase the yield of sequencing reads where the amount of sample nucleic acid was limiting, e.g., below 5 pM.

The DNA was subjected to single-molecule, real-time (SMRT) sequencing in two SMRT Cells using the two-hour movie protocol. The sequence reads generated were analyzed to determine the level of enrichment for the target region. The results demonstrated that enrichment of the HTT region was improved by performing the bis-PNA binding under low ionic strength conditions, with a greater than seven-fold increase in enrichment as compared to standard binding conditions.

2. Enrichment of dnaE Gene

An embodiment of the methods described herein was performed as follows. Data generated is also provided below. The target region intended for enrichment was the ~3.5 kb *E. coli* dnaE gene, from which a 2-kb *E. coli* MG1655 genomic library was created.

Figure 8:
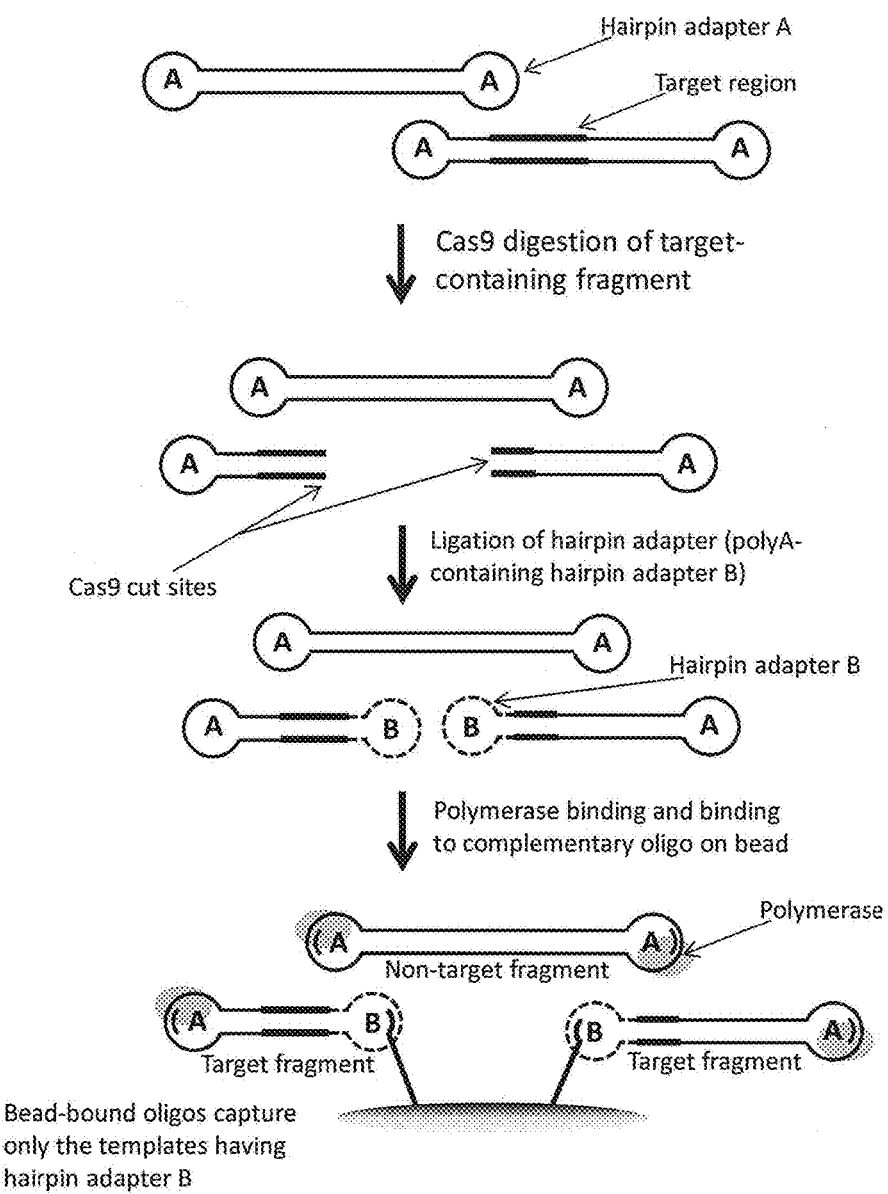
FIG. 8 provides a flow diagram depicting the strategy used to enrich fragments comprising portions of the dnaE gene.

A flow diagram for the enrichment of the dnaE gene is provided in FIG. 8. To create the starting DNA library, genomic DNA from *E. coli* MG1655 was sheared to produce fragments averaging about 2 kb, and the fragments were end-repaired to create blunt ends and ligated to hairpin adapter A. The resulting library therefore contained a subset of hairpin-capped fragments with the target region (dnaE gene) and the remaining majority of hairpin-capped fragments lacking the target region. This library of fragments was treated with an RNA-Cas9 complex targeting a cleavage site within the target region to generate double-stranded ends at the cut site. Specifically, the RNA-Cas9 complex, which comprised a crRNA and a tracrRNA, cut within the dnaE gene between base 853 and 854 from the 5' end of the reference sequence: EG10238 dnaE DNA polymerase III, alpha subunit. The crRNA sequence used to target the cleavage site was 5'-AUCUUCGGUGCUCAUGUC-CCGUUUUAGAGCUAUGCUGUUUUG-3' (SEQ ID NO: 6), with the 20 RNA bases at the 5' end complementary to the sample nucleic acid. The Cas9 reaction mixture included 20 mM HEPES, pH 7.5 (up to pH 8.0 is acceptable), 100 mM KCl, 5 v/v % glycerol, 1 mM TCEP, 5 mM $MgCl_2$, 1 U/µl RNAse inhibitor (e.g., SUPERase• In™ RNase inhibitor from Life Technologies), 48 nM of tracrRNA:crRNA, and 32 nM Cas9 enzyme (*S. pyogenes* Cas9 enzyme from NEB). Various concentrations of heparin (0, 1, 3, 5, and 10 µg/µl) were also tested in the reaction mixtures to test its effects on the cleavage reaction, and it was found that addition of heparin at a concentration of 1-10 µg/µl improved the cleavage reaction. Following the cleavage reaction, EDTA was added and the mixture was purified using AMPure® PB beads to remove contaminants. A second hairpin adapter (B) having a different sequence than the first hairpin adapter (A) was ligated to the double stranded ends produced by the Cas9 cleavage to produce nucleic acids having portions of the target region either upstream or downstream of the cut site and two different hairpin adapters, A and B. The mixture was subsequently treated with exonucleases (ExoIII and Exo VII) to degrade any nucleic acids that were not capped at both ends by a hairpin adapter, and the resulting mixture was purified twice using AMPure® PB beads to remove the degraded non-target nucleic acids. The resulting mixture had non-target fragments with symmetric hairpin adapters (both A) and target fragments with asymmetric hairpin adapters (one A and one B). The fragments that had not been cut by Cas9 still had the A adapter at both ends. Adapter A comprised a sequencing primer binding site, so all fragments having adapter A could form a sequencing complex having a sequencing primer and a polymerase, shown as a grey oval. Adapter B comprised a polyA region complementary to a polyT oligonucleotide bound to a magnetic bead. As such, only fragments having adapter B (target fragments) could bind to the oligonucleotide-bead complex. Once the target fragments were bound to the bead, the non-target fragments lacking adapter B were removed to provide a sample enriched for the target fragments. The captured fragments on the magnetic beads were loaded into a SMRT® Cell and sequenced using single-molecule, real-time (SMRT®) sequencing on a PacBio® RS II instrument to determine the success of the enrichment procedure.

Figure 9:
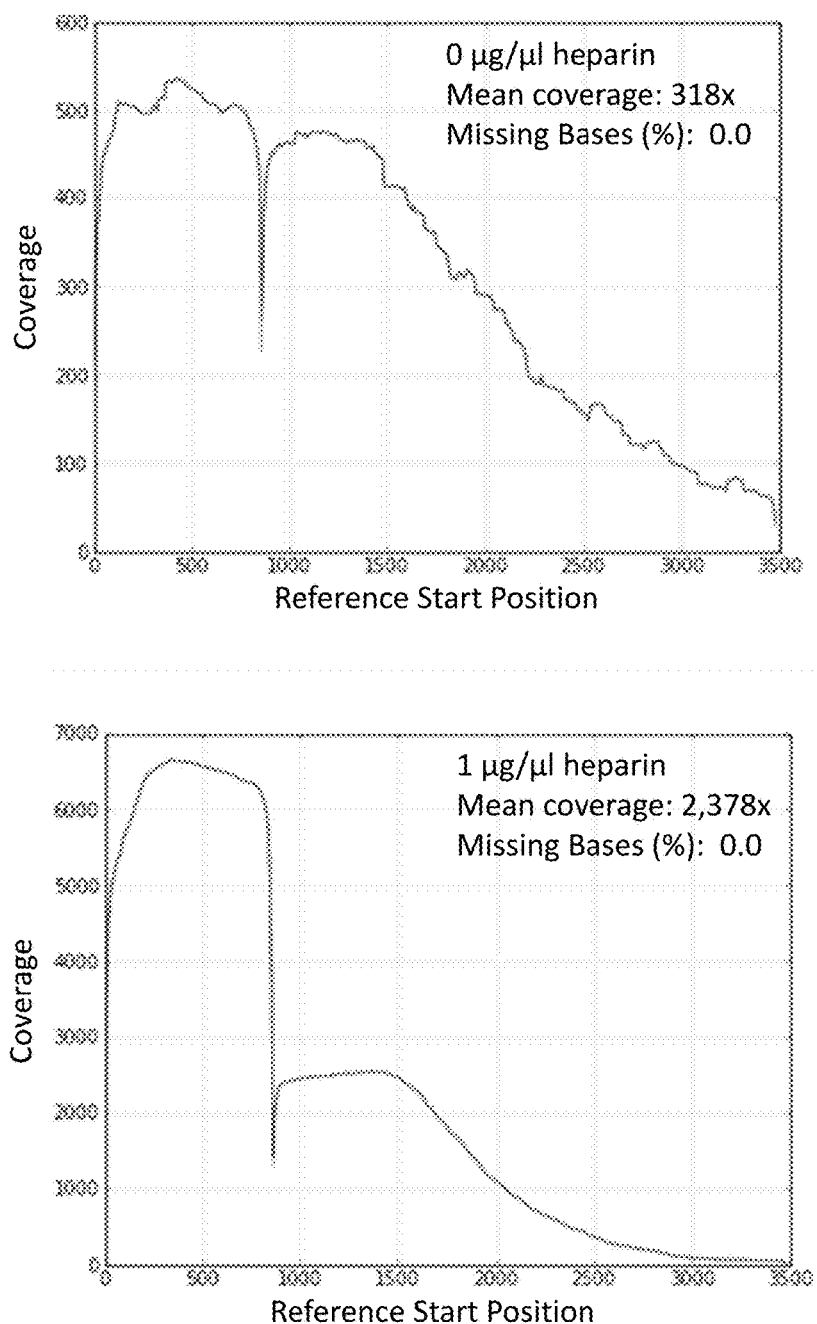
FIG. 9 provides exemplary graphs showing sequencing coverage for the dnaE gene following enrichment of an *E. coli* genomic library.

Sequences were obtained for portions of the dnaE gene on both sides of the cut site and sequence for the entire gene was generated, but the relative amounts of sequence coverage varied depending on the presence of heparin in the cleavage reaction mix and the distance from the cut site. Exemplary graphs of these results are shown in FIG. 9. In the presence of no heparin (top graph), there was similar sequencing depth on both sides of the cut site, although that coverage fell off for sequences more distal to the cut site. The mean coverage in the absence of heparin was about 318-fold. The bottom graph shows exemplary sequencing data when the cleavage reaction occurred in the presence of 1 µg/µl of heparin. Interestingly, the relative amounts of sequencing coverage are significantly different on different sides of the cut site in the presence of heparin, with the side comprising the region complementary to the crRNA having a significantly lower coverage than the side that is not complementary to the crRNA. However, even with this characteristic, the sequence for the entire dnaE gene was obtained and the overall coverage is far higher in the presence of heparin, with a mean coverage of 2378-fold. The maximum coverage for the over-represented side is between 6000- and 7000-fold, and the maximum coverage for the under-represented side is between 2000- and 3000-fold, with the coverage level decreasing farther from the cut site. The decreasing coverage further from the cleavage site is primarily due to the average size of the fragments in the initial DNA library (2 kb), with the presence of some longer fragments providing sequence data across the entire gene.

3. Enrichment of the HTT Gene Repeat Region

An embodiment of the methods described herein was performed to enrich for the CAG repeat region within the human HTT gene, which is known to be associated with Huntington disease. The sample nucleic acid was a DNA library prepared from whole human genomic DNA (from embryonic kidney cells) in essentially the same manner as the dnaE library described above, except that the starting genomic DNA was that of human rather than *E. coli*. Specifically, the whole human genomic DNA was randomly sheared into fragments having an average size of about 2 kb, and the ends were repaired to create blunt ends and ligating stem-loop adapters to both ends of the resulting fragments to produce a library of fragments capped by the same stem-loop adapters used for the initial *E. coli* library (adapter A).

Figure 10:
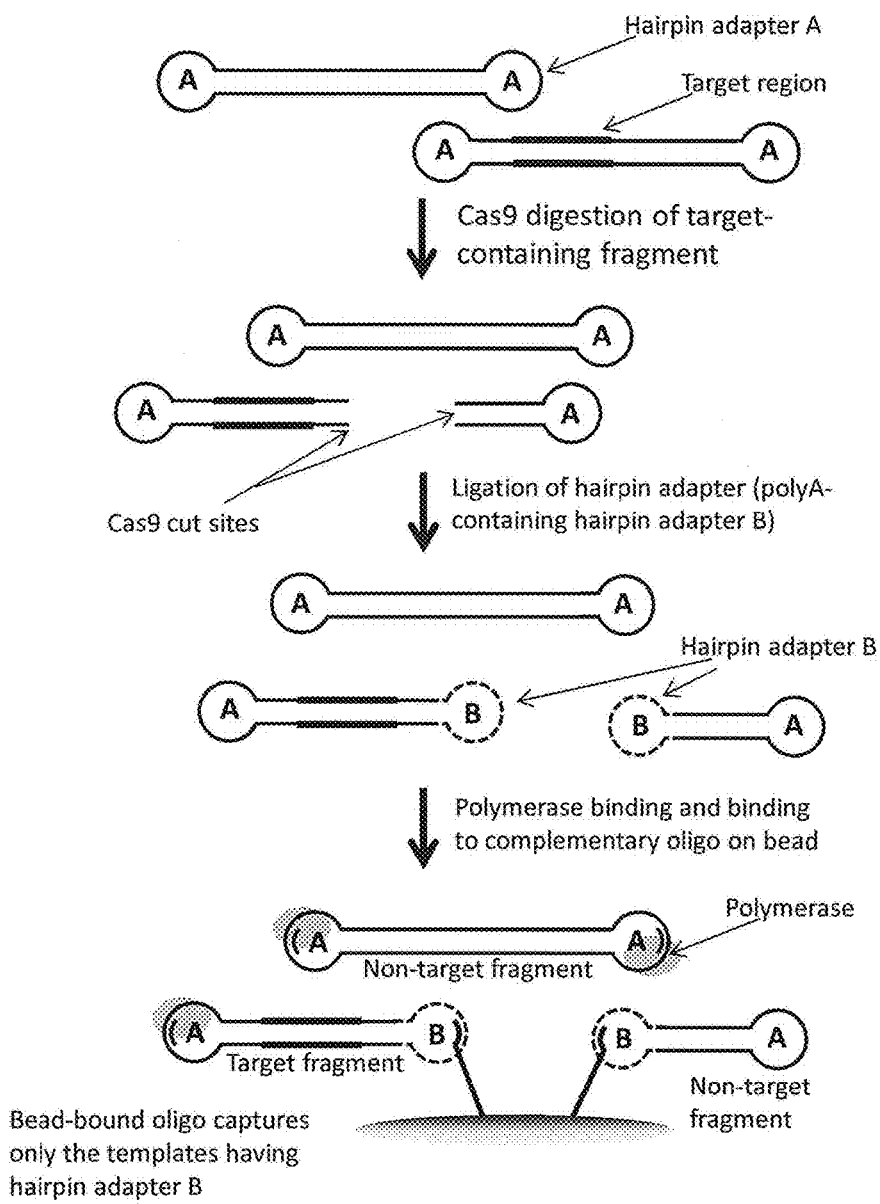
FIG. 10 provides a flow diagram depicting the strategy used to enrich fragments comprising the CAG repeat region of the HTT gene.

FIG. 10 provides a general flow diagram for the method used to enrich the human genomic library for the HTT repeat region. Three different crRNAs were designed to target sites outside of the CAG repeat in order to test which would provide the most effective cleavage by Cas9 endonuclease. crRNA #724 (5'-GUCAAUCAUGCUGGCCGGCG- GUUUUAGAGCUAUGCUGUUUUG-3') (SEQ ID NO 1) is complementary to a locus about 270 base pairs upstream of the repeat region; crRNA #722 (5'-UCCAAGAUG-GACGGCCGCUCGUUUUAGAGCUAUGCUGUUUUG-3') (SEQ ID NO 2) is complementary to a locus about 160 base pairs upstream of the repeat region; and crRNA #723 (5'-AGCGGGCCCAAACUCACGGUGUUUUAGAGC-UAUGCUGUUUUG-3') (SEQ ID NO 3) is complementary to a locus about 150 base pairs downstream from the repeat region. The crRNAs were designed to associate with the target nucleic acid in a particular orientation, specifically with the 5' end (complementary to the target fragment) farthest from the target region and the 3' end closest to the target region. This orientation was chosen to maximize the fold-coverage for the target region in the presence of heparin (3 μg/μl). All the other reaction conditions were the same as that described above for the dnaE gene enrichment. Each Cas9 cleavage reaction mixture had only one type of RNA-Cas9 complex comprising one of the above-described crRNAs along with a tracrRNA, so each reaction cut only once within a target fragment comprising the CAG repeat region.

Following the cleavage reactions, EDTA was added and the mixtures were purified using AMPure® PB beads to remove contaminants. There was no end-repair step prior to ligation of the mixture to the "polyA hairpin adapter" (B), which is the same polyA-containing hairpin adapter as was used during the above-described dnaE enrichment. The mixture was subsequently treated with exonucleases (ExoIII and Exo VII) to degrade any nucleic acids that were not capped at both ends by a hairpin adapter, and the resulting mixture was purified twice using AMPure® PB beads to remove the degraded non-target nucleic acids. This resulted in a mixture of non-target fragments having adapter A at both ends, target fragments having adapter A at one end and adapter B at the opposite end, and a small portion of non-target fragments having adapter A at one end and adapter B at the opposite end. The latter are the fragments produced by Cas9 cleavage that do not comprise the target region but do comprise the sequence complementary to the crRNA in the RNA-Cas9 complex. The hairpin-capped fragments recovered from the AMPure® PB beads were exposed to polyT oligonucleotides bound to magnetic beads to capture only those fragments having a B adapter, which includes a polyA region. Nucleic acids that did not bind to the bead (e.g., non-target fragments having A adapters at both ends) were removed and the captured fragments on the magnetic beads were loaded into a SMRT® Cell and sequenced using single-molecule, real-time (SMRT) sequencing on a PacBio® RS II instrument. All of the crRNAs tested were able to target the Cas9 nuclease to produce a mixture of fragments enriched for the repeat region. The results from all three crRNA were similar, and sequencing of the fragments produced sufficient sequence data to accurately determine the sequence of the repeat region, including the number of CAG repeats. As observed for the dnaE gene enrichment, the sequencing data revealed bias in which side of the Cas9 cleavage was enriched. Although sufficient sequence data was generated on the side of the cleavage corresponding to the target fragment to fully sequence the CAG repeat region, no sequence data was obtained for the fragment generated on the non-target side of the cleavage. While the basis for this unequal enrichment on each side of the Cas9 cleavage site is not fully understood, several factors may play a part including a less efficient ligation to hairpin adapter B on the non-target side of the cleavage, possibly due to steric interference caused by the RNA-Cas9 complex bound to the non-target fragment. A low ligation efficiency would result in degradation of much of the non-target fragment during the exonuclease treatment. Alternatively or additionally, there may also be loading bias onto the sequencing instrument where the non-target cleavage product is small; it has been found that small fragments load less easily using the magnetic bead loading method than larger fragments. In any case, the specific design of the crRNA and use of heparin to take advantage of this bias was shown to provide sufficient enrichment for successful sequence analysis of this target region.

Figure 11:
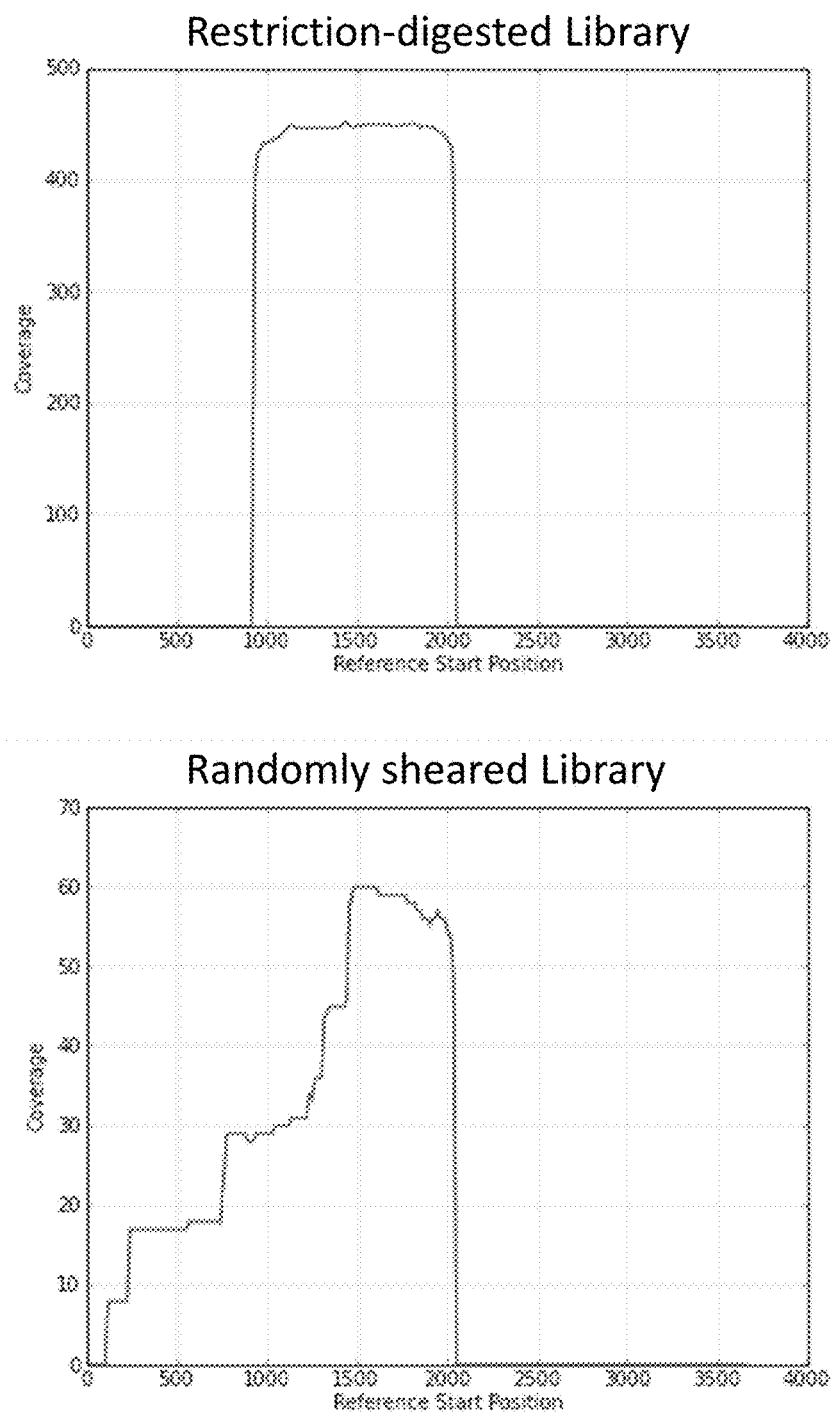
FIG. 11 provides exemplary graphs showing sequencing coverage for the CAG repeat region of the HTT gene following enrichment of a human genomic library.

Similar experiments were subsequently carried out on this same region of the HTT gene, but using a human genomic library prepared with restriction endonuclease digest using EcoRI and BamHI rather than random shearing. Only one RNA-Cas9 complex comprising crRNA #723 was tested, and all other reaction conditions were as is described above for the sheared human library. It was found that the subsequent sequencing of the enriched fragments contained more even coverage of the target region, generally extending from the Cas9 cut site to the BamHI restriction site at the opposite end of the target fragment. FIG. 11 shows the coverage plots for the sequencing of fragments enriched from a library prepared by cutting with EcoRI and BamHI (A) versus a library prepared using random shearing (B). In the coverage plots, the Cas9 digestion site is located at 2048 by along the bottom axis (Reference Start Position). The CAG repeat region is located from 1837 bp to 1893 bp. Sequencing of the enriched fragments from the restriction-digested library provided approximately 450-fold coverage of the target region. In contrast, sequencing of the enriched fragments from the randomly sheared library only provided about 55-fold coverage of the target region. This level of coverage is adequate for many sequencing applications, but generally higher coverage is desirable to provide higher quality consensus sequences.

Optimizations were also performed on the sequencing reactions of the enriched target fragments. It was found that heating only the primer prior to hybridization of the primer to the template increased the sequencing yield over heating both the primer and template prior to hybridization.

The human genome is about 3 Gb and the mean fragment size sequenced was about 1.1 kb. As such, on average, $2.73 \times 10^6$ fragments need to be sequenced to have one of them contain a single region of interest, e.g., the HTT repeat region. The method described above provided greater than 21,000-fold enrichment of the HTT repeat region, allowing targeted sequencing of this region from a human whole-genome library.

4. Enrichment of the FMR1 Repeat Region

An embodiment of the methods described herein was performed to enrich for the CGG repeat region within the human FMR1 gene, which is known to be associated with Fragile X syndrome. The sample nucleic acid was the same as that described above for the HTT enrichment. Briefly, EcoRI and BamHI were used to fragment the genome and the same stem-loop adapters were used to produce the starting library of fragments. This library was subjected to a Cas9 cleavage react on using a crRNA having the sequence 5'-AGAGGCCGAACUGGGAUAACGUUUUAGAGC-UAUGCUGUUUUG-3' (SEQ ID NO 4). The locus to which it binds is from base 146993105 to 146993124 on chromosome X in the hg19 human reference sequence; Cas9 cuts between positions 146993121 and 146993122. The CGG repeat region begins at base 146993569. As such, the Cas9 cut site is 448 basepairs away from 5' end of the repeat legion. The crRNA hybridized to the target fragment in the library with the 3' end closest to the target region having the CGG repeat region. All the other reaction conditions were the same as that described above for the HTT repeat region enrichment. Following AMPure® PB bead purification, the Cas9 cleavage products were ligated to the polyA-containing adapters. Subsequent exonuclease treatment with ExoIII and Exo VII degraded nucleic acids that were not capped at both ends by a hairpin adapter, and the resulting mixture was purified using AMPure® PB beads to provide a mixture of adapter-flanked fragments. Following isolation of fragments linked to the polyA-containing adapters using the polyT-linked magnetic beads, the captured fragments were loaded into a SMRT® Cell and sequenced using single-molecule, real-time (SMRT®) sequencing on a PacBio® RS II instrument. Enrichment for the CGG region was observed, and sequencing of the fragments produced sufficient sequence data to accurately determine the sequence of a FMR1 CGG repeat region comprising 30 repeats (data not shown).

5. Multiplex Enrichment of HTT and FMR1 Target Regions

A multiplex embodiment of the methods described herein was performed to enrich for both the CAG repeat region within the human HTT gene and the CGG repeat region within the FMR1 gene. The library was the EcoRI-BamHI library described above, and the reaction conditions were the same as that used for the HTT and FMR1 repeat region enrichments supra. Two crRNAs (crRNA #723 and the FMR1 crRNA above) were used in a single Cas9 cleavage reaction to enrich both the CAG and CGG repeat regions in a single enrichment procedure. The total concentration of crRNA:tracrRNA was still 48 nM, with half of the complexes having the HTT-specific crRNA and half having the FMR1-specific crRNA. The experiment demonstrated that the Cas9 enrichment method works not only for a single target region, but that multiple target regions can be enriched in a single reaction mixture.

6. Enrichment of ALS Repeat Region

An embodiment of the methods described herein was performed to enrich for the GGGGCC hexanucleotide repeat region within the human ALS gene, which is known to be associated with amyotrophic lateral sclerosis, or "Lou Gehrig's disease." The sample nucleic acid was the same as that described above for the HTT and FMR1 enrichments described above. Briefly, EcoRI and BamHI were used to fragment the genome and the same stem-loop adapters were used to produce the starting library of fragments. This library was subjected to a Cas9 cleavage reaction using a crRNA having the sequence 5'-GCAAUUCCACCAGU-CGCUAGGUUUUAGAGCUAUGCUGUUUUG-3' (SEQ ID NO 5). The locus to which it binds is from base 27573256 to 27573275 on chromosome 9 in the hg19 human reference sequence; Cas9 cuts between positions 27573272 and 27573273. The GGGGCC repeat region begins at base 27573527. As such, the Cas9 cut site is 255 basepairs away from 5' end of the repeat region. The crRNA hybridized to the target fragment in the library with the 3' end closest to the target region having the GGGGCC repeat region. All the other reaction conditions were the same as that described above for the HTT repeat region enrichment. Following AMPure® PB bead purification, the Cas9 cleavage products were ligated to the polyA-containing adapters. Subsequent nuclease treatment with ExoIII, Exo VII, and PvuII degraded nucleic acids that were not capped at both ends by a hairpin adapter with the PvuII further cleaving non-target fragments comprising PvuII restriction sites, and the resulting mixture was purified using AMPure® PB beads to provide a mixture of adapter-flanked fragments. Following isolation of fragments linked to the polyA-containing adapters using the polyT-linked magnetic beads, the captured fragments were loaded into a SMRT® Cell and sequenced using single-molecule, real-time (SMRT®) sequencing on a PacBio® RS II instrument. Enrichment for the GGGGCC region was observed, and sequencing of the fragments produced sufficient sequence data to accurately determine the sequence of two ALS GGGGCC repeat regions, one comprising two repeats and the other comprising four repeats. It is believed that the two-repeat allele and four-repeat allele are the two alleles for the diploid genome, i.e., each allele is on a different homolog of chromosome 9.

7. Multiplex Enrichment of HTT, FMR1 and ALS Target Regions

A multiplex embodiment of the methods described herein was performed to enrich for three target regions: the CAG repeat region within the human HTT gene, the CGG repeat region within the FMR1 gene, and the GGGGCC repeat region of the ALS gene. The library was the EcoRI-BamHI library described above, and the reaction conditions were the same as that used for the multiplex enrichment of the HTT and FMR1 repeat regions supra. Three crRNAs (crRNA #723, the FMR1 crRNA, and the ALS crRNA above) were used in a single Cas9 cleavage reaction to enrich all three repeat regions in a single enrichment procedure. The total concentration of crRNA:tracrRNA was still 48 nM, with one third of the complexes having the HTT-specific crRNA, one third having the FMR1-specific crRNA, and one third having the ALS-specific crRNA. The experiment demonstrated that the Cas9 enrichment method can be successfully implemented for three different target regions in a single reaction mixture.

Although described in some detail for purposes of illustration and clarity, it will be readily appreciated from a reading of this disclosure that various changes in form and detail that are known or appreciated by those of skill in the art may be practiced without departing from the true scope of the invention. For example, all the techniques and apparatus described above can be used in various combinations, e.g., sequentially or simultaneously. All terms used herein are intended to have their ordinary meaning unless an alternative definition is expressly provided or is clear from the context used therein. To the extent any definition is expressly stated in a patent or publication that is incorporated herein by reference, such definition is expressly disclaimed to the extent that it is in conflict with the ordinary meaning of such terms, unless such definition is specifically and expressly incorporated herein, or it is clear from the context that such definition was intended herein. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all publications, patents, patent applications, and/or other documents referred to in this disclosure are incorporated herein by reference in their entireties for all purposes to the same extent as if each individual publication, patent, patent application, and/or other document were individually and separately indicated to be incorporated by reference for all purposes.

The invention claimed is:

1. A method for enrichment of a target region in a DNA library comprising:
   a) providing a DNA library of double-stranded fragments with hairpin adapters on both ends, wherein the double-stranded fragments in the DNA library are not amplified nucleic acids, and wherein one or more of the double-stranded fragments are target fragments that comprise the target region;
   b) subjecting the DNA library to endonuclease cleavage with an engineered endonuclease from a gene editing system that cleaves the target fragments at a first location to produce double-stranded ends, wherein the first location is present only once within at least one of the target fragments and is not within the target region;
   c) linking stem-loop adapters to the double-stranded ends produced by the endonuclease cleavage, thereby forming asymmetric-adapter-ligated fragments, wherein the stem-loop adapters have a different sequence than the hairpin adapters; and
   d) isolating the asymmetric-adapter-ligated fragments from other fragments in the reaction mixture that are not linked to the stem-loop adapters.

2. The method of claim 1, wherein each of the hairpin adapters comprises a primer binding site complementary to a sequencing primer.

3. The method of claim 1, wherein each of the stem-loop adapters comprises an oligonucleotide binding site complementary to an oligonucleotide linked to a solid surface.

4. The method of claim 3, wherein the solid surface is a bead.

5. The method of claim 1, further comprising subjecting the asymmetric-adapter-ligated fragments isolated in d) to a single-molecule sequencing reaction.

6. The method of claim 5, wherein the single-molecule sequencing reaction is a sequencing-by-synthesis reaction.

7. The method of claim 5, wherein the single-molecule sequencing reaction is a nanopore sequencing reaction.

8. The method of claim 5, wherein the single-molecule sequencing reaction generates redundant sequence information from single molecules of the asymmetric-adapter-ligated fragments isolated in d).

9. The method of claim 1, further comprising amplifying the asymmetric-adapter-ligated fragments isolated in d).

10. The method of claim 1, wherein the DNA library is a whole-genome DNA library.

11. The method of claim 1, wherein the target region is a repeat region comprising at least 50 repeats.

12. The method of claim 1, wherein the target region is a repeat region that is a diagnostic marker.

13. The method of claim 1, wherein the target region comprises epigenetic modifications.

14. The method of claim 13, wherein the target region comprises an imprinted gene.

15. The method of claim 1, wherein the target region is a repeat region comprising sequence interruptions, and further wherein the asymmetric-adapter-ligated fragments isolated in d) are sequenced using a technology that can both determine how many repeats are in the repeat region and can identify each of the sequence interruptions in the repeat region.

16. The method of claim 1, wherein the target region is a repeat region comprising epigenetic modifications, and further wherein the asymmetric-adapter-ligated fragments isolated in d) are sequenced using a single-molecule sequencing technology that can detect both a nucleotide sequence and the epigenetic modifications during a single sequencing reaction.

17. The method of claim 1, wherein the target region is a full-length gene.

18. The method of claim 1, wherein the first location is at least 100 base pairs away from the target region.

19. The method of claim 1, wherein the first location is at least 150 base pairs away from the target region.

20. The method of claim 1, wherein the first location is at least 200 base pairs away from the target region.

21. The method of claim 1, wherein, in step b), an RNA-endonuclease complex associates with the target fragments such that the 3' end of a targeting RNA is nearer to the target region.

22. The method of claim 1, wherein no end repair is performed following the endonuclease cleavage and prior to the linking of said stem-loop adapters.

23. The method of claim 1, where the engineered endonuclease from a gene editing system is selected from the group consisting of: a TAL Effector Nuclease and a zinc-finger nuclease.

24. The method of claim 1, wherein the gene editing system is a CRISPR-Cas system.

25. The method of claim 24, wherein the engineered endonuclease is an RNA-Cas 9 complex, wherein at least one targeting RNA in the RNA-Cas 9 complex comprises a sequence complementary to the first location, wherein subjecting step b) comprises combining the RNA-Cas 9 complex with the DNA library in a reaction mixture under conditions that promote binding of the RNA-endonuclease complex to the first location in the target fragments.

26. The method of claim 25, wherein the RNA-Cas 9 complex comprises a single targeting RNA.

27. The method of claim 25, wherein the RNA-Cas 9 complex comprises two targeting RNAs.

* * * * *